US008420084B2

(12) United States Patent
Terrett et al.

(10) Patent No.: US 8,420,084 B2
(45) Date of Patent: Apr. 16, 2013

(54) FULLY HUMAN ANTIBODIES SPECIFIC TO CADM1

(75) Inventors: Jonathan Alexander Terrett, Sunnyvale, CA (US); Heidi Leblanc, Mountain View, CA (US); Haichun Huang, Fremont, CA (US); Erika Meaddough, Gilroy, CA (US); Chin Pan, Los Altos, CA (US); Bingliang Chen, Alameda, CA (US); Chetana Rao-Naik, Walnut Creek, CA (US)

(73) Assignees: Medarex, Inc., Princeton, NJ (US); Oxford BioTherapeutics Ltd, Abingdon (GB)

( * ) Notice: Subject to any disclaimer, the term of this patent is extended or adjusted under 35 U.S.C. 154(b) by 0 days.

(21) Appl. No.: 13/254,752

(22) PCT Filed: Mar. 5, 2010

(86) PCT No.: PCT/US2010/026315
§ 371 (c)(1),
(2), (4) Date: Sep. 2, 2011

(87) PCT Pub. No.: WO2010/102175
PCT Pub. Date: Sep. 10, 2010

(65) Prior Publication Data
US 2012/0093826 A1 Apr. 19, 2012

Related U.S. Application Data

(60) Provisional application No. 61/209,471, filed on Mar. 5, 2009, provisional application No. 61/209,390, filed on Mar. 5, 2009.

(51) Int. Cl.
*A61K 39/395* (2006.01)
*C07K 16/00* (2006.01)
*C07K 16/46* (2006.01)

(52) U.S. Cl.
USPC .................. 424/130.1; 424/133.1; 424/138.1; 530/387.1; 530/387.3; 530/388.25; 530/391.7

(58) Field of Classification Search ........................ None
See application file for complete search history.

(56) References Cited

U.S. PATENT DOCUMENTS

| 6,512,095 | B2 | 1/2003 | Baum |
| 6,596,493 | B1 | 7/2003 | Reeves et al. |
| 7,129,338 | B1 | 10/2006 | Ota et al. |
| 7,153,657 | B2 | 12/2006 | Reeves et al. |
| 7,189,566 | B2 | 3/2007 | Botstein et al. |
| 7,267,960 | B2 | 9/2007 | Galibert et al. |
| 7,368,531 | B2 | 5/2008 | Rosen et al. |
| 7,402,655 | B2 | 7/2008 | Baum et al. |
| 7,411,051 | B2 | 8/2008 | Rosen et al. |
| 7,446,176 | B2 | 11/2008 | Ni et al. |
| 7,608,413 | B1 | 10/2009 | Joseloff et al. |
| 7,659,385 | B2 | 2/2010 | Baum et al. |
| 7,741,115 | B2 | 6/2010 | Baum et al. |
| 7,807,392 | B1 | 10/2010 | Domon et al. |
| 7,833,712 | B2 | 11/2010 | Reeves et al. |
| 7,842,291 | B1 | 11/2010 | Ruben et al. |
| 7,842,467 | B1 | 11/2010 | Heidbrink et al. |
| 2002/0157122 | A1* | 10/2002 | Wong et al. ..................... 800/12 |
| 2009/0053243 | A1 | 2/2009 | Kurosawa et al. |
| 2010/0285017 | A1* | 11/2010 | Rohlff et al. ............... 424/135.1 |

FOREIGN PATENT DOCUMENTS

| EP | 1464709 A1 | 10/2004 |
| EP | 1498424 A2 | 1/2005 |
| EP | 1918299 A1 | 5/2008 |
| EP | 2133362 A1 | 12/2009 |
| EP | 2196474 A2 | 6/2010 |
| JP | 2005-147798 | 6/2005 |
| JP | 2006-317220 | 11/2006 |
| JP | 2007-186492 | 7/2007 |
| WO | 99/28462 A2 | 6/1999 |
| WO | 99/57132 A1 | 11/1999 |
| WO | 00/08158 A2 | 2/2000 |
| WO | 00/28032 A2 | 5/2000 |
| WO | 00/29435 A1 | 5/2000 |
| WO | 00/32776 A2 | 6/2000 |
| WO | 00/56889 A2 | 9/2000 |
| WO | 01/68848 A2 | 9/2001 |

(Continued)

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Alagaratnam, Sharmini et al., "TPD52, a candidate gene from genomic studies, is overexpressed in testicular germ cell tumours," Molecular and Cellular Endocrinology, vol. 306:75-80 (2009).
Allinen, Minna et al., "Analysis of IIq21-24 Loss of Heterozygosity Candidate Target Genes in Breast Cancer: Indications of TSLC1 Promoter Hypermethylation," Genes, Chromosomes & Cancer, vol. 34:384-389 (2002).
Ando, Kiyohiro et al., "Expression of TSLC1, a candidate tumor suppressor gene mapped to chromosome 11q23, is downregulated in unfavorable neuroblastoma without promoter hypermethylation," Int. J. Cancer, vol. 123:2087-2094 (2008).
Apostolidou, Sophia et al., "DNA methylation analysis in liquid-based cytology for cervical cancer screening," Int. J. Cancer, vol. 125:2995-3002 (2009).
Arase, Noriko et al., "Heterotypic interaction of CRTAM with Necl2 induces cell adhesion on activated NK cells and CD8+ T cells," International Immunology, vol. 17(9):1227-1237 (2005).

(Continued)

*Primary Examiner* — Maher Haddad
(74) *Attorney, Agent, or Firm* — Nelson Mullins Riley & Scarborough LLP; Jane E. Remillard, Esq.; Jill Gorny Sloper, Esq.

(57) ABSTRACT

The present disclosure provides isolated monoclonal antibodies, particularly human monoclonal antibodies, more particularly engineered antibodies resulting in increased binding to Fc receptors and/or increased potency for ADCC or immunoconjugates, which specifically bind to CADM1 with high affinity. Nucleic acid molecules encoding CADM1 antibodies, expression vectors, host cells and methods for expressing the CADM1 antibodies are also provided. Bispecific molecules and pharmaceutical compositions comprising the CADM1 antibodies are also provided. Methods for detecting CADM1, as well as methods for treating various cancers, including lung cancer and pancreatic cancer, are disclosed.

22 Claims, 29 Drawing Sheets

FOREIGN PATENT DOCUMENTS

| | | |
|---|---|---|
| WO | 02/14557 A1 | 2/2002 |
| WO | 02/18424 A2 | 3/2002 |
| WO | 02/066643 A2 | 8/2002 |
| WO | 2004/074320 A2 | 9/2004 |
| WO | 2005/012530 A2 | 2/2005 |
| WO | 2006/049854 A2 | 5/2006 |
| WO | 2006/090750 A1 | 8/2006 |
| WO | 2007/074832 A1 | 7/2007 |
| WO | 2008/007648 A1 | 1/2008 |
| WO | 2008/021290 A2 | 2/2008 |
| WO | 2008/053049 A1 | 5/2008 |
| WO | 2008/066655 A2 | 6/2008 |
| WO | WO/2008/026010 * | 6/2008 |
| WO | 2008/142693 A2 | 11/2008 |
| WO | 2008/143639 A2 | 11/2008 |
| WO | 2009/029883 A2 | 3/2009 |
| WO | 2009/040782 A2 | 4/2009 |
| WO | 2009/147549 A1 | 12/2009 |
| WO | 2010/088187 A1 | 8/2010 |
| WO | 2010/102175 A1 | 9/2010 |

OTHER PUBLICATIONS

Bax, Dorine A. et al., "Molecular and PHenotypic Characterisation of Paediatric Glioma Cell Lines as Models for Preclinical Drug Development," PLoS One, vol. 4(4):e5209, 9 pages (2009).

Berginc, Gasper et al., "MS-MLPA Reveals Progressive Age-Dependent Promoter Methylation of Tumor Suppressor Genes and Possible Role of IGSF4 Gene in Colorectal Carcinogenesis of Microsatellite Instable Tumors," Cancer Investigation, vol. 28:94-102 (2010).

Berkhout, Marloes et al., "Chromosomal and methylation alterations in sporadic and familial adenomatous polyposis-related duodenal carcinomas," Modern Pathology, vol. 20:1253-1262 (2007).

Bertolo, Cristina et al., "Differences and Molecular Immunohistochemical Perameters in the Subtypes of Infiltrating Ductal Breast Cancer," Am. J. Clin. Pathol., vol. 130:414-424 (2008).

Biederer, Thomas, "Bioinformatic characterization of the SynCAM family of immunoglobulin-like domain-containing adhesion molecules," Genomics, vol. 87:139-150 (2006).

Biederer, Thomas, "Progress from the Postsynaptic Side: Signaling in Synaptic Differentiation," Science's stke, vol. 274:pe9, 4 pages (2005).

Biederer, Thomas et al., "SynCAM, a Synaptic Adhesion Molecule That Drives Synapse Assembly," Science, vol. 297:1525-1531 (2002).

Bird, T.G. et al., "Activation of stem cells in hepatic diseases," Cell Tissue Res., vol. 331(1):283-300 (2008).

Boles, Kent S. et al., "The tumor suppressor TSLC1/NECL-2 triggers NK-cell and CD8+ T-cell responses through the cell-surface receptor CRTAM," Blood, vol. 106(3):779-786 (2005).

Breillat, Christelle et al., "Characterization of SynCAM surface trafficking using a SynCAM derived ligand with high homophilic binding affinity," Biochemical and Biophysical Research Communications, vol. 359:655-659 (2007).

Calin, George A. et al., "MiR-15a and miR-16-1 cluster functions in human leukemia," PNAS, vol. 105(13):5166-5171 (2008).

Chowers, Itay et al., "Identification of Novel Genes Preferentially Expressed in the Retina Using a Custom Human Retina cDNA Microarray," Investigative Ophthalmology & Visual Science, vol. 44(9):3732-3741 (2003).

Dewan, M. Zahidunnabi et al., "Critical Role for TSLC1 Expression in the Growth and Organ Infiltration of Adult T-Cell Leukemia Cells In Vivo," Journal of Virology, vol. 82(23):11958-11963 (2008).

Duenas-Gonzalez, Alfonso et al., "Epigenetics of cervical cancer. An overview and therapeutic perspectives," Molecular Cancer, vol. 4(38):doi:10.118611476-4598-4-38, 24 pages (2005).

Ehrlich, Melanie et al., "Quantitative analysis of associations between DNA hypermethylation, hypomethylation, and DNMT RNA levels in ovarian tumors," Oncogene, vol. 25(18):2636-2645 (2006).

Fogel, Adam I. et al., "SynCAMs Organize Synapses through Heterophilic Adhesion," The Journal of Neuroscience, vol. 27(46):12516-12530 (2007).

Fox, Michael A. et al., "Seeking long-term relationship: axon and target communicate to organize synaptic differentiation," Journal of Neurochemistry, vol. 97:1215-1231 (2006).

Fu, Li et al., "Frequent concomitant epigenetic silencing of the stress-responsive tumor suppressor gene CADM1, and its interacting partner DAL-1 in nasal NK/T-cell lymphoma," Int. J. Cancer, vol. 124:1572-1578 (2009).

Fujita, Eriko et al., "Distribution of RA175/TSLC1/SynCAM, a member of the immunoglobulin superfamily, in the developing nervous system," Developmental Brain Research, vol. 154:199-209 (2005).

Fujita, Eriko et al., "Loss of Partitioning-Defective-3/Isotype-Specific Interacting Protein (Par-3/ASIP) in the Elongating Spermatid of RA175 (IGSF4A/SynCAM)-Deficient Mice," The American Journal of Pathology, vol. 171 (6):1800-1810 (2007).

Fujita, Eriko et al., "Oligo-Astheno-Teratozoospermia in Mice Lacking RA175/TSLC1/SynCAM/IGSF4A, a Cell Adhesion Molecule in the Immunoglobulin Superfamily," Molecular and Cellular Biology, vol. 26(2):718-726 (2006).

Fujita, Eriko et al., "RA175, which is the mouse ortholog of TSLC1, a tumor suppressor gene in human lung cancer, is a cell adhesion molecule," Experimental Cell Research, vol. 287:57-66 (2003).

Fukami, Takeshi et al., "Identification of the Ts1c1 gene, a mouse orthologue of the human tumor suppressor TSLC1 gene," Gene, vol. 295:7-12 (2002).

Fukami, Takeshi et al., "Promoter methylation of the TSLC1 gene in advanced lung tumors and various cancer cell lines," Int. J. Cancer, vol. 107:53-59 (2003).

Fukuhara, Hiroshi et al., "Association of a lung tumor suppressor TSLC1 with MPP3, a human homologue of Drosophila tumor suppressor Dlg," Oncogene, vol. 22:6160-6165 (2003).

Fukuhara, Hiroshi et al., "Promoter Methylation of TSLC1 and Tumor Suppression by Its Gene Product in Human Prostate Cancer," Jpn. J. Cancer Res., vol. 93:605-609 (2002).

Furuno, Tadahide et al., "The Spermatogenic Ig Superfamily/Synaptic Cell Adhesion Molecule Mast-Cell Adhesion Molecule Promotes Interaction with Nerves," The Journal of Immunology, vol. 174:6934-6942 (2005).

Galibert, Laurent et al., "Nectin-like Protein 2 Defines a Subset of T-cell Zone Dendritic Cells and is a Ligand for Class-I-restricted T-cell-associated Molecule," The Journal of Biological Chemistry, vol. 280(23):21955-21964 (2005).

Gerrow, Kimberly et al., "Cell adhesion molecules at the synapse," Frontiers in Bioscience, vol. 11:2400-2419 (2006).

Giangreco, Adam et al., "Necl2 regulates epidermal adhesion and wound repair," Development, vol. 136:3505-3514 (2009).

Gomyo, Hiroki et al., "A 2-Mb Sequence-Ready Contig Map and a Novel Immunoglobulin Super-Family Gene IGSF4 in the LOH Region of Chromosome 11q23.2," Genomics, vol. 62:139-146 (1999).

Goto, Akiteru et al., "Loss of TSLC1 expression in lung adenocarcinoma: Relationships with histological subtypes, sex and prognostic significance," Cancer Sci., vol. 96(8):480-486 (2005).

Gustafson, Karen S. et al., "DNA Methylation Profiling of Cervical Squamous Intraepithelial Lesions using Liquid-Based Cytology Specimens," Cancer, vol. 102(4):259-268 (2004).

Hagiyama, Man et al. "Expression of a Soluble Isoform of Cell Adhesion Molecule 1 in the Brain and Its Involvement in Directional Neurite Outgrowth," The American Journal of Pathology, vol. 174(6):2278-2289 (2009).

Hasstedt, Sandra J. et al., "Cell adhesion molecule 1: a novel risk factor for venous thrombosis," Blood, vol. 114 (14):3084-3091 (2009).

Heller, G. et al., "Expression and methylation pattern of TSLC1 cascade genes in lung carcinomas," Oncogene, vol. 25:959-968 (2006).

Hellwinkel, Olaf J.C. et al., "Methylation of the TPEF- and PAX6-promoters is increased in early bladder cancer and in normal mucosa adjacent to pTa tumours," BJU International, vol. 101(6):753-757 (2007).

Hess, Corine J. et al., "Concurrent methylation of promoters from tumor associated genes predicts outcome in acute myeloid leukemia," Leukemia & Lymphoma, vol. 49(6):1132-1141 (2008).

Honda, Teiichiro et al., "Hypermethylation of the TSLC1 Gene Promoter in Primary Gastric Cancers and Gastric Cancer Cell Lines," Jpn. J. Cancer Res., vol. 93:857-860 (2002).

Hori, Roderick T., "The minimal Tumor Suppressor in Lung Cancer-1 promoter is restrained by an inhibitory region," Mol. Biol. Rep., vol. 37:1979-1985 (2010).

Houshmandi, S.S. et al., "Tumor suppressor in lung cancer-1 (TSLC1) functions as a glioma tumor suppressor," Neurology, vol. 67:1863-1866 (2006).

Hoy, Jennifer et al., "SynCAM1 recruits NMDA receptors via Protein 4.1B," Mol. Cell Neurosci., vol. 42(4):466-483 (2009).

Hui, Angela Bik-Yu et al., "Epigenetic Inactivation of TSLC1 Gene in Nasopharyngeal Carcinoma," Molecular Carcinogenesis, vol. 38:170-178 (2003).

Ito, Akihiko et al., "Contribution of the SgIGSF adhesion molecule to survival of cultured mast cells in vivo," Biochemical and Biophysical Research Communications, vol. 319:200-206 (2004).

Ito, Akihiko et al., "Direct Interaction Between Nerves and Mast Cells Mediated by the SgIGSF/SynCAM Adhesion Molecule," Journal of Pharmacological Sciences, vol. 102:1-5 (2006).

Zelano, Johan et al., "Down-Regulation of mRNAs for Synaptic Adhesion Molecules Neuroligin-2 and -3 and SynCAM1 in Spinal Motoneurons After Axotomy," The Journal of Comparatiave Neurology, vol. 503:308-318 (2007).

Zelano, Johan et al., "SynCAM1 Expression Correlates With Restoration of Central Synapses on Spinal Motoneurons After Two Different Models of Peripheral Nerve Injury," The Journal of Comparative Neurology, vol. 517:670-682 (2009).

Zhang, Jun et al., "DNA Methylation in Anal Intraepithelial Lesions and Anal Squamous Cell Carcinoma," Clin. Cancer Res., vol. 11(18):6544-6549 (2005).

Zhiling, Yu et al., "Mutations in the gene encoding CADM1 are associated with autism spectrum disorder," Biochemical and Biophysical Resesarch Communications, vol. 377:926-929 (2008).

Zhou, Liang et al., "Frequent Hypermethylation of RASSF1A and TSLC1, and High Viral Load of Epstein-Barr Virus DNA in Nasopharyngeal Carcinoma and Matched Tumor-Adjacent Tissues," Neoplasia, vol. 7(9):809-815 (2005).

Pike, Brian L. et al., "DNA methylation profiles in diffuse large B-cell lymphoma and their relationship to gene expression status," Leukemia, vol. 22(5):1035-1043 (2008).

Pletcher, Mathew T. et al., "Identification of tumor suppressor candidate genes by physical and sequence mapping of the TSLC1 region of human chromosome 11q23," Gene, vol. 273:181-189 (2001).

Qin, Li et al., "Effect of TSLC1 Gene on Proliferation, Invasion and Apoptosis of Human Hepatocellular Carcinoma Cell Line HepG2," Journal of Huazhong University of Science and Technology, vol. 27(5):535-537 (2007).

Qin, L. et al., "The growth inhibition effects of TSLC1 gene on human hepatocyte carcinoma cell line HepG2," Zhonghua Gan Zang Bing Za Zhi, vol. 15(7):509-512 (2007).

Reamon-Buettner, Stella Marie et al., "Epigenetic Silencing of Cell Adhesion Molecule 1 in Different Cancer Progenitor Cells of Transgenic c-Myc and c-Raf Mouse Lung Tumors," Cancer Res., vol. 68(18):7587-7596 (2008).

Rohrs, Sonja et al., "Hypomethylation and expression of BEX2, IGSF4 and TIMP3 indicative of MLL translocations in Acute Myeloid Leukemia," Molecular Cancer, vol. 8(83):doi:10.118611476-4598-8-86, pp. 1-11 (2009).

Royland, Joyce E. et al., "Gene expression profiles following exposure to a developmental neurotoxicant, Aroclor 1254: Pathway analysis for possible mode(s) of action," Toxicology and Applied Pharmacology, vol. 231:179-196 (2008).

Sara, Yildirim et al., "Selective Capability of SynCAM and Neuroligin for Functional Synapse Assembly," The Journal of Neuroscience, vol. 25(1):260-270 (2005).

Sasaki, Hidenori et al., "Overexpression of a cell adhesion molecule, TSLC1, as a possible molecular marker for acute-type adult T-cell leukemia," Blood, vol. 105:1204-1213 (2005).

Sasaki, Shin et al., "DNA mehtylation and sensitivity to antimetabolites in cancer cell lines," Oncology Reports, vol. 19:407-412 (2008).

Shimizu, Kyoko et al., "Aberrant DNA methylation of the 5' upstream region of Tslc1 gene in hamster pancreatic tumors," Biochemical and Biophysical Research Communications, vol. 353:522-526 (2007).

Shimizu, Kyoko et al., "Reduced expression of the Tslc1 gene and its aberrant DNA methylation in rat lung tumors," Biochemical and Biophysical Research Communications, vol. 347:358-362 (2006).

Shingai, Tatsushi et al., "Implications of Nectin-like Molecule-2/IGSF4/RA175/SgIGSF/TSLC1/SynCAM1 in Cell-Cell Adhesion and Transmembrane Protein Localization in Epithelial Cells," The Journal of Biological Chemistry, vol. 278 (37):35421-35427 (2003).

Soejima, Kenzo et al., "DNA methyltransferase 3b contributes to oncogenic transformation induced by SV4OT antigen and activated Ras," Oncogene, vol. 22:4723-4733 (2003).

Steenbergen, Renske D.M. et al., "HPV-mediated transformation of the anogenital tract," Journal of Clinical Virology, vol. 32S:S25-S33 (2005).

Steenbergen, Renske D.M. et al., "TSLC1 Gene Silencing in Cervical Cancer Cell Lines and Cervical Neoplasia," Journal of the National Cancer Institute, vol. 96(4):294-305 (2004).

Stephen, Josena K. et al., "DNA hypermethylation profiles in squamous cell carcinoma of the vulva," Int. J. Gynecol. Pathol., vol. 28(1):63-75 (2009).

Suckow, Arthur T. et al., "Expression of Neurexin, Neuroligin, and Their Cytoplasmic Binding Partners in the Pancreatic beta-Cells and the Involvement of Neuroligin in Insulin Secretion," Endocrinology, vol. 149(12):6006-6017 (2008).

Surace, Ezequiel I. et al., "Loss of Tumor Suppressor in Lung Cancer-1 (TSLC1) Expression in Meningioma Correlates with Increased Malignancy Grade and Reduced Patient Survival," Journal of Neuropathology and Experimental Neurology, vol. 63(10):1015-1027 (2004).

Surace, Ezequiel I. et al., "Tslc1 (Nectin-Like Molecule-2) Is Essential for Spermatozoa Motility and Male Fertility," J. Androl., vol. 27(6):816-825 (2006).

Tamura, Gen, "Alterations of tumor suppressor and tumor-related genes in the development and progression of gastric cancer," World Journal of Gastroenterology, vol. 12(2):192-198 (2006).

Tamura, G., "Promoter methylation status of tumor suppressor and tumor-related genes in neoplastic and non-neoplastic gastric epithelia," Histol. Histopathol., vol. 19:221-228 (2004).

Tanabe, Yuko et al., "Brain proteins with PDZ domains associated with RA175/SynCAM," Abstracts/Neuroscience Research, vol. 58S:S239, Abstract No. P3-j34 (2007).

Tanabe, Yuko et al., "Neuronal RA175/SynCAM1 isoforms are processed by tumor necrosis factor-alpha-converting enzyme (TACE)/ADAM17-like proteases," Neuroscience Letters, vol. 444:16-21 (2008).

Terada, Nobuo et al., "Involvement of a membrane skeletal protein, 4.1G, for Sertoli/germ cell interaction," Reproduction, vol. 139:883-892 (2010).

Thivolet, J. et al., "Cells in the epidermotropic lymphomas (mycosis fungoides and Sezary syndrome. Study using monoclonal antibodies," Nouv. Presse Med., vol. 11(41):3033-3038 (1982).

Thomas, Lisa A. et al., "Expression and Adhesion Profiles of SynCAM Adhesion Molecules Indicate Distinct Neuronal Functions," J. Comp. Neurol., vol. 510(1):47-67 (2008).

Triana-Baltzer, Gallen B. et al., "Multiple Cell Adhesion Molecules Shaping a Complex Nicotinic Synapse on Neurons," Mol. Cell Neurosci., vol. 39(1):74-82 (2008).

Tsujiuchi, Toshifumi et al., "Expression and DNA methylation patterns of Tslc1 and Dal-1 genes in hepatocellular carcinomas induced by N-nitrosodiethylamine in rats," Cancer Sci., vol. 98(7):943-948 (2007).

Tsukioka, Fusae et al., "Expression and Localization of the Cell Adhesion Molecule SgIGSF during Regeneration of the Olfactory Epithelium in Mice," Acta Histochem. Cytochem., vol. 40(2):43-52 (2007).

Uchino, Kazuya et al., "Clinical Implication and Prognostic Significance of the Tumor Suppressor TSLC1 Gene Detected in Adenocarcinoma of the Lung," Cancer, vol. 98:1002-1007 (2003).

Urase, Koko et al., "Expression of RA175 mRNA, a new member of the immunoglobulin superfamily, in developing mouse brain," NeuroReport, vol. 12(15):3217-3221 (2001).

Usami, Yu et al., "Tumor suppressor in lung cancer-1 as a novel ameloblast adhesion molecule and its downregulation in ameloblastoma," Pathology International, vol. 57:68-75 (2007).

Van Der Weyden, Louise et al., "Loss of TSLC1 Causes Male Infertility Due to a Defect at the Spermatid Stage of Spermatogenesis," Molecular and Cellular Biology, vol. 26(9):3595-3609 (2006).

Wakayama, Tomohiko et al., "Cloning and Characterization of a Novel Mouse Immunoglobulin Superfamily Gene Expressed in Early Spermatogenic Cells," Molecular Reproduction and Development, vol. 60:158-164 (2001).

Wakayama, Tomohiko et al., "Expression and Functional Characterization of the Adhesion Molecule Spermatogenic Immunoglobulin Superfamily in the Mouse Testis," Biology of Reproduction, vol. 68:1755-1763 (2003).

Wakayama, Tomohiko et al., "Heterophilic Binding of the Adhesion Molecules Poliovirus Receptor and Immunoglobulin Superfamily 4A in the Interaction Between Mouse Spermatogenic and Sertoli Cells," Biology of Reproduction, vol. 76:1081-1090 (2007).

Wakayama, Tomohiko et al., "Role of the spermatogenic-Sertoli cell interaction through cell adhesion molecule-1 (CADM1) in spermatogenesis," Anat. Sci. Int., vol. 84:112-121 (2009).

Wang, Chang Yi et al., "Preparation and Characterization of Monoclonal Antibodies Recognizing Three Distinct Differentiation Antigens (BL1, BL2, BL3) on Human B Lymphocytes," The Journal of Immunology, vol. 133(2):684-691 (1984).

Watabe, Kenji et al., "Distinct roles for the SgIGSF adhesion molecule and c-kit receptor tyrosine kinase in the interaction between mast cells and the mesentery," Biochemical and Biophysical Research Communications, vol. 324:782-788 (2004).

Watabe, K. et al., "IGSF4: a new intercelluar adhesion molecule that is called by three names, TSLC1, SgIGSF and SynCAM, by virtue of its diverse function," Histol. Histopathol., vol. 18:1321-1329 (2003).

Williams, YN et al., "Cell adhesion and prostate tumor-suppressor activity of TSLL2/IGSF4C, an immunoglobulin superfamily molecule homologous to TSLC1/IGSF4," Oncogene, vol. 25:1446-1453 (2006).

Wilting, Saskia M. et al., "Chromosomal Signatures of a Subset of High-Grade Premalignant Cervical Lesions Closely Resemble Invasive Carcinomas," Cancer Res., vol. 69(2):647-655 (2009).

Worsham, Maria J. et al., "Epigenetic Events of Disease Progression in Head and Neck Squamous Cell Carcinoma," Arch Otolaryngol Head Neck Surg., vol. 132:668-677 (2006).

Yageta, Mika et al., "Direct Association of TSLC1 and DAL-1, Two Distinct Tumor Suppressor Proteins in Lung Cancer," Cancer Research, vol. 62:5129-5133 (2002).

Yamada, Daisuke et al., "Disruption of Spermatogenic Cell Adhesion and Male Infertility in Mice Lacking TSLC1/IGSF4, an Immunoglobulin Superfamily Cell Adhesion Molecule," Molecular and Cellular Biology, vol. 26(9):3610-3624 (2006).

Yamagata, Masahito et al., "Synaptic adhesion molecules," Current Opinion in Cell Biology, vol. 15:621-632 (2003).

Yang, Weidong et al., "Human Lung Mast Cells Adhere to Human Airway Smooth Muscle, in Part, via Tumor Suppressor in Lung Cancer-1," The Journal of Immunology, vol. 176:1238-1243 (2006).

Yang, Y.-X. et al., "Involvement of tumor suppressor in lung cancer 1 gene expression in cervical carcinogenesis," Int. J. Gynecol. Cancer, vol. 16:1868-1872 (2006).

Zelano, Johan et al., "Altered expression of nectin-like adhesion molecules in the peripheral nerve after sciatic nerve transection," Neuroscience Letters, vol. 449:28-33 (2009).

Ito, Akihiko et al., "Expression of cell adhesion molecule 1 in malignant pleural mesothelioma as a cause of efficient adhesion and growth on mesothelium," Laboratory Investigation, vol. 88:504-514 (2008).

Ito, Akihiko et al., "Expression of the TSLC1 Adhesion Molecule in Pulmonary Epithelium and Its Down-Regulation in Pulmonary Adenocarcinoma Other than Bronchioloalveolar Carcinoma," Laboratory Investigation, vol. 83 (8):1175-1183 (2003).

Ito, Akihiko et al., "Involvement of the SgIGSF/Necl-2 adhesion molecule in degranulation of mesenteric mast cells," Journal of Neuroimmunology, vol. 184:209-213 (2007).

Ito, Akihiko et al., "Nerve-mast cell and smooth muscle-mast cell interaction mediated by cell adhesion molecule-1, CADM1," J. Smooth Muscle Res., vol. 44(2):83-93 (2008).

Ito, Akihiko et al., "SgIGSF: a new mast-cell adhesion molecule used for attachment to fibroblasts and transcriptionally regulated by MITF," Blood, vol. 101(7):2601-2608 (2003).

Ito, Akihiko et al., "SgIGSF Is a Novel Biliary-Epithelial Cell Adhesion Molecule Mediating Duct/Ductule Development," Hepatology, vol. 45:684-694 (2007).

Ito, Tetsuo et al., "Involvement of TSLC1 in Progression of Esophageal Squamous Cell Carcinoma," Cancer Research, vol. 63:6320-6326 (2003).

Jansen, Marnix et al., "Aberrant Methylation of the 5' CpG Island of TSLC1 Is Common in Pancreatic Ductal Adenocarcinoma and Is First Manifest in High-Grade PanINs," Cancer Biology & Therapy, vol. 1(3):293-296 (2002).

Kahn, Steven L. et al., "Quantitative Methylation-specific PCR for the Detection of Aberrant DNA Methylation in Liquid-based Pap Tests," Cancer, vol. 114(1):57-64 (2008).

Kakunaga, Shigeki et al., "Nectin-like molecule-1/TSLL1/SynCAM3: a neural tissue-specific immunoglobulin-like cell-cell adhesion molecule localizing at non-junctional contact sites of presynaptic nerve terminals, axons and glia cell processes," Journal of Cell Sciences, vol. 118:1267-1277 (2005).

Kanduri, Meena et al., "Differential genome-wide array-based methylation profiles in prognostic subsets of chronic lymphocytic leukemia," Blood, vol. 115(2):296-305 (2010).

Kawano, Satoshi et al., "Silencing of ErbB3/ErbB2 Signaling by Immunoglobulin-like Necl-2," Journal of Biological Chemistry, vol. 284(35):23793-23805 (2009).

Kijanka, G. et al., "Human IgG antibody profiles differentiate between symptomatic patients with and without colorectal cancer," Gut, vol. 59:69-78 (2010).

Kikuchi, Shinji et al., "Hypermethylation of the TSLC1/IGSF4 Promoter Is Associated with Tobacco Smoking and a Poor Prognosis in Primary Nonsmall Cell Lung Carcinoma," Cancer, vol. 106:1751-1758 (2006).

Kikuchi, Shinji et al., "Promoter Methylation of DAL-1/4.1B Predicts Poor Prognosis in Non-Small Cell Lung Cancer," Clin. Cancer Res., vol. 11(8):2954-2961 (2005).

Kitamura, Yukihiko, "MITF and SgIGSF: an essential transcription factor and its target adhesion molecule for development and survival of mast cells," Mast Cells and Basophils: Development, Activation and Roles in Allergic/Autoimmune Disease: Novartis Foundation Symposium, vol. 271:4-14 (2005).

Knowles, Daniel M. II et al., "A New Human B-Lymphocyte Surface Antigen (BL-2) Detectable by a Hybridoma Monoclonal Antibody: Distribution on Benign and Malignant Lymphoid Cells," Blood, vol. 62(1):191-199 (1983).

Koma, Yu-Ichiro et al., "Cell Adhesion Molecule 1 Is a Novel Pancreatic-Islet Cell Adhesion Molecule That Mediates Nerve-Islet Cell Interactions," Gastroenterology, vol. 134:1544-1554 (2008).

Korkola, J.E. et al., "In Vivo differentiation and Genomic Evolution in Adult Male Germ Cell Tumors," Genes, Chromosomes & Cancer, vol. 47:43-55 (2008).

Kuramochi, Masami et al., "TSLC1 is a tumor-suppressor gene in human non-small-cell lung cancer," Nature Genetics, vol. 27:427-430 (2001).

Li, Jianduan et al., "IGSF4 promoter methylation and expression silencing in human cervical cancer," Gynecologic Oncology, vol. 96:150-158 (2005).

Li, M. et al., "The study on methylation of gene IGSF4 promoter in acute leukemia cells," Zhongguo Shi Yan Xue Ye Xue Za Zhi, vol. 12(2):125-127 (2004).

Lindsey, Janet et al., "Identification of tumour-specific epigenetic events in medulloblastoma development by hypermethylation profiling," Carcinogenesis, vol. 25(5):661-668 (2004).

Lung, Hong Lok et al., "Fine Mapping of the 11Q22-23 Tumor Suppressive Region and Involvement of TSLC1 in Nasopharyngeal Carcinoma," Int. J. Cancer, vol. 112:628-635 (2004).

Lung, Hong Lok et al., "TSLC1 Is a Tumor Suppressor Gene Associated with Metastasis in Nasopharyngeal Carcinoma," Cancer Res., vol. 66(19):9385-9392 (2006).

Lusis, Eriks et al., "Meningioma: an update," Current Opinion in Neurology, vol. 17:687-692 (2004).

Lyckman, Alvin W. et al., "Gene expression patterns in visual cortex during the critical period: Synaptic stabilization and reversal by visual deprivation," PNAS, vol. 105(27):9409-9414 (2008).

Mao, Xinliang et al., "Re-expression of TSLC1 in a non-small-cell lung cancer cell line induces apoptosis and inhibits tumor growth," Oncogene, vol. 23:5632-5642 (2004).

Mao, Xinliang et al., "The Cytoplasmic Domain Is Critical to the Tumor Suppressor Activity of TSLC1 in Non-Small Cell Lung Cancer," Cancer Research, vol. 63:7979-7985 (2003).

Masuda, Mari et al., "CADM1 Interacts with Tiam1 and Promotes Invasive Phenotype of Human T-cell Leukemia Virus Type I-transformed Cells and Adult T-cell Leukemia Cells," The Journal of Biological Chemistry, vol. 285 (20):15511-15522 (2010).

Masuda, Mari et al., "The Tumor Suppressor Protein TSLC1 Is Involved in Cell-Cell Adhesion," The Journal of Biological Chemistry, vol. 277(34):31014-31019 (2002).

Masuda, Mari et al., "Tumor Suppressor in Lung Cancer (TSLC)1 Suppresses Epithelial Cell Scattering and Tubulogenesis," The Journal of Biological Chemistry, vol. 280(51):42164-42171 (2005).

Maurel, Patrice et al., "Nectin-like proteins mediate axon-Schwann cell interactions along the internode and are essential for myelination," The Journal of Cell Biology, vol. 178(5):861-874 (2007).

Michels, Evi et al., "CADM1 is a strong neuroblastoma candidate gene that maps within a 3.72 Mb critical region of loss on 11q23," BMC Cancer, vol. 8(173):doi:10.1186/1471-2407-8-173, 9 pages (2008).

Missler, Markus, "Synaptic cell adhesion goes functional," Trends in Neurosciences, vol. 26(4):176-178 (2003).

Momoi, Takashi et al., "Genetic factors and epigenetic factors for autism: endoplasmic reticulum stress and impaired synaptic function," Cell Biol. Int., vol. 34:13-19 (2010).

Morii, Eiichi et al., "Number of Mast Cells in the Peritoneal Cavity of Mice, Influence of Microphthalmia Transcription Factor through Transcription of Newly Found Mast Cell Adhesion Molecule, Spermatogenic Immunoglobulin Superfamily," American Journal of Pathology, vol. 165(2):491-499 (2004).

Murakami, Yoshinori, "Functional cloning of a tumor suppressor gene, TSLC1, in human non-small cell lung cancer," Oncogene, vol. 21:6936-6948 (2002).

Murakami, Yoshinori, "Involvement of a cell adhesion molecule, TSLC1/IGSF4, in human oncogenesis," Cancer Sci., vol. 96(9):543-552 (2005).

Murakami, Yoshinori, "Involvement of a Tumor Suppressor TSLC1/CADM1 in Lung Tumorigenesis in Human and the Gene-deficient Mice," Journal of Thoracic Oncology, vol. 2(8, Suppl. 4):S376, Poster Presentation No. C6-03 (2007).

Murakami, Yoshinori, "Involvement of a Tumor Suppressor Protein CADM1/TSLC1 in Human Non-small Cell Lung Cancer," Haigan, vol. 49(6):910-916 (2009).

Nakanishi, Mamoru et al., "Molecular Basis of Neuroimmune Interaction in an in Vitro Coculture Approach," Cellular & Molecular Immunology, vol. 5(4):249-259 (2008).

Nam, Christine I. et al., "Postsynaptic assembly induced by neurexin-neuroligin interaction and neurotransmitter," PNAS, vol. 102(17):6137-6142 (2005).

Nowacki, S. et al. "Expression of the tumour suppressor gene CADM1 is associated with favourable outcome and inhibits in cell survival in neuroblastoma," Oncogene, vol. 27:3329-3338 (2008).

Ochiai, H. et al., "Bmi1 is a MYCN target gene that regulates tumorigenesis through repression of K1F1Bbeta and TSLC1 in neuroblastoma," Oncogene, vol. 29:2681-2690 (2010).

Ohta, Yoshimi et al., "Spatiotemporal patterns of expression of IGSF4 in developing mouse nervous sytem," Developmental Brain Research, vol. 156:23-31 (2005).

Overmeer, RM et al., "Association between dense CADM1 promoter methylation and reduced protein expression in high-grade CIN and cervical SCC," Journal of Pathology, vol. 215:388-397 (2008).

Patino-Lopez, Genaro et al., "Human class-I restricted T cell associated molecule is highly expressed in the cerebellum and is a marker for activated NKT and CD8+ T lymphocytes," Journal of Neuroimmunology, vol. 171:145-155 (2006).

Paulsson, Kajsa et al., "Methylation of tumour suppressor gene promoters in the presence and absence of transcriptional silencing in high hyperdiploid acute lymphoblastic leukaemia," British Journal of Haematology, vol. 144:838-847 (2008).

Pietri, Thomas et al., "Six cadm/SynCAM Genes Are Expressed in the Nervous System of Developing Zabrafish," Developmental Dynamics, vol. 237:233-246 (2008).

Kitamura, Yuka et al., "Frequent overexpression of CADM1/IGSF4 in lung adenocarcinoma," Biochemical and Biophysical Research Communications, vol. 383:480-484 (2009).

Sussan, Thomas E. et al., "Tumor suppressor in lung cancer I (TSLCI) alters tumorigenic growth properties and gene expression," Molecular Cancer, vol. 4:28 doi:10.1186/1476-4598-4-28 (2005).

International Preliminary Report on Patentability, International Search Report and Written Opinion for Application No. PCT/US2010/026315, dated Jun. 4, 2010.

International Preliminary Report of Patentability and Written Opinion for Application No. PCT/US2010/026315, dated Sep. 6, 2011.

\* cited by examiner

Anti- CADM1 PTA021_A1 VH

V segment:   2-05
D segment:   6-6
J segment:   JH5b

```
       Q   I   T   L   K   E   S   G   P   T   L   V   K   P   T   Q   T   L
  1  CAG ATC ACC TTG AAG GAG TCT GGT CCT ACG CTG GTG AAA CCC ACA CAG ACC CTC

CDR1
                                                              ~~~~~~~~~~~~~~~~~~~~~~
       T   L   T   C   T   F   S   G   F   S   L   N   T   S   G   V   G   V
 55  ACG CTG ACC TGC ACC TTC TCT GGG TTC TCA CTC AAT ACT AGT GGA GTG GGT GTG

CDR1                                                       CDR2
     ~~~                                                     ~~~~~~~~~~
       G   W   I   R   Q   P   P   G   K   A   L   E   W   L   A   L   I   Y
109  GGC TGG ATC CGT CAG CCC CCA GGA AAG GCC CTG GAG TGG CTT GCA CTC ATT TAT

CDR2
     ~~~~~~~~~~~~~~~~~~~~~~~~~~~~~~~~~~~~~~~~~~~~~~~~
       W   D   D   D   K   R   Y   S   P   S   L   K   S   R   L   T   I   T
163  TGG GAC GAT GAT AAG CGC TAC AGC CCA TCT CTG AAG AGC AGG CTC ACC ATC ACC

K   D   T   S   K   N   Q   V   V   L   T   M   T   N   M   D   P   V
217  AAG GAC ACC TCC AAA AAC CAG GTG GTC CTT ACA ATG ACC AAC ATG GAC CCT GTG

CDR3
                                                 ~~~~~~~~~~~~~~~~~~~~~~~~~~~~~~~~~~~~~~~~
       D   T   A   T   Y   Y   C   A   H   R   R   V   E   W   V   A   L   A
271  GAC ACA GCC ACA TAT TAC TGT GCA CAC AGG AGA GTT GAA TGG GTC GCC CTG GCA

CDR3
     ~~~~~~~~~~~~~~~~~~~~~
       G   N   W   F   D   P   W   G   Q   G   T   L   V   T   V   S   S
325  GGG AAC TGG TTC GAC CCC TGG GGC CAG GGA ACC CTG GTC ACC GTC TCC TCA
```

FIGURE 1A

Anti-CADM1 PTA021_A1 VK

```
V segment:      L15
J segment:      JK4
```

```
        D   I   Q   M   T   Q   S   P   S   S   L   S   A   S   V   G   D   R
  1   GAC ATC CAG ATG ACC CAG TCT CCA TCC TCA CTG TCT GCA TCT GTA GGA GAC AGA
                                              CDR1
                                      ~~~~~~~~~~~~~~~~~~~~~~~~~~~~~~~~~~~~~~~~
        V   T   I   T   C   R   A   S   Q   G   I   S   S   W   L   A   W   Y
 55   GTC ACC ATC ACT TGT CGG GCG AGT CAG GGT ATT AGC AGC TGG TTA GCC TGG TAT
                                                                      CDR2
                                                              ~~~~~~~~~~~~~~~~~~~~
        Q   Q   K   P   E   K   A   P   K   S   L   I   Y   G   A   S   S   L
109   CAG CAG AAA CCA GAG AAA GCC CCT AAG TCC CTG ATC TAT GGT GCA TCC AGT TTG

CDR2
      ~~~~~~~
        Q   S   G   V   P   S   R   F   S   G   S   G   S   G   T   D   F   T
163   CAA AGT GGG GTC CCA TCA AGG TTC AGC GGC AGT GGA TCT GGG ACA GAT TTC ACT
                                                                      CDR3
                                                                      ~~~~~~~
        L   T   I   S   N   L   Q   P   E   D   F   A   T   Y   Y   C   Q   Q
217   CTC ACC ATC AGC AAC CTG CAG CCT GAA GAT TTT GCA ACT TAT TAC TGC CAA CAG

CDR3
      ~~~~~~~~~~~~~~~~~~~~~~~~~~~
        Y   N   S   Y   P   L   T   F   G   G   G   T   K   V   E   I   K
271   TAT AAT AGT TAC CCT CTC ACT TTC GGC GGA GGG ACC AAG GTG GAG ATC AAA
```

FIGURE 1B

Anti-CADM1 PTA021_A2 VH

```
V segment:    2-05
D segment:    6-6
J segment:    JH5b
```

```
        Q   I   T   L   K   E   S   G   P   T   L   V   K   P   T   Q   T   L
  1   CAG ATC ACC TTG AAG GAG TCT GGT CCT ACG CTG GTG AAA CCC ACA CAG ACC CTC

CDR1
                                                              ~~~~~~~~~~~~~~~~~~~~~~
        T   L   T   C   T   F   S   G   F   S   L   S   T   S   G   V   G   V
 55   ACG CTG ACC TGC ACC TTC TCT GGG TTC TCA CTC AGC ACT AGT GGA GTG GGT GTG

CDR1                                                          CDR2
      ~~~                                                           ~~~~~~~~~~~
        G   W   I   R   Q   P   P   G   K   A   L   E   W   L   A   L   I   Y
109   GGC TGG ATC CGT CAG CCC CCA GGA AAG GCC CTG GAG TGG CTT GCA CTC ATT TAT

CDR2
      ~~~~~~~~~~~~~~~~~~~~~~~~~~~~~~~~~~~~~~~~~~~~~~~~~~~~
        W   D   D   D   K   R   Y   S   P   S   L   K   S   R   L   T   I   T
163   TGG GAT GAT GAT AAG CGC TAC AGC CCA TCT CTG AAG AGC AGG CTC ACC ATC ACC

K   D   T   S   K   N   Q   V   V   L   T   M   T   N   M   D   P   V
217   AAG GAC ACC TCC AAA AAC CAG GTG GTC CTT ACA ATG ACC AAC ATG GAC CCT GTG

CDR3
                                                              ~~~~~~~~~~~~~~~~~~~~~~~~~~~~~~~~~~~~~~
        D   T   A   I   Y   Y   C   A   H   R   R   V   E   W   F   A   L   A
271   GAC ACA GCC ATA TAT TAC TGT GCG CAC AGG AGA GTT GAG TGG TTC GCC CTG GCA

CDR3
      ~~~~~~~~~~~~~~~~~~~~~~~~~
        G   N   W   F   D   P   W   G   Q   G   S   L   V   T   V   S   S
325   GGG AAC TGG TTC GAC CCC TGG GGC CAG GGA TCC CTG GTC ACC GTC TCC TCA
```

FIGURE 2A

Anti-CADM1 PTA021_A2 VK

```
V segment:    L15
J segment:    JK4
```

```
       D   I   Q   M   T   Q   S   P   S   S   L   S   A   S   V   G   D   R
  1  GAC ATC CAG ATG ACC CAG TCT CCA TCC TCA CTG TCT GCA TCT GTA GGA GAC AGA

CDR1
                         ~~~~~~~~~~~~~~~~~~~~~~~~~~~~~~~~~~~~~~~~~~~~~~
       V   T   I   T   C   R   A   S   Q   G   I   S   S   W   L   A   W   Y
 55  GTC ACC ATC ACT TGT CGG GCG AGT CAG GGT ATT AGC AGC TGG TTA GCC TGG TAT

CDR2
                                                    ~~~~~~~~~~~~~~~~~~~~~~
       Q   Q   K   P   E   K   A   P   K   S   L   I   Y   A   A   S   S   L
109  CAG CAG AAA CCA GAG AAA GCC CCT AAG TCC CTG ATC TAT GCT GCA TCC AGT TTG

CDR2
     ~~~~~~~
       Q   S   G   V   P   S   R   F   S   G   S   G   S   G   T   D   F   T
163  CAA AGT GGG GTC CCA TCA AGG TTC AGC GGC AGT GGA TCT GGG ACA GAT TTC ACT

CDR3
                                                                    ~~~~~~~
       L   T   I   S   S   L   Q   P   E   D   F   A   T   Y   Y   C   Q   Q
217  CTC ACC ATC AGC AGC CTG CAG CCT GAA GAT TTT GCA ACT TAT TAC TGC CAA CAG

CDR3
     ~~~~~~~~~~~~~~~~~~~~~~~~~~~
       Y   N   S   Y   P   L   T   F   G   G   G   T   K   V   E   I   K
271  TAT AAT AGT TAC CCT CTC ACT TTC GGC GGA GGG ACC AAG GTG GAG ATC AAA
```

FIGURE 2B

Anti- CADM1 PTA021_A3 VH

V segment:    2-05
    D segment:    6-6
    J segment:    JH5b

```
      Q   I   T   L   K   E   S   G   P   T   L   V   K   P   T   Q   T   L
  1 CAG ATC ACC TTG AAG GAG TCT GGT CCT ACG CTG GTG AAA CCC ACA CAG ACC CTC
                                                                       CDR1
                                                                       ~~~~~~~~~~~~~~~~~~~~~
      T   L   T   C   T   F   S   G   F   S   L   S   T   S   G   V   G   V
 55 ACG CTG ACC TGC ACC TTC TCT GGG TTC TCA CTC AGT ACT AGT GGA GTG GGT GTG
    CDR1                                                            CDR2
    ~~~                                                             ~~~~~~~~~~~
      G   W   I   R   Q   P   P   G   K   A   L   E   W   L   A   L   I   Y
109 GGC TGG ATC CGT CAG CCC CCA GGA AAG GCC CTG GAG TGG CTT GCA CTC ATT TAT
                    CDR2
                    ~~~~~~~~~~~~~~~~~~~~~~~~~~~~~~~~~~~~~~~~~~~~~~~~~~~
      W   D   D   D   K   R   Y   S   P   S   L   K   S   R   L   T   I   T
163 TGG GAC GAT GAT AAG CGC TAC AGC CCA TCT CTG AAG AGC AGG CTC ACC ATC ACC

K   D   T   S   K   N   Q   V   V   L   T   M   T   N   M   D   P   V
217 AAG GAC ACC TCC AAA AAC CAG GTG GTC CTT ACA ATG ACC AAC ATG GAC CCT GTG
                                                        CDR3
                                                        ~~~~~~~~~~~~~~~~~~~~~~~~~~~~~~~~~~~~~~~~
      D   T   A   T   Y   Y   C   A   H   R   R   V   E   W   V   T   L   A
271 GAC ACA GCC ACA TAT TAC TGT GCA CAC AGG AGA GTT GAG TGG GTC ACC CTG GCA
    CDR3
    ~~~~~~~~~~~~~~~~~~~~~~~~~
      G   N   W   F   D   P   W   G   Q   G   T   L   V   T   V   S   S
325 GGG AAC TGG TTC GAC CCC TGG GGC CAG GGA ACC CTG GTC ACC GTC TCC TCA
```

FIGURE 3A

Anti- CADM1 PTA021_A3 VK

```
V segment:    L15
J segment:    JK4
```

```
      D   I   Q   M   T   Q   S   P   S   S   L   S   A   S   V   G   D   R
  1 GAC ATC CAG ATG ACC CAG TCT CCA TCC TCA CTG TCT GCA TCT GTA GGA GAC AGA

CDR1
                       ~~~~~~~~~~~~~~~~~~~~~~~~~~~~~~~~~~~~~~~~~~~
      V   T   I   T   C   R   A   S   Q   G   I   S   S   W   L   A   W   Y
 55 GTC ACC ATC ACT TGT CGG GCG AGT CAG GGT ATT AGC AGC TGG TTA GCC TGG TAT

CDR2
                                                ~~~~~~~~~~~~~~~~~~~~
      Q   Q   K   P   E   K   A   P   K   S   L   I   Y   A   A   S   S   L
109 CAG CAG AAA CCA GAG AAA GCC CCT AAG TCC CTG ATC TAT GCT GCA TCC AGT TTG

CDR2
      ~~~~~~~
      Q   S   G   V   P   S   R   F   S   G   S   G   S   G   T   D   F   T
163 CAA AGT GGG GTC CCA TCA AGG TTC AGC GGC AGT GGA TCT GGG ACA GAT TTC ACT

CDR3
                                                                   ~~~~~~~
      L   T   I   S   N   L   Q   P   E   D   F   A   T   Y   Y   C   Q   Q
217 CTC ACC ATC AGC AAC CTG CAG CCT GAA GAT TTT GCA ACT TAT TAC TGC CAA CAG

CDR3
      ~~~~~~~~~~~~~~~~~~~~~~~~~~~
      Y   N   S   Y   P   L   T   F   G   G   G   T   K   V   E   I   K
271 TAT AAT AGT TAC CCT CTC ACT TTC GGC GGA GGG ACC AAG GTG GAG ATC AAA
```

FIGURE 3B

Anti- CADM1 PTA021_A1 VH

| | |
|---|---|
| 2-05 germline | Q I T L K E S G P T L V K P T Q T L |
| PTA021_A1 VH  | - - - - - - - - - - - - - - - - - - |

_CDR1_____

| | |
|---|---|
| 2-05 germline | T L T C T F S G F S L S T S G V G V |
| PTA021_A1 VH  | - - - - - - - - - - - N - - - - - - |

_                            _CDR2

| | |
|---|---|
| 2-05 germline | G W I R Q P P G K A L E W L A L I Y |
| PTA021_A1 VH  | - - - - - - - - - - - - - - - - - - |

CDR2_____

| | |
|---|---|
| 2-05 germline | W N D D K R Y S P S L K S R L T I T |
| PTA021_A1 VH  | - D - - - - - - - - - - - - - - - - |

| | |
|---|---|
| 2-05 germline | K D T S K N Q V V L T M T N M D P V |
| PTA021_A1 VH  | - - - - - - - - - - - - - - - - - - |

_CDR3_____

| | |
|---|---|
| 2-05 germline | D T A T Y Y C A H R |
| PTA021_A1 VH  | - - - - - - - - - - R V E W V A L A |

| | |
|---|---|
| JH5b germline |   N W F D P W G Q G T L V T V S S |
| PTA021_A1 VH  | G - - - - - - - - - - - - - - - - |

FIGURE 4

Anti- CADM1 PTA021_A2 VH

| | | |
|---|---|---|
| 2-05 germline | Q I T L K E S G P T L V K P T Q T L |
| PTA021_A2 VH | - - - - - - - - - - - - - - - - - - |

_CDR1_

| | |
|---|---|
| 2-05 germline | T L T C T F S G F S L S T S G V G V |
| PTA021_A2 VH | - - - - - - - - - - - - - - - - - - |

_CDR2_

| | |
|---|---|
| 2-05 germline | G W I R Q P P G K A L E W L A L I Y |
| PTA021_A2 VH | - - - - - - - - - - - - - - - - - - |

CDR2

| | |
|---|---|
| 2-05 germline | W N D D K R Y S P S L K S R L T I T |
| PTA021_A2 VH | - D - - - - - - - - - - - - - - - - |

| | |
|---|---|
| 2-05 germline | K D T S K N Q V V L T M T N M D P V |
| PTA021_A2 VH | - - - - - - - - - - - - - - - - - - |

_CDR3_

| | |
|---|---|
| 2-05 germline | D T A T Y Y C A H R |
| PTA021_A2 VH | - - - I - - - - - - R V E W F A L A |

__CDR3__

| | |
|---|---|
| JH5b germline | N W F D P W G Q G T L V T V S S |
| PTA021_A2 VH | G - - - - - - - - S - - - - - - |

FIGURE 5

Anti- CADM1 PTA021_A3 VH

| | |
|---|---|
| 2-05 germline | Q I T L K E S G P T L V K P T Q T L |
| PTA021_A3 VH | - - - - - - - - - - - - - - - - - |

_CDR1_____

| | |
|---|---|
| 2-05 germline | T L T C T F S G F S L S T S G V G V |
| PTA021_A3 VH | - - - - - - - - - - - - - - - - - |

_CDR2

| | |
|---|---|
| 2-05 germline | G W I R Q P P G K A L E W L A L I Y |
| PTA021_A3 VH | - - - - - - - - - - - - - - - - - |

CDR2_____

| | |
|---|---|
| 2-05 germline | W N D D K R Y S P S L K S R L T I T |
| PTA021_A3 VH | - D - - - - - - - - - - - - - - - |

| | |
|---|---|
| 2-05 germline | K D T S K N Q V V L T M T N M D P V |
| PTA021_A3 VH | - - - - - - - - - - - - - - - - - |

_CDR3_____

| | |
|---|---|
| 2-05 germline | D T A T Y Y C A H R |
| PTA021_A3 VH | - - - - - - - - - - R V E W V T L A |

_CDR3_____

| | |
|---|---|
| JH5b germline | N W F D P W G Q G T L V T V S S |
| PTA021_A3 VH | G - - - - - - - - - - - - - - - |

FIGURE 6

Anti- CADM1 PTA021_A1 VK

```
_CDR1_____
L15 germline     D I Q M T Q S P S S L S A S V G D R V T I T C R A
S Q G I S S
PTA021_A1 VK     - - - - - - - - - - - - - - - - - - - - - - - - -
- - - - -

_____                           _CDR2_____
L15 germline     W L A W Y Q Q K P E K A P K S L I Y A A S S L Q S
G V P S R F
PTA021_A1 VK     - - - - - - - - - - - - - - - - - G - - - - - - -
- - - - -

_CDR3_____
L15 germline     S G S G S G T D F T L T I S S L Q P E D F A T Y Y
C Q Q Y N S
PTA021_A1 VK     - - - - - - - - - - - - - - N - - - - - - - - - -
- - - - -

_____
L15 germline     Y P
JK4 germline         L T F G G G T K V E I K
PTA021_A1 VK     - - - - - - - - - - - - - -
```

FIGURE 7

Anti- CADM1 PTA021_A2 VK

```
            _CDR1_____
L15 germline           D I Q M T Q S P S S L S A S V G D R V T I T C R A
S Q G I S S
PTA021_A2 VK           - - - - - - - - - - - - - - - - - - - - - - - -
- - - - -

_CDR2_____
L15 germline           W L A W Y Q Q K P E K A P K S L I Y A A S S L Q S
G V P S R F
PTA021_A2 VK           - - - - - - - - - - - - - - - - - - - - - - - -
- - - - -

_CDR3_____
L15 germline           S G S G S G T D F T L T I S S L Q P E D F A T Y Y
C Q Q Y N S
PTA021_A2 VK           - - - - - - - - - - - - - - - - - - - - - - - -
- - - - -

_____
L15 germline           Y P
JK4 germline               L T F G G G T K V E I K
PTA021_A2 VK           - - - - - - - - - - - - - -
```

FIGURE 8

Anti- CADM1 PTA021_A3 VK

```
_CDR1_____
L15 germline    D I Q M T Q S P S S L S A S V G D R V T I T C R A S Q G I S S
PTA021_A3 VK    - - - - - - - - - - - - - - - - - - - - - - - - - - - - - -

_CDR2_____
L15 germline    W L A W Y Q Q K P E K A P K S L I Y A A S S L Q S G V P S R F
PTA021_A3 VK    - - - - - - - - - - - - - - - - - - - - - - - - - - - - - -

_CDR3_____
L15 germline    S G S G S G T D F T L T I S S L Q P E D F A T Y Y C Q Q Y N S
PTA021_A3 VK    - - - - - - - - - - - - - - - N - - - - - - - - - - - - - - -

_____
L15 germline    Y P
JK4 germline        L T F G G G T K V E I K
PTA021_A3 VK    - - - - - - - - - - - - - - -
```

FIGURE 9

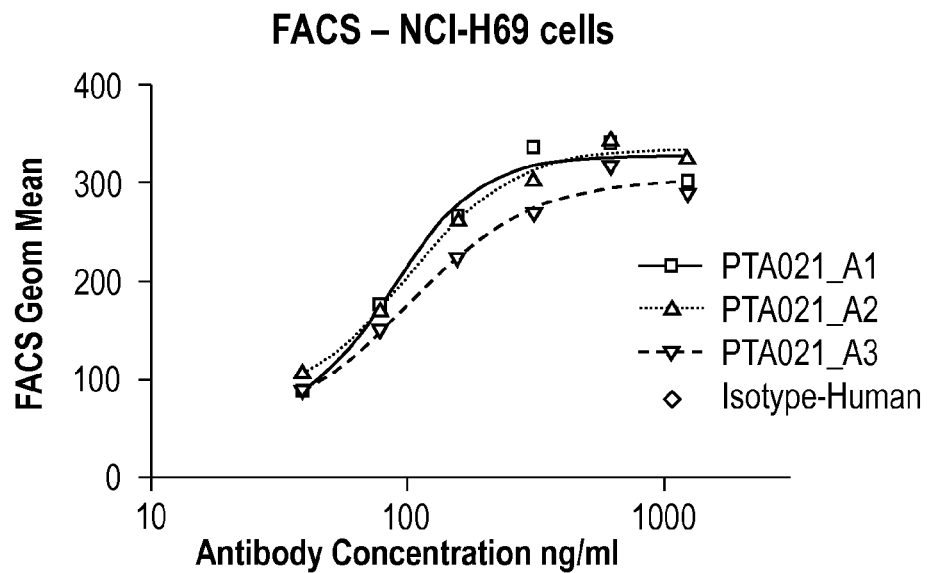
FIGURE 10
FACS: NCI – H69 cells
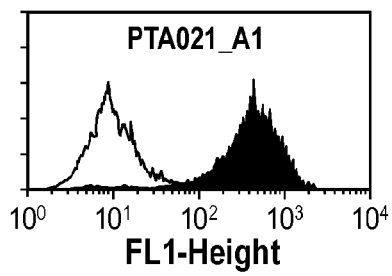
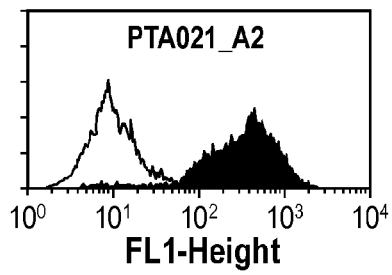
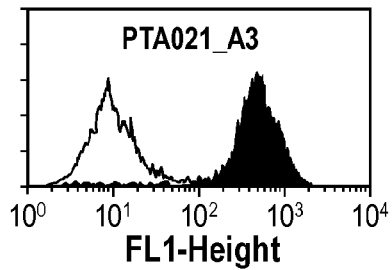
FIGURE 11A
FACS: DMS79 cells
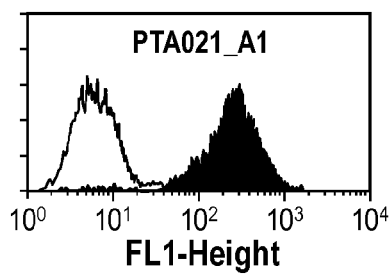
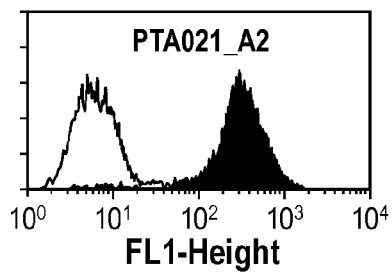
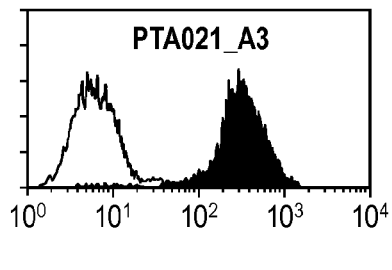
FIGURE 11B FACS: 786-O, RCC & SkMel28, Melanoma cell lines FACS: PTA021_A3 (NF) in NCI-H69 and DMS79 cells

US 8,420,084 B2

FULLY HUMAN ANTIBODIES SPECIFIC TO CADM1

RELATED APPLICATIONS

This application is a 35 U.S.C. 371 national stage filing of International Application No. PCT/US2010/026315, filed Mar. 5, 2010, which claims priority to U.S. Provisional Application No. 61/209,471, filed on Mar. 5, 2009 and U.S. Provisional Application No. 61/209,390, filed on Mar. 5, 2009. The contents of the aforementioned applications are hereby incorporated by reference.

FIELD OF THE INVENTION

The present invention relates generally to the fields of immunology and molecular biology. More specifically, provided herein are antibodies, particularly engineered antibodies resulting in increased binding to Fc receptors and/or increased potency for ADCC and immunoconjugates, and other therapeutic proteins directed against immunoglobulin-like adhesion molecule CADM1, nucleic acids encoding such antibodies and therapeutic proteins, methods for preparing inventive monoclonal antibodies and other therapeutic proteins, and methods for the treatment of diseases, such as cancers mediated by CADM1 expression/activity and/or associated with abnormal expression/activity of ligands therefore.

BACKGROUND OF THE INVENTION

Cell adhesion molecules are generally identified as cadherins, integrins, selectins, or as members of the Immunoglobulin (Ig) superfamily. The immunoglobulin superfamily molecules include cell surface antigen receptors, co-receptors and co-stimulatory molecules of the immune system, molecules involved in antigen presentation to lymphocytes, cell adhesion molecules and some cytokine receptors. Ig superfamily cell adhesion molecules constitute over 100 molecules in vertebrates, and include NCAMs (neural cell adhesion molecules), L1 family CAMs, ICAMS (intracellular cell adhesion molecules), VCAMS (vascular cell adhesion molecules), SIGLECs (sialic acid binding Ig-like lectins, including CD22 and CD83), nectins, CD2, CD48.

The immunoglobulin superfamily molecule CADM1 was initially characterized by multiple research groups; as a result the molecule is identified by many names in scientific literature including cell adhesion molecule 1, synaptic cell adhesion molecule (synCAM), spermatogenic immunoglobulin superfamily molecule (sgIGSF), IGSF4, BL2, ST17, NECL2, RA175, and CADM1A. Initially reported to further act as a tumor suppressor, it is also known as TSLC1 (Murakami et al., *Nature Genetics* 27(4):427 (2001)).

Unlike cadherins and integrins, which require divalent cations such as $Ca^{+2}$ or $Mg^{+2}$ for adhesive activities, Ig superfamily molecules are typically $Ca^{+2}$ or $Mg^{+2}$ independent. The CADM1 structure is characterized as having an extracellular domain with three immunoglobulin-like motifs, a single hydrophobic membrane-spanning α helix and an intracellular domain that binds actin fibers via DAL-1, and a short C-terminal cytoplasmic tail containing a PDZ-binding motif. Two CADM1 isoforms are known, NM_014333 and NM_001098517, the latter having a 27 amino acid deletion. Analysis indicates that the amino acid sequences corresponding to the cytoplasmic domain of CADM1 are identical in five mammals and highly conserved in vertebrates, suggesting an important role of CADM1 in normal cell-cell interaction. The mouse CADM1 orthologue (AAQ023810) shows 97% identity to the human CADM1. (Fukami et al., *Gene* 295:7-12 (2002)).

CADM1 is expressed in nerves and mast cells (Ito et al. *J Pharmacol Sci.;* 102(1):1-5 (2006)), pulmonary alveolar cells (Ito et al. *Histol Histopathol.* 18(4):1321-9 (2003)), pancreatic secretory cells (Shingai et al. *J Biol Chem.;* 278 (37):35421-7 (2003)), (Wakayama et al., *Blood;* 101(7):2601-8 (2003)). It is also associated with hepatocellular carcinoma (HCC). CADM1 appears to be expressed in fetal and cirrhotic adult bile duct cells, but is absent from disease-free adult bile ducts (Ito et al., *Hepatology;* 45(3): 684-94 (2007)). It is further reported to be associated with glioblastomas and lung cancer.

Two mechanisms resulting in CADM1 inactivation have been identified: through promoter methylation, and through loss of heterozygosity at the gene locus. Methylation of the CADM1 promoter reportedly results in loss of CADM1 expression in tumors, including lung esophageal, pancreatic, breast, and prostate cancers, particularly in tumors with aggressive behavior. (Murakami et al., *Mol Cancer.* 4:28 (2005)).

SUMMARY OF THE INVENTION

The present invention addresses these and other related needs by providing antibodies, particularly engineered antibodies resulting in increased binding to Fc receptors and/or increased potency for ADCC and immunoconjugates, directed against CADM1 therefore, nucleic acids encoding such antibodies and therapeutic proteins, methods for preparing anti-CADM1 monoclonal antibodies and other therapeutic proteins, and methods for the treatment of diseases, such as CADM1 mediated disorders, e.g., human cancers, including small cell lung cancer, adult T-cell leukemia, non-small cell lung cancer (including squamous carcinomas and adenocarcinomas), melanoma, breast cancer, colorectal cancer, ovarian cancer, prostate cancer, neuroendocrine cancers including those of lung, adrenal, pituitary, GI-tract, kidney, liver (including hepatocellular carcinomas), pancreas (including insulinomas and glucagonomas), glioblastomas, and carcinoid tumors including those of pancreas, lung, GI tract, liver, or kidney.

Thus, the present invention provides isolated monoclonal antibodies, in particular murine, chimeric, humanized, and fully-human monoclonal antibodies, that bind to one or more bone morphogenic protein and receptors therefore and that exhibit one or more desirable functional property. Such properties include, for example, high affinity specific binding to human CADM1. Also provided are methods for treating a variety of CADM1-mediated diseases using the antibodies, proteins, and compositions of the present invention.

The present invention provides an isolated monoclonal antibody, or an antigen-binding portion thereof, an antibody fragment, or an antibody mimetic which binds an epitope on human CADM1 recognized by an antibody comprising a heavy chain variable region comprising the amino acid sequence set forth in SEQ ID NO: 19, 20, or 21 and a light chain variable region comprising the amino acid sequence set forth in SEQ ID NO: 22, 23, or 24. In some embodiments the isolated antibody is a full-length antibody of an IgG1, IgG2, IgG3, or IgG4 isotype.

In some embodiments, the antibody of the present invention is selected from the group consisting of: a whole antibody, an antibody fragment, a humanized antibody, a single chain antibody, an immunoconjugate, an engineered antibody resulting in increased binding to Fc receptors and/or increased potency for ADCC, and a bispecific antibody. In a preferred embodiment, the antibody of the present invention is an immunoconjugate or an engineered antibody resulting in increased binding to Fc receptors and/or increased potency for ADCC. The antibody fragment may be selected from the group consisting of: a UniBody, a domain antibody, and a Nanobody. In some embodiments, the immunoconjugates of the invention comprise a therapeutic agent. In another aspect of the invention, the therapeutic agent is a cytotoxin or a radioactive isotope.

In some embodiments, the antibody of the present invention is selected from the group consisting of: an Affibody, a DARPin, an Anticalin, an Avimer, a Versabody, and a Duocalin.

In some aspects of the invention, the antibody binds to human CADM1 with an $EC_{50}$ of <50 Nm, <10 Nm, or <1 Nm.

In alternative embodiments, compositions of the present invention comprise an isolated antibody or antigen-binding portion and a pharmaceutically acceptable carrier.

In other aspects, the antibody of the present invention is a composition comprising the isolated antibody or antigen-binding portion thereof of claim 1 and a pharmaceutically acceptable carrier.

In some embodiments, the invention comprises an isolated nucleic acid molecule encoding the heavy or light chain of the isolated antibody or antigen-binding portion which binds an epitope on human CADM1. Other aspects of the invention comprise expression vectors comprising such nucleic acid molecules, and host cells comprising such.

In some embodiments, the present invention provides a method for preparing an anti-CADM1 antibody, said method comprising the steps of: obtaining a host cell that contains one or more nucleic acid molecules encoding the antibody of the invention; growing the host cell in a host cell culture; providing host cell culture conditions wherein the one or more nucleic acid molecules are expressed; and recovering the antibody from the host cell or from the host cell culture.

In other embodiments, the invention is directed to methods for treating or preventing a disease associated with target cells expressing CADM1, said method comprising the step of administering to a subject an anti-CADM1 antibody, or antigen-binding portion thereof, in an amount effective to treat or prevent the disease. In some aspects, the disease treated or prevented by the antibodies or antigen-binding portion thereof of the invention, is selected from the group consisting of: human cancers. In some embodiments, the disease treated or prevented by the antibodies of the present invention is a cancer selected from the group consisting of: small cell lung cancer, adult T-cell leukemia, non-small cell lung cancer (including squamous carcinomas and adenocarcinomas), melanoma, breast cancer, colorectal cancer, ovarian cancer, prostate cancer, neuroendocrine cancers including those of lung, adrenal, pituitary, GI-tract, kidney, liver (including hepatocellular carcinomas), pancreas (including insulinomas and glucagonomas), glioblastomas, and carcinoid tumors including those of pancreas, lung, GI tract, liver, or kidney.

In other embodiments, the invention is directed to an anti-CADM1 antibody, or antigen-binding portion thereof, for use in treating or preventing a disease associated with target cells expressing CADM1. In some aspects, the disease treated or prevented by the antibody or antigen-binding portion thereof of the invention, is human cancer. In some embodiments, the disease treated or prevented by the antibodies of the present invention is a cancer selected from the group consisting of: small cell lung cancer, adult T-cell leukemia, non-small cell lung cancer (including squamous carcinomas and adenocarcinomas), melanoma, breast cancer, colorectal cancer, ovarian cancer, prostate cancer, neuroendocrine cancers including those of lung, adrenal, pituitary, GI-tract, kidney, liver (including hepatocellular carcinomas), pancreas (including insulinomas and glucagonomas), glioblastomas, and carcinoid tumors including those of pancreas, lung, GI tract, liver, or kidney.

In other embodiments, the invention is directed to the use of an anti-CADM1 antibody, or antigen-binding portion thereof, for the manufacture of a medicament for use in treating or preventing a disease associated with target cells expressing CADM1. In some aspects, the disease treated or prevented by the medicament of the invention, is human cancer. In some embodiments, the disease treated or prevented by the medicament of the invention is a cancer selected from the group consisting of: small cell lung cancer, adult T-cell leukemia, non-small cell lung cancer (including squamous carcinomas and adenocarcinomas), melanoma, breast cancer, colorectal cancer, ovarian cancer, prostate cancer, neuroendocrine cancers including those of lung, adrenal, pituitary, GI-tract, kidney, liver (including hepatocellular carcinomas), pancreas (including insulinomas and glucagonomas), glioblastomas, and carcinoid tumors including those of pancreas, lung, GI tract, liver, or kidney.

In other embodiments, the present invention is an isolated monoclonal antibody or an antigen binding portion thereof, an antibody fragment, or an antibody mimetic which binds an epitope on human CADM1 recognized by an antibody comprising a heavy chain variable region and a light chain variable region selected from the group consisting of the heavy chain variable region amino acid sequence set forth in SEQ ID NO:19 and the light chain variable region amino acid sequence set forth in SEQ ID NO:22; the heavy chain variable region amino acid sequence set forth in SEQ ID NO:20 and the light chain variable region amino acid sequence set forth in SEQ ID NO:23; the heavy chain variable region amino acid sequence set forth in SEQ ID NO:21 and the light chain variable region amino acid sequence set forth in SEQ ID NO:24. In further aspects, the antibody is selected from the group consisting of: a whole antibody, an antibody fragment, a humanized antibody, a single chain antibody, an immunoconjugate, an engineered antibody resulting in increased binding to Fc receptors and/or increased potency for ADCC, and a bispecific antibody. In a preferred aspect, the antibody is an immunoconjugate or an engineered antibody resulting in increased binding to Fc receptors and/or increased potency for ADCC. In further aspects of the invention, the antibody fragment is selected from the group consisting of: a UniBody, a domain antibody, and a Nanobody. In some embodiments, the antibody mimetic is selected from the group consisting of: an Affibody, a DARPin, an Anticalin, an Avimer, a Versabody, and a Duocalin. In further embodiments, the composition comprises the isolated antibody or antigen binding portion thereof and a pharmaceutically acceptable carrier.

In some embodiments, the present invention is an isolated nucleic acid molecule encoding the heavy or light chain of the isolated antibody or antigen binding portion thereof of antibody of the invention, and in further aspects may include an expression vector comprising such nucleic acids, and host cells comprising such expression vectors.

Another embodiment of the present invention is a hybridoma expressing the antibody or antigen binding portion thereof of any one of antibodies of the invention.

Other aspects of the invention are directed to methods of making the antibodies of the invention, comprising the steps of: immunizing a transgenic animal comprising human immunoglobulin genes with a CADM1 peptide; recovering B-cells from said transgenic animal; making hybridomas from said B-cells; selecting hybridomas that express antibodies that bind CADM1; and recovering said antibodies that bind CADM1 from said selected hybridomas.

In other embodiments, the method of making anti-CADM1 antibodies, comprises the steps of:

immunizing a transgenic animal comprising human immunoglobulin genes with a CADM1 peptide;

recovering mRNA from the B cells of said transgenic animal; converting said mRNA to cDNA;

expressing said cDNA in phages such that anti-CADM1 antibodies encoded by said cDNA are presented on the surface of said phages;

selecting phages that present anti-CADM1 antibodies;

recovering nucleic acid molecules from said selected phages that encode said anti-CADM1 immunoglobulins;

expressing said recovered nucleic acid molecules in a host cell; and recovering antibodies from said host cell that bind CADM1.

In some aspects of the invention, the isolated monoclonal antibody, or an antigen binding portion thereof, binds an epitope on the CADM1 polypeptide having an amino acid sequence of SEQ ID NOS: 43 or 44 recognized by an antibody comprising a heavy chain variable region comprising the amino acid sequence set forth in SEQ ID NOS: 19, 20, or 21 and a light chain variable region comprising the amino acid sequence set forth in SEQ ID NOS: 22, 23, or 24.

Other features and advantages of the instant invention will be apparent from the following detailed description and examples which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO:25) and amino acid sequence (SEQ ID NO:19) of the heavy chain variable region of the PTA021_A1 human monoclonal antibody. The CDR1 (SEQ ID NO:1), CDR2 (SEQ ID NO:4) and CDR3 (SEQ ID NO:7) regions are delineated and the V, D and J germline derivations are indicated.

FIG. 1B shows the nucleotide sequence (SEQ ID NO:28) and amino acid sequence (SEQ ID NO:22) of the light chain variable region of the PTA021_A1 human monoclonal antibody. The CDR1 (SEQ ID NO:10), CDR2 (SEQ ID NO:13) and CDR3 (SEQ ID NO:16) regions are delineated and the V and J germline derivations are indicated.

FIG. 2A shows the nucleotide sequence (SEQ ID NO:26) and amino acid sequence (SEQ ID NO:20) of the heavy chain variable region of the PTA021_A2 human monoclonal antibody. The CDR1 (SEQ ID NO:2), CDR2 (SEQ ID NO:5) and CDR3 (SEQ ID NO:8) regions are delineated and the V and J germline derivations are indicated.

FIG. 2B shows the nucleotide sequence (SEQ ID NO:29) and amino acid sequence (SEQ ID NO:23) of the light chain variable region of the PTA021_A2 human monoclonal antibody. The CDR1 (SEQ ID NO:11), CDR2 (SEQ ID NO:14) and CDR3 (SEQ ID NO:17) regions are delineated and the V and J germline derivations are indicated.

FIG. 3A shows the nucleotide sequence (SEQ ID NO:27) and amino acid sequence (SEQ ID NO:21) of the heavy chain variable region of the PTA021_A3 human monoclonal antibody. The CDR1 (SEQ ID NO:3), CDR2 (SEQ ID NO:6) and CDR3 (SEQ ID NO:9) regions are delineated and the V, D and J germline derivations are indicated.

FIG. 3B shows the nucleotide sequence (SEQ ID NO:30) and amino acid sequence (SEQ ID NO:24) of the light chain variable region of the PTA021_A3 human monoclonal antibody. The CDR1 (SEQ ID NO:12), CDR2 (SEQ ID NO:15) and CDR3 (SEQ ID NO:18) regions are delineated and the V and J germline derivations are indicated.

FIG. 4 shows the alignment of the amino acid sequence of the heavy chain variable region of PTA021_A1 (SEQ ID NO:19) with the human germline $V_H$ 2-05 amino acid sequence (SEQ ID NO:31) and the human germline $J_H$ JH5b amino acid sequence (SEQ ID NO:37).

FIG. 5 shows the alignment of the amino acid sequence of the heavy chain variable region of PTA021_A2 (SEQ ID NO:20) with the human germline $V_H$ 2-05 amino acid sequences (SEQ ID NO:32) and the human germline $J_H$ 5b amino acid sequence (SEQ ID NO:38).

FIG. 6 shows the alignment of the amino acid sequence of the heavy chain variable region of PTA021_A3 (SEQ ID NO:21) with the human germline $V_H$ 2-05 amino acid sequences (SEQ ID NO:33) and the human germline $J_H$ 5b amino acid sequence (SEQ ID NO:39).

FIG. 7 shows the alignment of the amino acid sequence of the light chain variable region of PTA021_A1 (SEQ ID NO:22) with the human germline $V_K$ L15 amino acid sequence (SEQ ID NO:34) and the human germline $J_K$ 4 amino acid sequence (SEQ ID NO:40).

FIG. 8 shows the alignment of the amino acid sequence of the light chain variable region of PTA021_A2 (SEQ ID NO:23) with the human germline $V_k$ L15 amino acid sequence (SEQ ID NO:35) and the human germline $J_K$ 4 amino acid sequence (SEQ ID NO:41).

FIG. 9 shows the alignment of the amino acid sequence of the light chain variable region of PTA021_A3 (SEQ ID NO:24) with the human germline $V_k$ L15 amino acid sequence (SEQ ID NO:36) and the human germline $J_K$ 4 amino acid sequence (SEQ ID NO:42).

FIG. 10 shows the results of FACS analysis on PTA021_A1, PTA021_A2 and PTA021_A3 in NCI-H69 small cell lung cancer cells.

FIGS. 11A and 11B show the results of FACS analysis on PTA021_A1, PTA021_A2 and PTA021_A3 in NCI-H69 and DMS79 small cell lung cancer cells respectively.

DETAILED DESCRIPTION OF THE INVENTION

Figure 12:
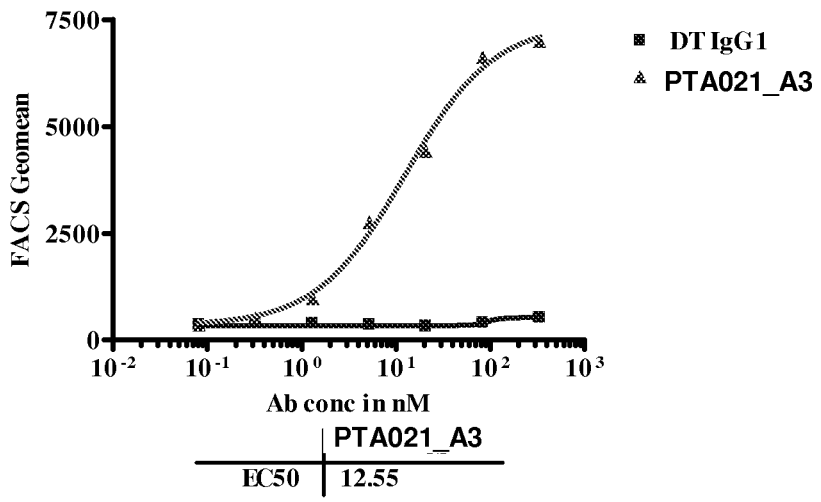
FIG. 12 shows the results of FACS analysis on PTA021_A3 in SKOV3 ovarian cancer cells.

The present invention relates to isolated monoclonal antibodies, particularly human monoclonal antibodies, more particularly immunoconjugates and engineered antibodies resulting in increased binding to Fc receptors and/or increased potency for ADCC, which bind specifically to CADM1 with high affinity. In certain embodiments, the antibodies of the invention are derived from particular heavy and light chain germline sequences and/or comprise particular structural features such as CDR regions comprising particular amino acid sequences. The invention provides isolated antibodies, engineered antibodies resulting in increased binding to Fc receptors and/or increased potency for ADCC, immunoconjugates, bispecific molecules, affibodies, domain antibodies, nanobodies, and unibodies, methods of making said molecules, and pharmaceutical compositions comprising said molecules and a pharmaceutical carrier. The invention also relates to methods of using the molecules, such as to detect CADM1, as well as to treat diseases associated with expression of CADM1, such as CADM1 expressed on tumors, including those tumors of small cell lung cancer, and neuroendocrine pancreatic cancer, lung carcinoids, and gastro-intestinal carcinoids.

In order that the present invention may be more readily understood, certain terms are first defined. Additional definitions are set forth throughout the detailed description.

The terms "CADM1", "IGSF4", "immunoglobulin superfamily, member 4D", "cell adhesion molecule 1", "tumor suppressor in lung cancer 1", "TSLC1", "BL2", "ST17", "synaptic cell adhesion molecule", "syncam 1", "nectin-like protein 2" and "NECL2" are used interchangeably, and include variants, isoforms and species homologs of human CADM1, including CADM1 isoform 1 (Genbank Accession Nos. NM_014333), and 2 (Genbank Accession Nos. NM_001098517). The two isoforms have also been identified as OGTA025a and OGTA025b in PCT Application No. PCT/GB2007/050515, which is incorporated herein by reference in its entirety. Human antibodies of this disclosure may, in certain cases, cross-react with CADM1 from species other than human. In certain embodiments, the antibodies may be completely specific for one or more human CADM1 and may not exhibit species or other types of non-human cross-reactivity. The complete amino acid sequence of an exemplary human CADM1 has Genbank accession number NM_014333.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between various of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present invention is the CADM1 receptor.

The term "antibody" as referred to herein includes whole antibodies and any antigen binding fragment (i.e., "antigen-binding portion") or single chains thereof. An "antibody" refers to a glycoprotein which may comprise at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$ or $V_K$) and a light chain constant region. The light chain constant region is comprised of one domain, $C_L$. The $V_H$ and $V_L/V_K$ regions can be further subdivided into regions of hypervariability, termed complementarity determining regions (CDR), interspersed with regions that are more conserved, termed framework regions (FR). Each $V_H$ and $V_L/V_K$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., CADM1). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L/V_K$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L/V_K$ and $V_H$, are coded for by separate genes, they can be joined, using recombinant methods, by a synthetic linker that enables them to be made as a single protein chain in which the $V_L/V_K$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds CADM1 is substantially free of antibodies that specifically bind antigens other than CADM1). An isolated antibody that specifically binds CADM1 may, however, have cross-reactivity to other antigens, such as CADM1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L/V_K$ regions of the recombinant antibodies are sequences that, while derived from and related to human germline $V_H$ and $V_L/V_K$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human CADM1" is intended to refer to an antibody that binds to human CADM1 with an $EC_{50}$ of 50 Nm or less, 10 Nm or less, or more preferably 1 Nm or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$EC_{50}$," as used herein, is intended to refer to the potency of a compound by quantifying the concentration that leads to 50% maximal response/effect.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Accordingly, also encompassed by the present invention are antibodies that bind to (i.e., recognize) the same epitope as the antibodies described herein (i.e., PTA021_A1, PTA021_A2 and PTA021_A3). Antibodies that bind to the same epitope can be identified by their ability to cross-compete with (i.e., competitively inhibit binding of) a reference antibody to a target antigen in a statistically significant manner. Competitive inhibition can occur, for example, if the antibodies bind to identical or structurally similar epitopes (e.g., overlapping epitopes), or spatially proximal epitopes which, when bound, causes steric hindrance between the antibodies.

Competitive inhibition can be determined using routine assays in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Various aspects of the invention are described in further detail in the following subsections.

Anti-CADM1 Antibodies

The antibodies of the invention are characterized by particular functional features or properties of the antibodies. For example, the antibodies bind specifically to human CADM1. Preferably, an antibody of the invention binds to CADM1 with high affinity, for example with a $K_D$ of $8 \times 10^{-7}$ M or less, even more typically $1 \times 10^{-8}$ M or less. The anti-CADM1 antibodies of the invention preferably exhibit one or more of the following characteristics:

binds to human CADM1 with a $EC_{50}$ of 50 Nm or less, 10 Nm or less, or more preferably 1 Nm or less;

binds to human cells expressing CADM1.

In one embodiment, the antibodies preferably bind to an antigenic epitope present in CADM1, which epitope is not present in other proteins. The antibodies typically bind CADM1 but does not bind to other proteins, or binds to proteins with a low affinity, such as a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more. Preferably, the antibodies do not bind to related proteins, for example, the antibodies do not substantially bind to ICAMs, VCAMs, or other cell adhesion molecules. In one embodiment, the antibody may be internalized into a cell expressing CADM1. Standard assays to evaluate antibody internalization are known in the art, including, for example, a HumZap internalization assay.

Standard assays to evaluate the binding ability of the antibodies toward CADM1 are known in the art, including for example, ELISAs, Western blots, RIAs, and flow cytometry analysis. Suitable assays are described in detail in the Examples. The binding kinetics (e.g., binding affinity) of the antibodies also can be assessed by standard assays known in the art, such as by Biacore® system analysis. To assess binding to Raji or Daudi B cell tumor cells, Raji (ATCC Deposit No. CCL-86) or Daudi (ATCC Deposit No. CCL-213) cells can be obtained from publicly available sources, such as the American Type Culture Collection, and used in standard assays, such as flow cytometric analysis.

Monoclonal Antibodies PTA021_A1, PTA021_A2, PTA021_A3

Preferred antibodies of the invention are the human monoclonal antibodies PTA021_A1, PTA021_A2, and PTA021_A3, isolated and structurally characterized as described in Examples 1, 2, and 3. The $V_H$ amino acid sequences of PTA021_A1, PTA021_A2, and PTA021_A3 are shown in SEQ ID NOs:19, 20, and 21, respectively. The $V_K$ amino acid sequences of PTA021_A1, PTA021_A2, and PTA021_A3 are shown in SEQ ID NOs:22, 23, and 24, respectively.

Given that each of these antibodies can bind to CADM1, the $V_H$ and $V_K$ sequences can be "mixed and matched" to create other anti-CADM1 binding molecules of the invention. CADM1 binding of such "mixed and matched" antibodies can be tested using the binding assays described above and in the Examples (e.g., ELISAs). Preferably, when $V_H$ and $V_K$ chains are mixed and matched, a $V_H$ sequence from a particular $V_H/V_K$ pairing is replaced with a structurally similar $V_H$ sequence. Likewise, preferably a $V_L$ sequence from a particular $V_H/V_K$ pairing is replaced with a structurally similar $V_K$ sequence.

Accordingly, in one aspect, the invention provides an isolated monoclonal antibody, or antigen binding portion thereof comprising:
a heavy chain variable region comprising an amino acid sequence selected from the group consisting of SEQ ID NOs: 19, 20, and 21; and
a light chain variable region comprising an amino acid sequence selected from the group consisting of SEQ ID NOs: 22, 23, and 24;
wherein the antibody specifically binds CADM1, preferably human CADM1.

Preferred heavy and light chain combinations include:
a heavy chain variable region comprising the amino acid sequence of SEQ ID NO:19 and a light chain variable region comprising the amino acid sequence of SEQ ID NO:22; or
a heavy chain variable region comprising the amino acid sequence of SEQ ID NO:20; and a light chain variable region comprising the amino acid sequence of SEQ ID NO:23, or
a heavy chain variable region comprising the amino acid sequence of SEQ ID NO:21; and a light chain variable region comprising the amino acid sequence of SEQ ID NO:24.

In another aspect, the invention provides antibodies that comprise the heavy chain and light chain CDR1s, CDR2s and CDR3s of PTA021_A1, PTA021_A2, and PTA021_A3, or combinations thereof. The amino acid sequences of the $V_H$ CDR1s of PTA021_A1, PTA021_A2, and PTA021_A3 are shown in SEQ ID NOs: 1, 2, and 3. The amino acid sequences of the $V_H$ CDR2s of PTA021_A1, PTA021_A2, and PTA021_A3 are shown in SEQ ID NOs: 4, 5, and 6. The amino acid sequences of the $V_H$ CDR3s of PTA021_A1, PTA021_A2, and PTA021_A3 are shown in SEQ ID NOs:7, 8, and 9. The amino acid sequences of the $V_K$ CDR1s of PTA021_A1, PTA021_A2, and PTA021_A3 are shown in SEQ ID NOs:10, 11, and 12. The amino acid sequences of the $V_K$ CDR2s of PTA021_A1, PTA021_A2, and PTA021_A3 are shown in SEQ ID NOs:13, 14, and 15. The amino acid sequences of the $V_K$ CDR3s of PTA021_A1, PTA021_A2, and PTA021_A3 are shown in SEQ ID NOs:16, 17, and 18. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to CADM1 and that antigen-binding specificity is provided primarily by the CDR1, CDR2, and CDR3 regions, the $V_H$ CDR1, CDR2, and CDR3 sequences and $V_K$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_K$ CDR1, CDR2, and CDR3) to create other anti-CADM1 binding molecules of the invention. CADM1 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_K$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_K$ sequences can be created by substituting one or more $V_H$ and/or $V_L/V_K$ CDR region sequences with structurally similar sequences from the CDR sequences disclosed herein for monoclonal antibodies PTA021_A1, PTA021_A2 and PTA021_A3.

Accordingly, in another aspect, the invention provides an isolated monoclonal antibody, or antigen binding portion thereof comprising:
a heavy chain variable region CDR1 comprising an amino acid sequence selected from the group consisting of SEQ ID NOs:1, 2, and 3;
a heavy chain variable region CDR2 comprising an amino acid sequence selected from the group consisting of SEQ ID NOs:4, 5, and 6;
a heavy chain variable region CDR3 comprising an amino acid sequence selected from the group consisting of SEQ ID NOs:7, 8, and 9;
a light chain variable region CDR1 comprising an amino acid sequence selected from the group consisting of SEQ ID NOs: 10, 11, and 12;
a light chain variable region CDR2 comprising an amino acid sequence selected from the group consisting of SEQ ID NOs: 13, 14, and 15; and
a light chain variable region CDR3 comprising an amino acid sequence selected from the group consisting of SEQ ID NOs: 16, 17, and 18;
wherein the antibody specifically binds CADM1, preferably human CADM1.

In a preferred embodiment, the antibody comprises:
a heavy chain variable region CDR1 comprising SEQ ID NO:1;
a heavy chain variable region CDR2 comprising SEQ ID NO: 4;
a heavy chain variable region CDR3 comprising SEQ ID NO: 7;
a light chain variable region CDR1 comprising SEQ ID NO: 10;
a light chain variable region CDR2 comprising SEQ ID NO: 13; and
a light chain variable region CDR3 comprising SEQ ID NO: 16.

In another preferred embodiment, the antibody comprises:
a heavy chain variable region CDR1 comprising SEQ ID NO: 2;
a heavy chain variable region CDR2 comprising SEQ ID NO: 5;
a heavy chain variable region CDR3 comprising SEQ ID NO: 8;
a light chain variable region CDR1 comprising SEQ ID NO: 11;
a light chain variable region CDR2 comprising SEQ ID NO: 14; and
a light chain variable region CDR3 comprising SEQ ID NO: 17.

In another preferred embodiment, the antibody comprises:
a heavy chain variable region CDR1 comprising SEQ ID NO: 3;
a heavy chain variable region CDR2 comprising SEQ ID NO:6;
a heavy chain variable region CDR3 comprising SEQ ID NO:9;
a light chain variable region CDR1 comprising SEQ ID NO:12;
a light chain variable region CDR2 comprising SEQ ID NO: 15; and
a light chain variable region CDR3 comprising SEQ ID NO: 18.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., British J. of Cancer 83(2):252-260 (2000) (describing the production of a humanized anti-CD30 antibody using only the heavy chain variable domain CDR3 of murine anti-CD30 antibody Ki-4); Beiboer et al., J. Mol. Biol. 296:833-849 (2000) (describing recombinant epithelial glycoprotein-2 (EGP-2) antibodies using only the heavy chain CDR3 sequence of the parental murine MOC-31 anti-EGP-2 antibody); Rader et al., Proc. Natl. Acad. Sci. U.S.A. 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent murine antibody with affinities as high or higher than the parent murine antibody); Barbas et al., J. Am. Chem. Soc. 116:2161-2162 (1994) (disclosing that the CDR3 domain provides the most significant contribution to antigen binding); Barbas et al., Proc. Natl. Acad. Sci. U.S.A. 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); and Ditzel et al., J. Immunol. 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab). Each of these references is hereby incorporated by reference in its entirety.

Accordingly, the present invention provides monoclonal antibodies comprising one or more heavy and/or light chain CDR3 domains from an antibody derived from a human or non-human animal, wherein the monoclonal antibody is capable of specifically binding to CADM1. Within certain aspects, the present invention provides monoclonal antibodies comprising one or more heavy and/or light chain CDR3 domain from a non-human antibody, such as a mouse or rat antibody, wherein the monoclonal antibody is capable of specifically binding to CADM1. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present invention provides monoclonal antibodies comprising one or more heavy and/or light chain CDR3 domain from a human antibody, such as, for example, a human antibody obtained from a non-human animal, wherein the human antibody is capable of specifically binding to CADM1. Within other aspects, the present invention provides monoclonal antibodies comprising one or more heavy and/or light chain CDR3 domain from a first human antibody, such as, for example, a human antibody obtained from a non-human animal, wherein the first human antibody is capable of specifically binding to CADM1 and wherein the CDR3 domain from the first human antibody replaces a CDR3 domain in a human antibody that is lacking binding specificity for CADM1 to generate a second human antibody that is capable of specifically binding to CADM1. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody. In preferred embodiments, the first human antibody is PTA021_A1, PTA021_A2 or PTA021_A3.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 2-05 gene, wherein the antibody specifically binds CADM1. In yet another preferred embodiment, the invention provides an isolated monoclonal antibody, or an antigen-binding portion thereof, comprising a light chain variable region that is the product of or derived from a human $V_K$ L15 gene, wherein the antibody specifically binds CADM1. In yet another preferred embodiment, the invention provides an isolated monoclonal antibody, or antigen-binding portion thereof, wherein the antibody:
comprises a heavy chain variable region that is the product of or derived from a human $V_H$ 2-05 gene (which genes encode the amino acid sequences set forth in SEQ ID NOs: 31, 32, or 33, respectively);
comprises a light chain variable region that is the product of or derived from a human $V_K$ L15 gene (which genes encode the amino acid sequences set forth in SEQ ID NOs: 34, 35, or 36, respectively); and
specifically binds to CADM1, preferably human CADM1. Examples of an antibody having $V_H$ and $V_K$ of $V_H$ 2-05 and $V_K$ L15, respectively, are PTA021_A1, PTA021_A2, and PTA021_A3.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-CADM1 antibodies of the invention.

For example, the invention provides an isolated monoclonal antibody, or antigen binding portion thereof, comprising a heavy chain variable region and a light chain variable region, wherein:

the heavy chain variable region comprises an amino acid sequence that is at least 80% homologous to an amino acid sequence selected from the group consisting of SEQ ID NOs: 19, 20, and 21;

the light chain variable region comprises an amino acid sequence that is at least 80% homologous to an amino acid sequence selected from the group consisting of SEQ ID NOs: 22, 23, and 24; and the antibody binds to human CADM1 with a $EC_{50}$ of 10 Nm or less.

The antibody may also bind to CHO cells transfected with human CADM1.

In various embodiments, the antibody can be, for example, a human antibody, a humanized antibody or a chimeric antibody.

In other embodiments, the $V_H$ and/or $V_K$ amino acid sequences may be 85%, 90%, 95%, 96%, 97%, 98% or 99% homologous to the sequences set forth above. An antibody having $V_H$ and $V_K$ regions having high (i.e., 80% or greater) homology to the $V_H$ and $V_K$ regions of the sequences set forth above, can be obtained by mutagenesis (e.g., site-directed or PCR-mediated mutagenesis) of nucleic acid molecules encoding SEQ ID NOs:25, 26, 27, 28, 29, and 30, followed by testing of the encoded altered antibody for retained function using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., PTA021_A1, PTA021_A2 or PTA021_A3), or conservative modifications thereof, and wherein the antibodies retain the desired functional properties of the anti-CADM1 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

the heavy chain variable region CDR3 sequence comprises an amino acid sequence selected from the group consisting of amino acid sequences of SEQ ID NOs:7, 8, and 9, and conservative modifications thereof;

the light chain variable region CDR3 sequence comprises an amino acid sequence selected from the group consisting of amino acid sequence of SEQ ID NOs:16, 17, and 18, and conservative modifications thereof; and the antibody binds to human CADM1 with a $EC_{50}$ of 1 nM or less.

The antibody may also bind to CHO cells transfected with human CADM1.

In a preferred embodiment, the heavy chain variable region CDR2 sequence comprises an amino acid sequence selected from the group consisting of amino acid sequences of SEQ ID NOs:4, 5, and 6, and conservative modifications thereof; and the light chain variable region CDR2 sequence comprises an amino acid sequence selected from the group consisting of amino acid sequences of SEQ ID NOs:13, 14, and 15, and conservative modifications thereof. In another preferred embodiment, the heavy chain variable region CDR1 sequence comprises an amino acid sequence selected from the group consisting of amino acid sequences of SEQ ID NOs:1, 2, and 3, and conservative modifications thereof; and the light chain variable region CDR1 sequence comprises an amino acid sequence selected from the group consisting of amino acid sequences of SEQ ID NOs:10, 11, and 12, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein.

The heavy chain CDR1 sequence of SEQ ID NO:1, 2, or 3 may comprise one or more conservative sequence modification, such as one, two, three, four, five or more amino acid substitutions, additions or deletions; the light chain CDR1 sequence of SEQ ID NO:10, 11, or 12 may comprise one or more conservative sequence modification, such as one, two, three, four, five or more amino acid substitutions, additions or deletions; the heavy chain CDR2 sequence shown in SEQ ID NO:4, 5, or 6 may comprise one or more conservative sequence modification, such as one, two, three, four, five or more amino acid substitutions, additions or deletions; the light chain CDR2 sequence shown in SEQ ID NO:13, 14, or 15 may comprise one or more conservative sequence modification, such as one, two, three, four, five or more amino acid substitutions, additions or deletions; the heavy chain CDR3 sequence shown in SEQ ID NO:7, 8, or 9 may comprise one or more conservative sequence modification, such as one, two, three, four, five or more amino acid substitutions, additions or deletions; and/or the light chain CDR3 sequence shown in SEQ ID NO:16, 17, or 18 may comprise one or more conservative sequence modification, such as one, two, three, four, five or more amino acid substitutions, additions or deletions.

Antibodies that Bind to the Same Epitope as Anti-CADM1 Antibodies of the Invention In another embodiment, the invention provides antibodies that bind to the same epitope on human CADM1 as any of the CADM1 monoclonal antibodies of the invention (i.e., antibodies that have the ability to cross-compete for binding to CADM1 with any of the monoclonal antibodies of the invention). In preferred embodiments, the reference antibody for studies on cross-competition for binding can be the monoclonal antibody PTA021_A1 (having $V_H$ and $V_K$ sequences as shown in SEQ ID NOs:19 and 22, respectively), the monoclonal antibody PTA021_A2 (having $V_H$ and $V_K$ sequences as shown in SEQ ID NOs:20 and 23 respectively), or the monoclonal antibody PTA021_A3 (having $V_H$ and $V_K$ sequences as shown in SEQ ID NOs:21 and 24 respectively). Such cross-competing antibodies can be identified based on their ability to cross-compete with PTA021_A1, PTA021_A2 or PTA021_A3 in standard CADM1 binding assays. For example, BIAcore analysis, ELISA assays or flow cytometry may be used to demonstrate cross-competing for binding with the antibodies of the current invention. The ability of a test antibody to inhibit the binding of, for example, PTA021_A1, PTA021_A2 or PTA021_A3, to human CADM1 demonstrates that the test antibody can compete with PTA021_A1, PTA021_A2 or PTA021_A3 for binding to human CADM1 and thus binds to the same epitope on human CADM1 as PTA021_A1, PTA021_A2 or PTA021_A3. In a preferred embodiment, the antibody that binds to the same epitope on human CADM1 as PTA021_A1, PTA021_A2 or PTA021_A3 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein can be used as starting material to engineer a modified antibody, which modified antibody may have altered properties as compared to the starting antibody. An antibody can be engineered by modifying one or more amino acids within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature*

321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region portion comprising CDR1, CDR2, and CDR3 sequences comprising an amino acid sequence selected from the group consisting of SEQ ID NOs:1, 2, and 3, SEQ ID NOs:4, 5, and 6, and SEQ ID NOs:7, 8, and 9, respectively, and a light chain variable region comprising CDR1, CDR2, and CDR3 sequences comprising an amino acid sequence selected from the group consisting of SEQ ID NOs:10, 11, and 12, SEQ ID NOs:13, 14, and 15, and SEQ ID NOs:16, 17, and 18, respectively. Thus, such antibodies contain the $V_H$ and $V_K$ CDR sequences of monoclonal antibodies PTA021_A1, PTA021_A2 or PTA021_A3 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo22 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames.

The identities are exact amino acid matches between the antibody sequence and the protein database over the entire length of the sequence. The positives (identities + substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of the invention are those that are structurally similar to the framework sequences used by selected antibodies of the invention, e.g., similar to the $V_H$ 2-05 framework sequences (SEQ ID NO:31) and/or the $V_K$ L15 framework sequences (SEQ ID NO:34) used by preferred monoclonal antibodies of the invention. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-CADM1 monoclonal antibodies, or antigen binding portions thereof, comprising a heavy chain variable region comprising: (a) a $V_H$ CDR1 region comprising an amino acid sequence selected from the group consisting of SEQ ID NOs:1, 2, and 3, or an amino acid sequence having one, two, three, four or five amino acid substitutions, deletions or additions as compared to SEQ ID NOs:1, 2, and 3; (b) a $V_H$ CDR2 region comprising an amino acid sequence selected from the group consisting of SEQ ID NOs:4, 5, and 6, or an amino acid sequence having one, two, three, four or five amino acid substitutions, deletions or additions as compared to SEQ ID NOs:4, 5, and 6; (c) a $V_H$ CDR3 region comprising an amino acid sequence selected from the group consisting of SEQ ID NOs:7, 8, and 9, or an amino acid sequence having one, two, three, four or five amino acid substitutions, deletions or additions as compared to SEQ ID NOs:7, 8, and 9; (d) a $V_K$ CDR1 region comprising an amino acid sequence selected from the group consisting of SEQ ID NOs:10, 11, and 12, or an amino acid sequence having one, two, three, four or five amino acid substitutions, deletions or additions as compared to SEQ ID NOs:10, 11, and 12; (e) a $V_K$ CDR2 region comprising an amino acid sequence selected from the group consisting of SEQ ID NOs:13, 14, and 15, or an amino acid sequence having one, two, three, four or five amino acid substitutions, deletions or additions as compared to SEQ ID NOs:13, 14, and 15; and (f) a $V_K$ CDR3 region comprising an amino acid sequence selected from the group consisting of SEQ ID NOs:16, 17, and 18, or an amino acid sequence having one, two, three, four or five amino acid substitutions, deletions or additions as compared to SEQ ID NOs:16, 17, and 18.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for PTA021_A1, using the Kabat numbering system, amino acid residue #30 (within FR3) of $V_H$ is an asparagine (SEQ ID NO:19) whereas this residue in the corresponding $V_H$ 2-05 germline sequence is a serine (SEQ ID NO:31). To return the framework region sequences to their germline configuration, the somatic mutations can be "backmutated" to the germline sequence by, for example, site-directed mutagenesis or PCR-mediated mutagenesis (e.g., residue #30 of the $V_H$ of PTA021_A1 can be "backmutated" from asparagine to serine).

As another example, for PTA021_A1, amino acid residue #54 of $V_H$ is an aspartic acid (SEQ ID NO:19) whereas this residue in the corresponding $V_H$ 2-05 germline sequence is an asparagine (SEQ ID NO:31). To return the framework region sequences to their germline configuration, for example, residue #54 of the $V_H$ of PTA021_A1 can be "backmutated" from aspartic acid to asparagine. Such "backmutated" antibodies are also intended to be encompassed by the invention.

As another example, for PTA021_A1, amino acid residue #50 of $V_K$ is a glycine (SEQ ID NO:22) whereas this residue in the corresponding $V_K$ L15 germline sequence is an alanine (SEQ ID NO:34). To return the framework region sequences to their germline configuration, for example, residue #50 of the $V_K$ of PTA021_A1 can be "backmutated" from glycine to alanine. Such "backmutated" antibodies are also intended to be encompassed by the invention.

As another example, for PTA021_A1, amino acid residue #77 of $V_K$ is an asparagine (SEQ ID NO:22) whereas this residue in the corresponding $V_K$ L15 germline sequence is a serine (SEQ ID NO:34). To return the framework region sequences to their germline configuration, for example, residue #77 of the $V_K$ of PTA021_A1 can be "backmutated" from asparagine to serine. Such "backmutated" antibodies are also intended to be encompassed by the invention.

As another example, for PTA021_A2, amino acid residue #54 of $V_H$ is an aspartic acid (SEQ ID NO:20) whereas this residue in the corresponding $V_H$ 2-05 germline sequence is an asparagine (SEQ ID NO:32). To return the framework region sequences to their germline configuration, for example, residue #54 of the $V_H$ of PTA021_A2 can be "backmutated" from aspartic acid to asparagine. Such "backmutated" antibodies are also intended to be encompassed by the invention.

As yet another example, for PTA021_A2, amino acid residue #89 of $V_H$ is an isoleucine (SEQ ID NO:20) whereas this residue in the corresponding $V_H$ 2-05 germline sequence is a threonine (SEQ ID NO:32). To return the framework region sequences to their germline configuration, for example, residue #89 within FR1 of the $V_H$ of PTA021_A2 can be "backmutated" from isoleucine to threonine. Such "backmutated" antibodies are also intended to be encompassed by the invention.

As another example, for PTA021_A3, amino acid residue #54 of $V_H$ is an aspartic acid (SEQ ID NO:21) whereas this residue in the corresponding $V_H$ 2-05 germline sequence is an asparagine (SEQ ID NO:33). To return the framework region sequences to their germline configuration, for example, residue #54 of the $V_H$ of PTA021_A3 can be "backmutated" from aspartic acid to asparagine. Such "backmutated" antibodies are also intended to be encompassed by the invention.

As another example, for PTA021_A3, amino acid residue #77 of $V_K$ is an asparagine (SEQ ID NO:24) whereas this residue in the corresponding $V_K$ L15 germline sequence is a serine (SEQ ID NO:36). To return the framework region sequences to their germline configuration, for example, residue #77 of the $V_K$ of PTA021_A1 can be "backmutated" from asparagine to serine. Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

In another embodiment, the antibody is produced as a UniBody as described in WO/2007/059782 which is incorporated herein by reference in its entirety.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Antibody Physical Properties

The antibodies of the present invention may be further characterized by the various physical properties of the anti-CADM1 antibodies. Various assays may be used to detect and/or differentiate different classes of antibodies based on these physical properties.

In some embodiments, antibodies of the present invention may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison S L (2004) *J Immunol* 172:5489-94; Wallick et al (1988) *J Exp Med* 168:1099-109; Spiro R G (2002) *Glycobiology* 12:43 R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-CADM1 antibody that does not contain variable region glycosylation. This can be achieved either by selecting antibodies that do not contain the glycosylation motif in the variable region or by mutating residues within the glycosylation motif using standard techniques well known in the art.

As an example of glycosylation, for PTA021_A1, using the Kabat numbering system, amino acid residue #30 (within FR3) of $V_H$ is an asparagine (SEQ ID NO:19). This is a potential glycosylation site and this residue can be mutated to a glutamine.

In a preferred embodiment, the antibodies of the present invention do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-CADM1 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present invention is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-CADM1 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-CADM1 antibodies having $V_H$ and $V_K$ sequences disclosed herein can be used to create new anti-CADM1 antibodies by modifying the $V_H$ and/or $V_K$ sequences, or the constant region(s) attached thereto. Thus, in another aspect of the invention, the structural features of an anti-CADM1 antibody of the invention, e.g. PTA021_A1, PTA021_A2, or PTA021_A3, are used to create structurally related anti-CADM1 antibodies that retain at least one functional property of the antibodies of the invention, such as binding to human CADM1. For example, one or more CDR regions of PTA021_A1, PTA021_A2, or PTA021_A3, or mutations thereof, can be combined recombinantly with known framework regions and/or other CDRs to create additional, recombinantly-engineered, anti-CADM1 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-CADM1 antibody comprising:
providing: (i) a heavy chain variable region antibody sequence comprising a CDR1 sequence selected from the group consisting of SEQ ID NOs:1, 2, and 3, a CDR2 sequence selected from the group consisting of SEQ ID NOs:

4, 5, and 6, and/or a CDR3 sequence selected from the group consisting of SEQ ID NOs:7, 8, and 9; and/or (ii) a light chain variable region antibody sequence comprising a CDR1 sequence selected from the group consisting of SEQ ID NOs: 10, 11, and 12, a CDR2 sequence selected from the group consisting of SEQ ID NOs:13, 14, and 15, and/or a CDR3 sequence selected from the group consisting of SEQ ID NOs: 16, 17, and 18;

altering at least one amino acid residue within the heavy chain variable region antibody sequence and/or the light chain variable region antibody sequence to create at least one altered antibody sequence; and expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CADM1 antibodies described herein, which functional properties include, but are not limited to: binds to human CADM1 with a $K_D$ of $1 \times 10^{-7}$ M or less; binds to human CHO cells transfected with CADM1.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-CADM1 antibody coding sequence and the resulting modified anti-CADM1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acids encoding the antibody can be recovered from the library.

Preferred nucleic acids molecules of the invention are those encoding the $V_H$ and $V_L$ sequences of the PTA021_A1, PTA021_A2, or PTA021_A3 monoclonal antibodies. DNA sequences encoding the $V_H$ sequences of PTA021_A1, PTA021_A2, and PTA021_A3 are shown in SEQ ID NOs: 25, 26, and 27, respectively. DNA sequences encoding the $V_K$ sequences of PTA021_A1, PTA021_A2, and PTA021_A3 are shown in SEQ ID NOs: 28, 29, and 30, respectively.

Other preferred nucleic acids of the invention are nucleic acids having at least 80% sequence identity, such as at least 85%, at least 90%, at least 95%, at least 98% or at least 99% sequence identity, with one of the sequences shown in SEQ ID NOs: 25, 26, 27, 28, 29, and 30, which nucleic acids encode an antibody of the invention, or an antigen-binding portion thereof.

The percent identity between two nucleic acid sequences is the number of positions in the sequence in which the nucleotide is identical, taking into account the number of gaps and the length of each gap, which need to be introduced for optimal alignment of the two sequences. The comparison of sequences and determination of percent identity between two sequences can be accomplished using a mathematical algorithm, such as the algorithm of Meyers and Miller or the XBLAST program of Altschul described above.

Still further, preferred nucleic acids of the invention comprise one or more CDR-encoding portions of the nucleic acid sequences shown in SEQ ID NOs:25, 26, 27, 28, 29, and 30. In this embodiment, the nucleic acid may encode the heavy chain CDR1, CDR2 and/or CDR3 sequence of PTA021_A1, PTA021_A2, or PTA021_A3 or the light chain CDR1, CDR2 and/or CDR3 sequence of PTA021_A1, PTA021_A2, or PTA021_A3.

Nucleic acids which have at least 80%, such as at least 85%, at least 90%, at least 95%, at least 98% or at least 99% sequence identity, with such a CDR-encoding portion of SEQ ID NO: 25, 26, 27, 28, 29, or 30 (VH and VK seqs) are also preferred nucleic acids of the invention. Such nucleic acids may differ from the corresponding portion of SEQ ID NO: 25, 26, 27, 28, 29, or 30 in a non-CDR coding region and/or in a CDR-coding region. Where the difference is in a CDR-coding region, the nucleic acid CDR region encoded by the nucleic acid typically comprises one or more conservative sequence modification as defined herein compared to the corresponding CDR sequence of PTA021_A1, PTA021_A2, or PTA021_A3.

Once DNA fragments encoding $V_H$ and $V_K$ segments are obtained, these DNA fragments can be further manipulated by standard recombinant DNA techniques, for example to convert the variable region genes to full-length antibody chain genes, to Fab fragment genes or to a scFv gene. In these manipulations, a $V_K$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L/V_K$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_L/V\kappa$-encoding DNA fragments are operatively linked to another fragment encoding a flexible linker, e.g., encoding the amino acid sequence (Gly$_4$-Ser)$_3$ (SEQ ID NO: 46), such that the $V_H$ and $V_L/V_K$ sequences can be expressed as a contiguous single-chain protein, with the $V_L/V_K$ and $V_H$ regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against CADM1 can be generated using transgenic or transchromosomic mice carrying parts of the human immune system rather than the mouse system. These transgenic and transchromosomic mice include mice referred to herein as mice of the HuMAb Mouse® and KM Mouse® strains, respectively, and are collectively referred to herein as "human Ig mice."

The HuMAb Mouse® strain (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse®, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchromosomes, such as a mouse that carries a human heavy chain transgene and a human light chain transchromosome. This mouse is referred to herein as a mouse of the "KM Mouse®" strain, and is described in detail in PCT Publication WO 02/43478 to Ishida et al.

Still further, alternative transgenic animal systems expressing human immunoglobulin genes are available in the art and can be used to raise anti-CADM1 antibodies of the invention. For example, an alternative transgenic system referred to as the Xenomouse (Amgen, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CADM1 antibodies of the invention. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and PCT application No. WO/2002/092812 and can be used to raise anti-CADM1 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of CADM1 antigen and/or recombinant CADM1, or cells expressing CADM1, or a CADM1 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 µg) of CADM1 antigen can be used to immunize the human Ig mice intraperitoneally.

Detailed procedures to generate fully human monoclonal antibodies to CADM1 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CADM1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. In one embodiment, mouse strains bearing an HCo7, HCo12 or HCo17 human heavy chain transgene strains may used. Alternatively or additionally, the KM Mouse® strain can be used. In addition, two or more of these strains can be bred together into a single mouse having a plurality of different human heavy chain transgenes.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to CADM1 by, for example, standard ELISA. Briefly, microtiter plates are coated with purified CADM1 at 0.25 μg/ml in PBS, and then blocked with 5% bovine serum albumin in PBS. Dilutions of antibody (e.g., dilutions of plasma from CADM1-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with CADM1 immunogen. Hybridomas that bind with high avidity to CADM1 are subcloned and further characterized. One clone from each hybridoma, which retains the reactivity of the parent cells (by ELISA), can be chosen for making a 5-10 vial cell bank stored at −140° C., and for antibody purification.

To purify anti-CADM1 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CADM1 monoclonal antibodies bind to unique epitopes, each antibody can be biotinylated using commercially available reagents (Pierce, Rockford, Ill.). Studies for competing for binding with the antibodies of the invention using unlabeled monoclonal antibodies and biotinylated monoclonal antibodies can be performed using CADM1 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CADM1 human IgGs can be further tested for reactivity with CADM1 antigen by Western blotting. Briefly, CADM1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

The binding specificity of an antibody of the invention may also be determined by monitoring binding of the antibody to cells expressing CADM1, for example by flow cytometry. Typically, a cell line, such as a CHO cell line, may be transfected with an expression vector encoding a transmembrane form of CADM1. In some embodiments, a full length CADM1 molecule with an amino terminal HA tag (SEQ ID NO:43) is expressed on the cell surface of the CHO cell line. The transfected protein may comprise a tag, such as a myc-tag, preferably at the N-terminus, for detection using an antibody to the tag. Binding of an antibody of the invention to CADM1 may be determined by incubating the transfected cells with the antibody, and detecting bound antibody. Binding of an antibody to the tag on the transfected protein may be used as a positive control.

The specificity of an antibody of the invention for CADM1 may be further studied by determining whether or not the antibody binds to other proteins, such as TSLL2/CADM1C or other members of the immunoglobulin superfamily using the same methods by which binding to CADM1 is determined.

Antibody-Partner Molecule Conjugates

In a preferred aspect, there is provided a conjugate comprising an anti-CADM1 antibody according to this invention and a partner molecule, the conjugate being represented by formula (a)

$$Z[(X^Z)_a C(X^D)_b D]_m \quad (a)$$

where Z is an antibody according to this invention; D is a partner molecule; and $(X^Z)_a C(X^D)_b$ are collectively referred to as a "linker moiety" or "linker" because they link the first two elements. Within the linker, C is a cleavable group designed to be cleaved at the site of intended biological action of partner molecule D; $X^Z$ and $X^D$ are referred to as spacer moieties (or "spacers") because they space apart Z and C and C and D, respectively; subscripts a and b are independently 0 or 1 (that is, the presence of $X^Z$ and/or $X^D$ is optional); and subscript m is 1, 2, 3, 4, 5, 6, 7, 8, 9, or 10 (preferably 1, 2, 3, or 4). Each of the foregoing terms is more fully defined herein below.

Antibody Z serves a targeting function: by binding to a target tissue or cell where its antigen is located, it directs the conjugate there. Preferably, the target tissue or cell is a tumor or a cancer cell and the antigen is a tumor-associated or tumor-specific antigen. Cleavage of group C at the target tissue or cell releases partner molecule D to perform its intended biological function. In some instances, the conjugate is internalized into a target cell by endocytosis and cleavage takes place within the target cell. In this manner, precise delivery of partner molecule D is achieved at the site of action, reducing the dosage needed. Also, partner molecule D is normally biologically inactive (or significantly less active) in its conjugated state, thereby reducing undesired toxicity against non-target tissue or cells. As anticancer drugs are often highly toxic compounds with a low therapeutic index, this is an important consideration.

As reflected by the subscript m, each molecule of antibody Z can conjugate with more than one partner molecule D, depending on the number of sites the former has available for conjugation and the experimental conditions employed. Those skilled in the art will appreciate that, while each molecule of antibody Z is conjugated to an integer number of partner molecules D, a preparation of the conjugate may analyze for a non-integer ratio of partner molecules D to antibody Z, reflecting a statistical average.

Antibody Z

Any one of several different reactive groups on antibody Z can be used as a conjugation site, including ϵ-amino groups in lysine residues, pendant carbohydrate moieties, carboxylic acid groups, disulfide groups, and thiol groups. Each type of reactive group represents a trade-off, having some advantages but some countervailing limitations. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, antibody Z is conjugated via a lysine ϵ-amino group. Most antibodies have multiple exposed lysine ϵ-amino groups, which can be conjugated via amide, urea, thiourea, or carbamate bonds using techniques known in the art, including modification with a heterobifunctional agent (as further described herein below). However, it is difficult to control which and how many ϵ-amino groups react, leading to potential batch-to-batch variability in conjugate preparations. Also, conjugation may cause neutralization of a protonated ϵ-amino group important for maintaining the antibody's native conformation or may take place at a lysine near or at the antigen binding site, neither being a desirable occurrence.

In another embodiment, antibody Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be reduced with sodium cyanoborohydride to produce a more stable bond. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ϵ-amino groups, there are concerns regarding location of the conjugation site(s) and stoichiometry.

In yet another embodiment, antibody Z can be conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging the sulfur of a cysteine residue on antibody Z and a sulfur on the other portion of the conjugate. Some antibodies (such as the IgG isotype) lack free thiol groups but have disulfide groups, for example in the hinge region. In such case, free thiol groups can be generated by reduction of native disulfide groups. The thiol groups so generated can then be used for conjugation. See, for example, Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding the conjugation location and stoichiometry and the possible disruption of antibody native conformation.

In yet another preferred embodiment, antibody Z is conjugated via the nucleophilic addition product of a thiol group to an acceptor moiety. A preferred acceptor moiety is a maleimide group, whose reaction with an antibody thiol group is illustrated below:

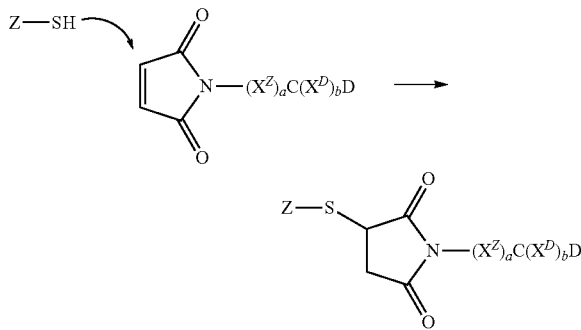

A number of methods have been developed to introduce free thiol groups into antibodies without breaking native disulfide bonds, which methods can be practiced with an antibody Z of this invention. Depending on the method employed, it may be possible to introduce a predictable number of free sulfhydryls at specific locations. In one approach, mutated antibodies are prepared in which a cysteine is substituted for another amino acid. See, for example, Eigenbrot et al., US 2007/0092940 A1; Chilkoti et al., *Bioconjugate Chem.* 1994, 5, 504-507; Urnovitz et al., U.S. Pat. No. 4,698,420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus. See, e.g. Cumber et al., *J. Immunol.*, 149, 120-126 (1992); King et al, *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by King, in U.S. Provisional Application Ser. No. 60/957,271, filed Aug. 22, 2007, in which a cysteine bearing amino acid sequence is added to the C-terminus of the heavy chain of an antibody. This method introduces a known number of cysteine residues (one per heavy chain) at a known location remote from the antigen binding site. The disclosures of the documents cited in this paragraph are all incorporated herein by reference.

In yet another embodiment, lysine ε-amino groups can be modified with heterobifunctional reagents such as 2-iminothiolane or N-succinimidyl-3-(2-pyridyldithio)propionate (SPDP), converting an ε-amino group into a thiol or disulfide group—creating a cysteine surrogate, as it were. However, this method suffers from the same conjugation location and stoichiometry limitations associated with ε-amino groups proper.

Partner Molecule D

Partner molecule D can be a therapeutic agent or a marker. If the former, it can be, for example, a cytotoxin, a non-cytotoxic drug (e.g., an immunosuppressant), a radioactive agent, another antibody, or an enzyme or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. If the latter, it can be any moiety that generates a detectable signal, such as a radiolabel, a fluorescent label, or an enzyme that catalyzes a detectable modification to a substrate. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of the invention.

A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, 1-dehydrotestosterone, glucocorticoids, procaine, tetracaine, lidocaine, propranolol, and puromycin and analogs or homologs thereof.

Where partner molecule D is a therapeutic agent, suitable classes of therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. Examples of suitable therapeutic agents include actinomycin D, anthracyclines, anthramycin (AMC), auristatin, bleomycin, busulfan, calicheamicin, camptothecin, carmustine, chlorambucil, cis-dichlorodiamine platinum (II) (DDP), cisplatin, colchicin, cyclophosphamide, cytarabine, cytochalasin B, dactinomycin, daunorubicin, decarbazine, 1-dehydrotestosterone, dibromomannitol, dihydroxyanthracindione, doxorubicin, emetine, epothilone, ethidium bromide, etoposide, 5-fluorouracil, gemcitabine, glucocorticoids, gramicidin D, imatinib, irinotecan, β-lapachone, lidocaine, lomustine, maytansine, mechlorethamine, melphalan, 6-mercaptopurine, methotrexate, mithramycin, mitomycin C, mitoxantrone, paclitaxel, procaine, propranolol, puromycin, ricin, streptozotocin, suberoylanilide hydroxamic acid (SAHA), tallisomycin, tenoposide, tetracaine, thioepa, 6-thioguanine, tubulysin, vinblastine, vincristine, and analogs, homologs or derivatives thereof.

Preferably, partner molecule D is a cytotoxin selected from the group consisting of auristatins (especially MMAE and MMAF), enediyne antibiotics (especially calicheamicin and CalichDMH), doxorubicin, maytansinoids (especially DM1 and DM4), *Pseudomonas* exotoxin A (especially its truncated form), DNA minor groove-binding alkylators (especially CC-1065 and duocarmycin analogs), and analogs or derivatives thereof. An example of a calicheamicin antibody conjugate is commercially available (Mylotarg®; American Home Products). Those skilled in the art will appreciate that the foregoing cytotoxins are mostly natural products and that some modification thereof—i.e., derivatization—may be desirable or necessary to render them ready for conjugation.

A preferred DNA minor groove-binding alkylators is an analog or a derivative of CC-1065 and the structurally related duocarmycins, suitable examples of which are disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1 (2002); Boyd et al., US 2006/0024317 A1 (2006); Chen et al., US 2006/0004081 A1 (2006); Gangwar et al., US 2006/0247295 A1 (2006); Boyd et al., WO 2007/038658 A2 (2007); Gangwar et al., WO 2007/051081 A1 (2007); Gangwar et al., WO 2007/

059404 A2 (2007); Sufi et al., WO 2008/083312 A2 (2008); and Chen et al., PCT Application No. PCT/US2008/054362, filed Feb. 20, 2008; the disclosures of which are incorporated herein by reference. Such preferred partner molecules D can be represented by formula (b):

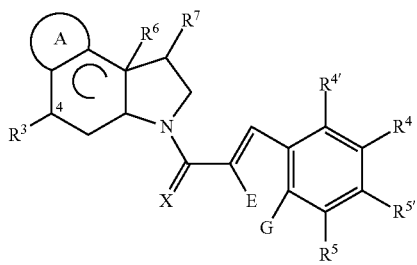

(b)

wherein ring system A is a substituted or unsubstituted aryl, a substituted or unsubstituted heteroaryl, a substituted or unsubstituted heterocycloalkyl group, such as phenyl or pyrrole;

E and G are independently H, substituted or unsubstituted alkyl, substituted or unsubstituted heteroalkyl, a heteroatom, or a single bond, or E and G are join to form a ring system selected from substituted or unsubstituted aryl, substituted or unsubstituted heteroaryl and substituted or unsubstituted heterocycloalkyl;

X is O, S or $NR^{23}$, where $R^{23}$ is a H, substituted or unsubstituted alkyl, substituted or unsubstituted heteroalkyl, or acyl;

$R^3$ is (=O) or OH;

$R^4$, $R^{4'}$, $R^5$ and $R^{5'}$ are independently H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(=O)NR^{15}R^{16}$, $OC(=O)OR^{15}$, $C(=O)R^{15}$, $SR^{15}$, $OR^{15}$, $CR^{15}=NR^{16}$, or $O(CH_2)_nN(CH_3)_2$, where n is an integer from 1 to 20, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members;

$R^{15}$ and $R^{16}$ are independently H, substituted or unsubstituted alkyl, substituted or unsubstituted heteroalkyl, substituted or unsubstituted aryl, substituted or unsubstituted heteroaryl, substituted or unsubstituted heterocycloalkyl or substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

$R^6$ is a single bond which is either present or absent;

$R^7$ is $CH_2$—$X^1$ or —$CH_2$—, with the proviso that when $R^6$ is present, $R^6$ and $R^7$ are joined to form a cyclopropyl ring; and $X^1$ is a leaving group such as Cl, Br, F, mesylate, or tosylate.

A partner molecule of formula (b) can be conjugated via one of $R^3$, $R^4$, $R^{4'}$, $R^5$, and $R^{5'}$, preferably via $R^3$ (when $R^3$ is OH) or $R^4$, more preferably via $R^4$. Also, $R^3$ can carry a prodrugging moiety, as discussed herein below.

A preferred partner molecule of formula (b) is represented by formula (c):

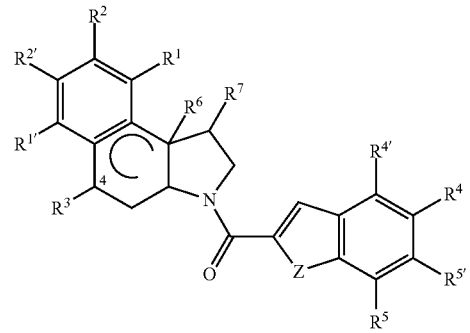

(c)

wherein $R^3$, $R^4$, $R^{4'}$, $R^5$, $R^{5'}$, $R^6$, and $R^7$ are as defined hereinabove;

Z is O, NH, or N(lower alkyl); and $R^1$, $R^{1'}$, $R^2$, and $R^{2'}$ are independently H, substituted or unsubstituted lower alkyl, cyano, alkoxy, halogen, $C(=O)R^8$, or $CO_2R^8$, wherein $R^8$ is $NR^9R^{10}$ or $OR^9$, wherein $R^9$ and $R^{10}$ are independently H, substituted or unsubstituted alkyl, or substituted or unsubstituted heteroalkyl.

A more preferred embodiment is shown in formula (d):

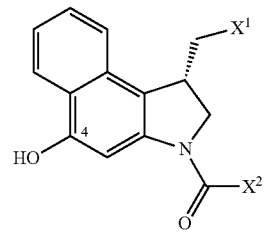

(d)

wherein $X^1$ is as previously defined and $X^2$ is

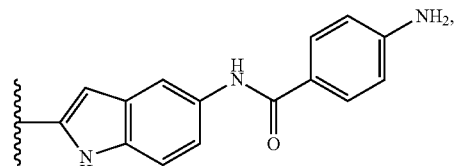

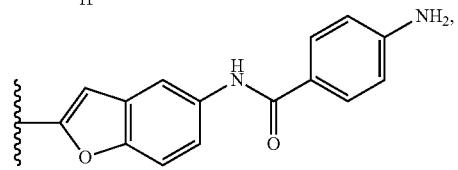

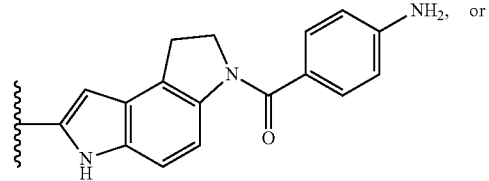

or

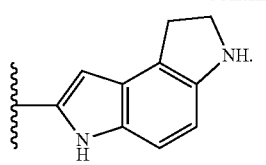

An example of a specific partner molecule D is represented by formula (e):

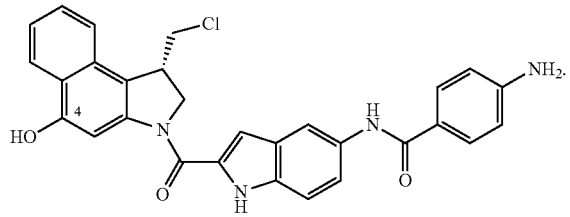

(e)

Where partner molecule D is a cytotoxin, it can be prodrugged, that is, have attached to it a prodrug moiety whose removal is required to activate it. Preferably, the prodrug group (1) is removed by a reaction mechanism different from that for cleaving the cytotoxin from the conjugate, (2) is not removed or is only slowly removed while the conjugate is in circulation in the blood plasma, but (3) is efficiently removed at the target tissue or cell. Consequently, if the conjugate is adventitiously cleaved before reaching the target tissue or cell, the cytotoxin is released in its still-inactive prodrug form, eliminating or reducing cytotoxicity towards non-target tissues or cells. That is, the requirement for a second cleavage to activate the cytotoxin provides a safety factor. In the instance of a cytotoxin according to formulae (b), (c), (d) or (e), a preferred site for attachment of a prodrug group is at the position labeled with a "4". To increase the safety factor where cleavage of group C and removal of the prodrug moiety are both mediated by enzymes, it is preferable that different enzymes be involved.

Non-limiting examples of prodrug groups include esters, carbamates, phosphates, and glycosides. To illustrate, the 4-position hydroxyl in the cytotoxins of formulae ((b)-(e) can be prodrugged with the following prodrug moieties:

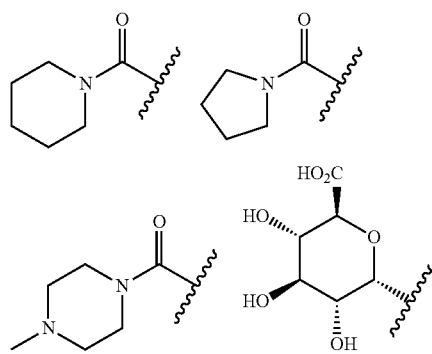

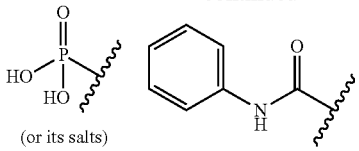

(or its salts)

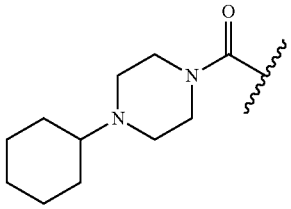

Partner molecule D can also be a marker. The marker can be any label that generates a detectable signal, such as a radiolabel, a fluorescent label, or an enzyme that catalyzes a detectable modification to a substrate. Markers (also called reporter groups or detectable labels) are well known in the area of immunoassays, biomedical research, and medical diagnosis and can be detected by spectroscopic, photochemical, biochemical, immunochemical, electrical, optical, or chemical means. The marker is preferably a radioactive isotope, a fluorescent or chemiluminescent agent or precursor thereof, a chromophore, an enzyme, or combinations thereof. Examples of suitable enzymes are horseradish peroxidase, alkaline phosphatase, β-galactosidase, and glucose oxidase. Fluorescent agents include fluorescein and its derivatives, rhodamine and its derivatives, dansyl, umbelliferone, etc. Chemiluminescent compounds include luciferin and 2,3-dihydrophthalazinediones such as luminol.

Linker —$(X^Z)_a C(X^D)_b$—

As noted above, the linker portion of a conjugate of this invention comprises up to three elements: a cleavable group C and optional spacers $X^Z$ and $X^D$.

Cleavable group C is selected such that it is relatively stable while the conjugate is in general circulation in the blood plasma, but is readily cleaved once the conjugate reaches its site of intended action. Preferably, the conjugate is internalized by endocytosis by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl. Acad. Sci. (USA)*, 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., US 2005/0287155 A1 (2005); Ng et al., U.S. Pat. No. 6,989,452 B2 (2006); Ng et al., WO 2002/096910 A1 (2002); Boyd et al., US 2006/0024317 A1 (2006); and Sufi et al., WO 2008/083312 A2 (2008); the disclosures of which are incorporated herein by reference.

A preferred group C comprises a peptide bond that is cleaved preferentially by a protease at the intended site of action, as opposed to by a protease in the serum. Typically, group C comprises from 1 to 20 amino acids, preferably from 1 to 6 amino acids, more preferably from 1 to 3 amino acids. The amino acid(s) can be natural and/or unnatural α-amino acids. Natural amino acids are those encoded by the genetic code, as well as amino acids derived therefrom, e.g., hydroxyproline, γ-carboxyglutamate, citrulline, and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The term "unnatural amino acid" is intended to represent the "D" stereochemical form, the natural amino acids being of the "L" form.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence $-AA^2-AA^1-$ where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N-AA^2-AA^1-CO_2H$, unless the context clearly indicates otherwise.) For additional information regarding cathepsin-cleavable groups, see Dubowchik et al., *Biorg. Med. Chem. Lett.* 8, 3341-3346 (1998); Dubowchik et al., *Biorg. Med. Chem. Lett.*, 8 3347-3352 (1998); and Dubowchik et al., *Bioconjugate Chem.* 13, 855-869 (2002); the disclosures of which are incorporated by reference.

In one embodiment, Group C is a peptide comprising the two-amino acid sequence $-AA^2-AA^1-$ wherein $AA^1$ is lysine, arginine, or citrulline and $AA^2$ is phenylalanine, valine, alanine, leucine or isoleucine. In another embodiment, C consists of a sequence of one to five amino acids, selected from the group consisting of Val-Cit, Ala-Val, Val-Ala-Val, Lys-Lys, Pro-Val-Gly-Val-Val (SEQ ID NO:45), Ala-Asn-Val, Val-Leu-Lys, Cit-Cit, Val-Lys, Lys, Cit, Ser, and Glu.

The preparation and design of cleavable groups C comprising a single amino acid is further discussed in Chen et al., PCT Application No. PCT/US2008/054362, filed Feb. 20, 2008, the disclosure of which is incorporated herein by reference.

Group C can also be a photocleavable one, for example a nitrobenzyl ether that is cleaved upon exposure to light.

Group C can be bonded directly to antibody Z or partner molecule D; that is, spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain. Or, group C can be a peptide bond formed with a lysine ε-amino group of antibody Z.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

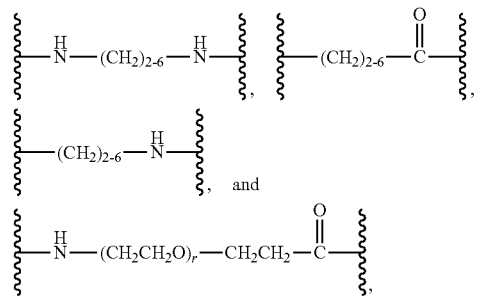

where the subscript r is 1 to 24, preferably 2 to 4. These segments can be combined to make spacers $X^Z$ such as:

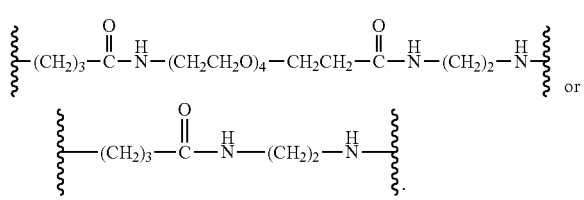

Spacer $X^D$, if present, provides spatial separation between group C and partner molecule D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Either spacer $X^Z$ or $X^D$, or both, can comprise a self-immolating moiety. Briefly, a self-immolating moiety is a moiety that (1) is bonded to group C and either antibody Z or partner molecule D and (2) has a structure such that cleavage of group C initiates a reaction sequence that results in the self-immolating moiety to disbonding itself from antibody Z or partner molecule D, as the case may be. In other words, a reaction at a site distal from antibody Z or partner molecule D (cleavage of group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof remains attached to partner molecule D, the biological activity of the latter may be impaired. The use of a self-immolating moiety is especially preferred where cleavable group C is a polypeptide.

Exemplary self-immolating moieties (i)-(v) bonded to a hydroxyl or amino group on a partner molecule D are shown below:

(i)
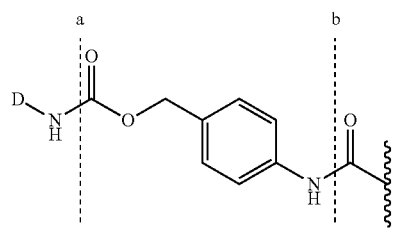

(ii)
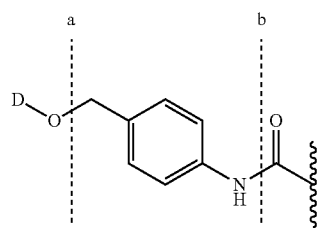

(iii)
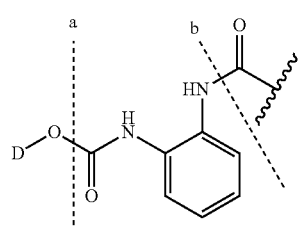

(iv)
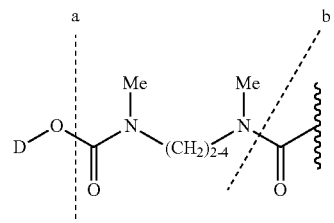

(v)
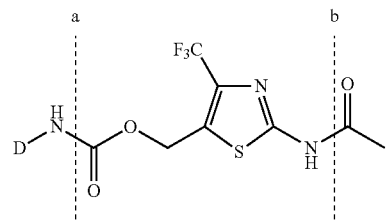

In each instance, the self-immolating moiety is the structure between dotted lines a and b, with adjacent structural features shown to provide context. Self-immolating moieties (i) and (v) are bonded to a partner molecule D-NH$_2$ (i.e., partner molecule D is conjugated via an amino group), while self-immolating moieties (ii), (iii), and (iv) are bonded to a partner molecule D-OH (i.e., partner molecule D is conjugated via a hydroxyl group). Cleavage of the amide bond at dotted line b (i.e., group C is a peptide) releases the amide nitrogen as an amine nitrogen, initiating a reaction sequence that results in the cleavage of the bond at dotted line a and the consequent release of partner molecule D-OH or D-NH$_2$, as the case may be. For additional disclosures regarding self-immolating moieties, see, Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., WO 2005/112919 (2005); Boyd et al., WO 2007/038658 (2007); Sufi et al., WO 2008/083312 A2 (2008); Feng, U.S. Pat. No. 7,375,078 B2 (2008); and Senter et al., US 2003/0096743 A1 (2003); the disclosures of which are incorporated by reference.

Examples of Conjugates

Examples of conjugates made with an antibody Z(SH)$_m$ of this invention (where m is 1, 2, 3, 4, or 5) are shown below. Conjugates A-1 to A-6 and A-8 to A-15 are conjugates in which cleavable group C comprises a peptide bond. Conjugates A-7 and A-16 are conjugates in which cleavable group C is a hydrazone. Conjugates A-17 and A-18 are conjugates in which cleavable group C is a disulfide. In conjugates A-1 to A-2, A-5 to A-9, A-11 to A-14, and A-16, partner molecule D is a cytotoxin having a prodrug moiety attached thereto. Conjugates A-10, A-11, A-14, and A-15 are conjugates having a self-immolating moiety (two in the case of conjugate A-10). Conjugates A-1 through A-8 and A-10 through A-18 illustrate the use of spacers having modular segments.

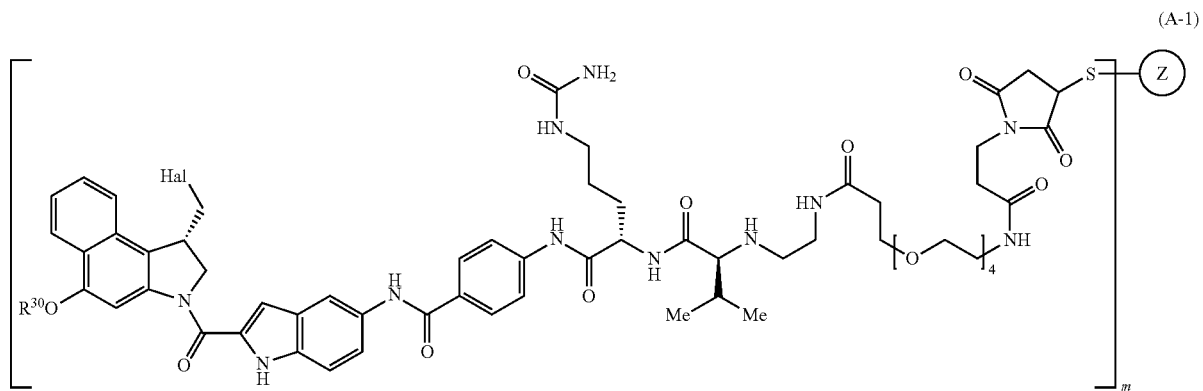
(A-1)
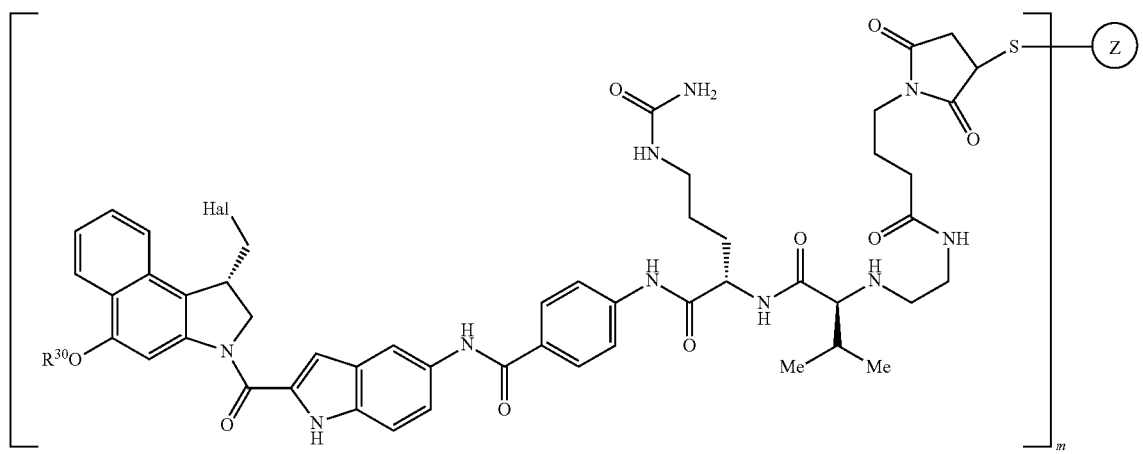
(A-2)
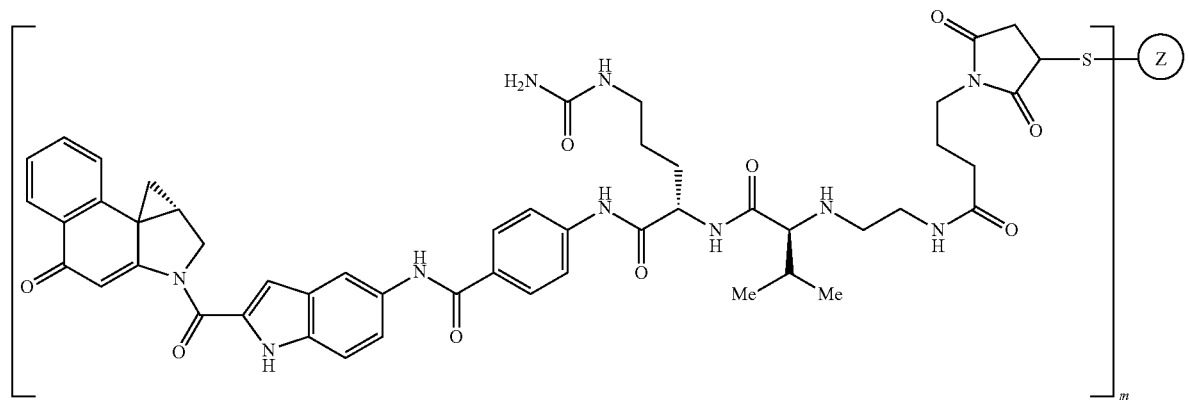
(A-3)

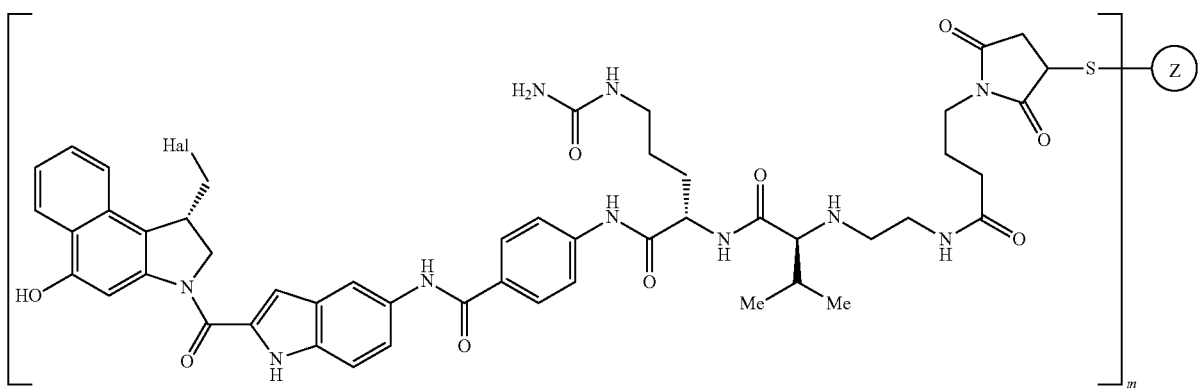
(A-4)
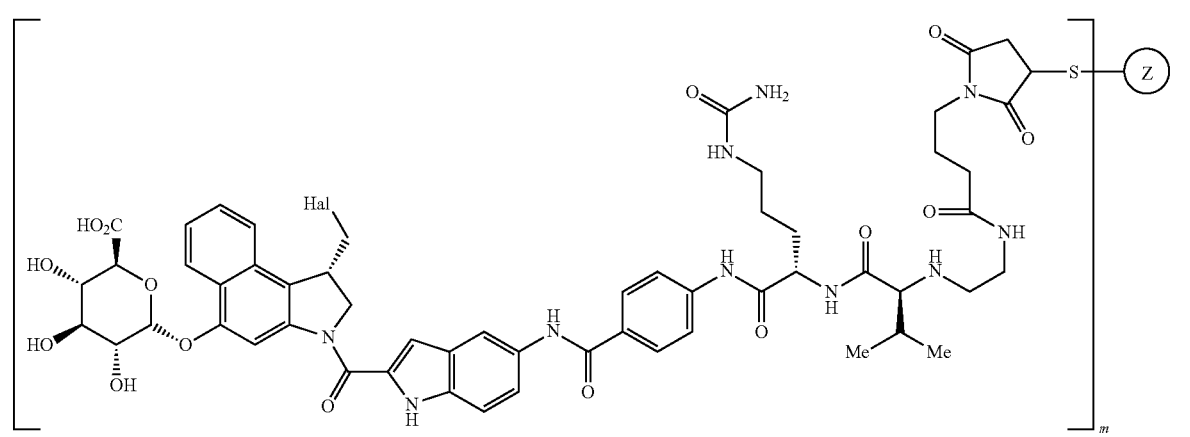
(A-5)
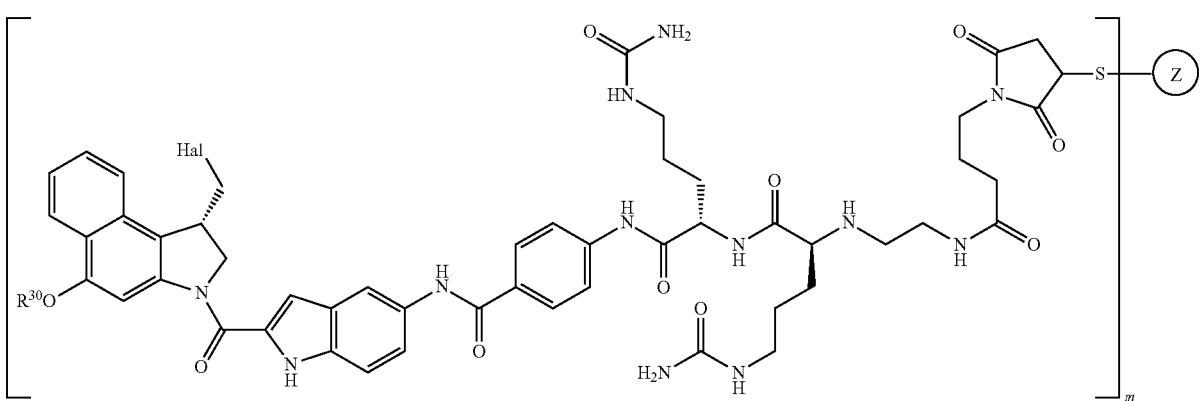
(A-6)

-continued
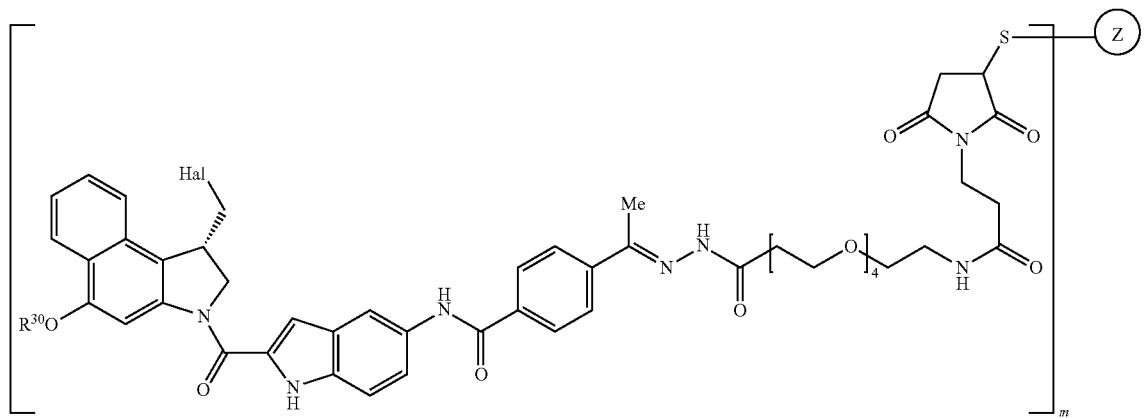
(A-7)
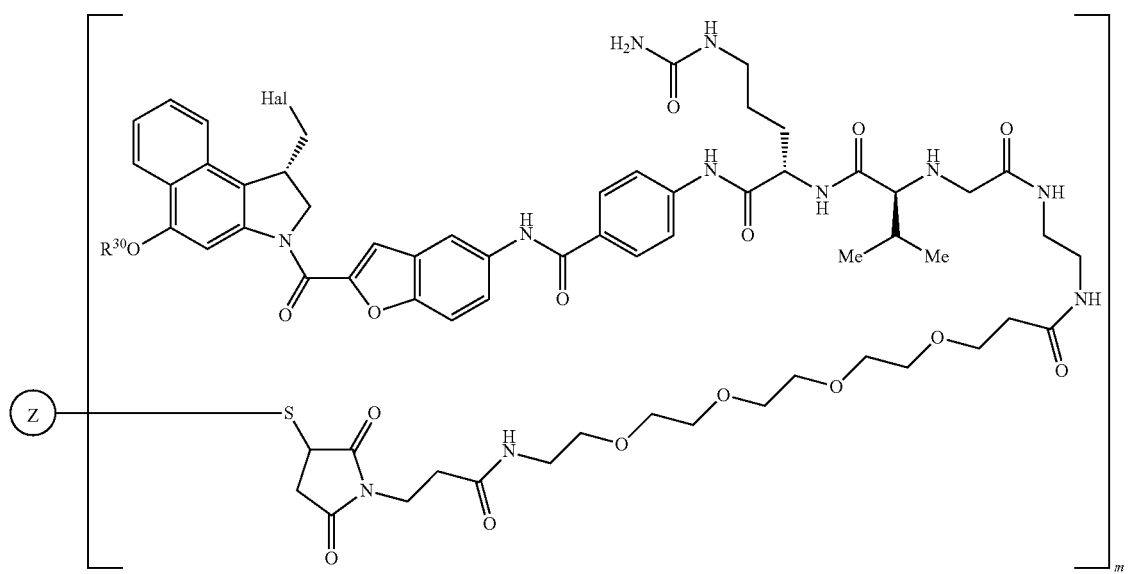
(A-8)
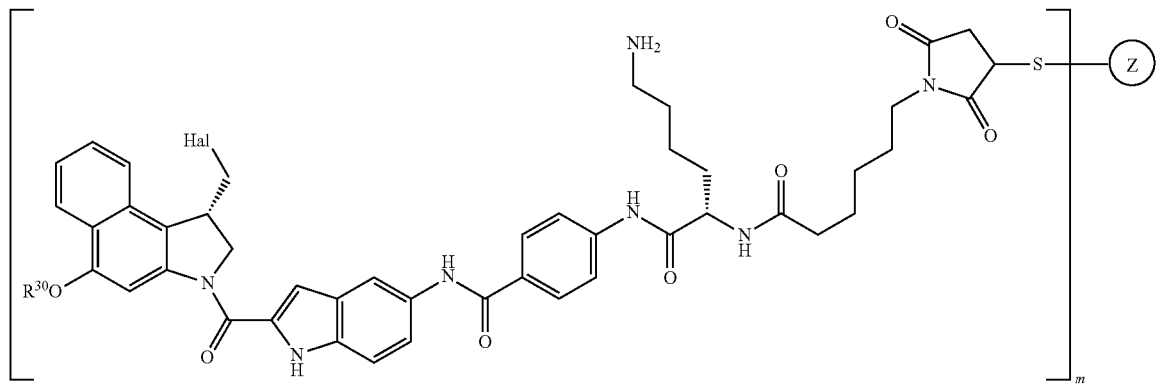
(A-9)

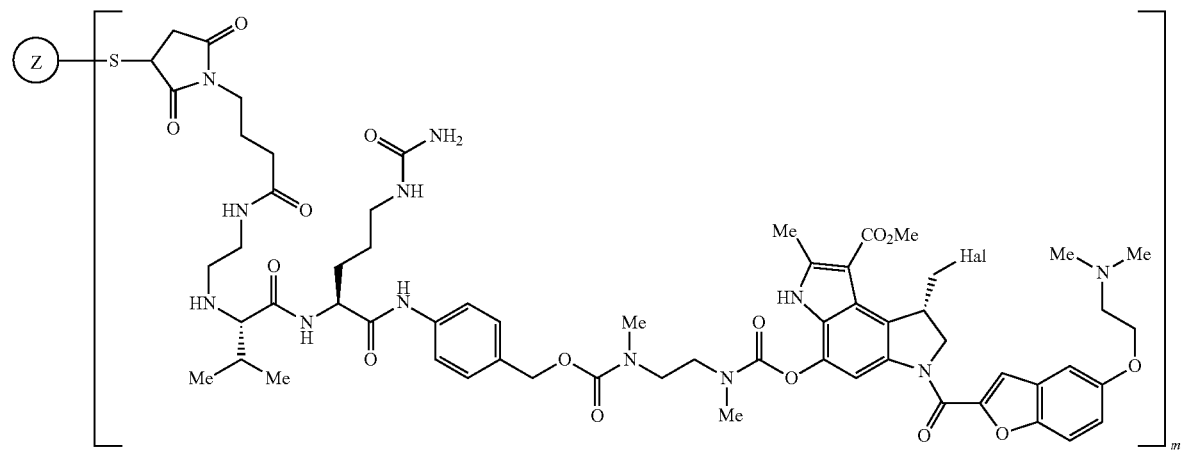
(A-10)
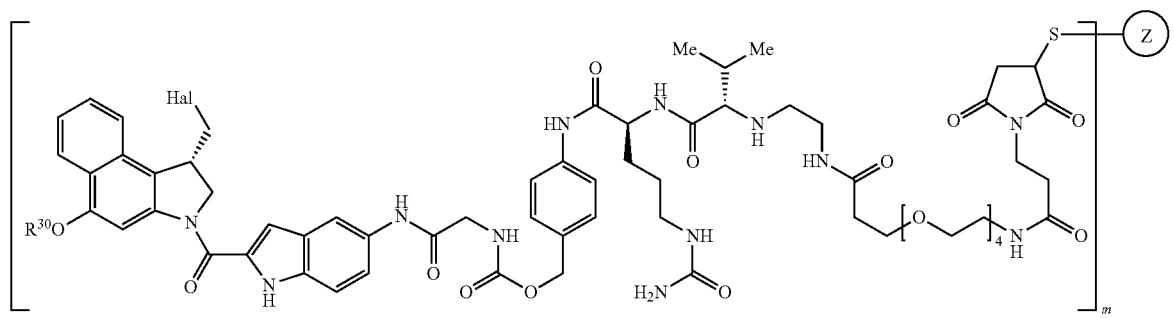
(A-11)
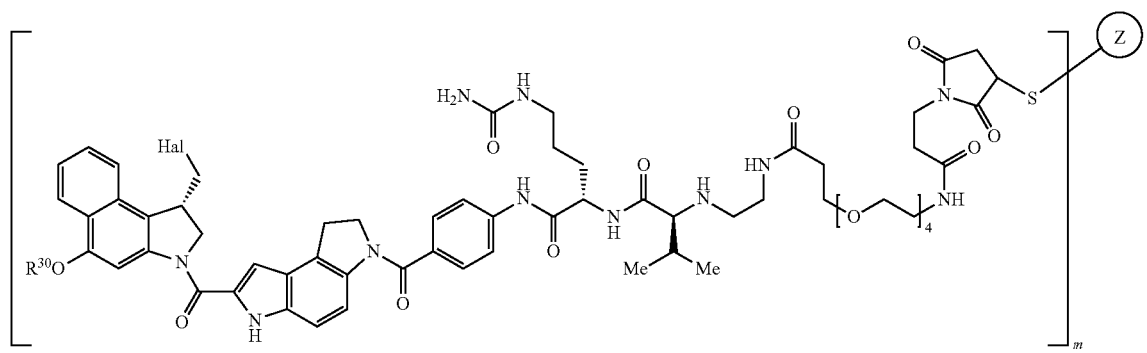
(A-12)
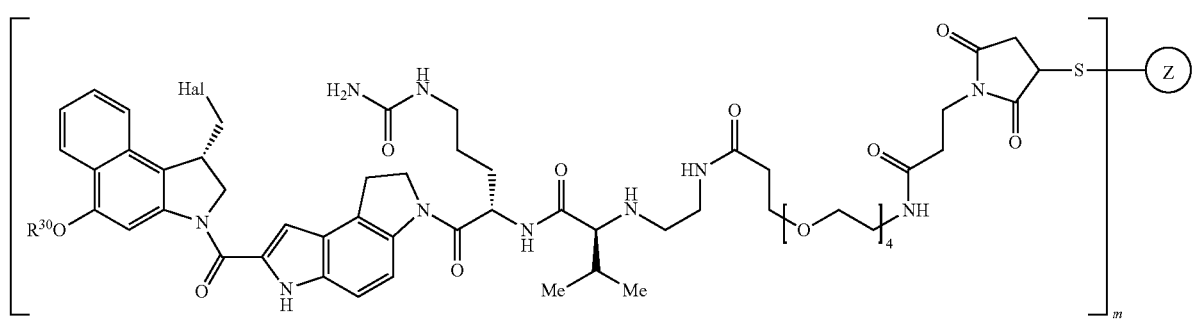
(A-13)

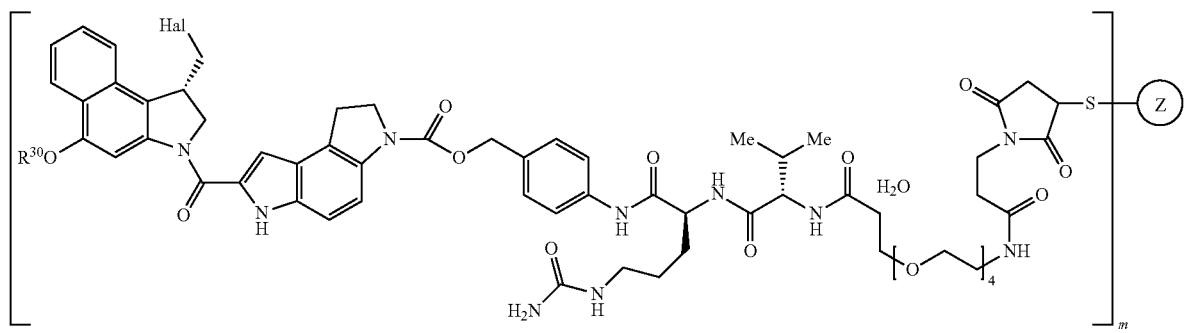
(A-14)
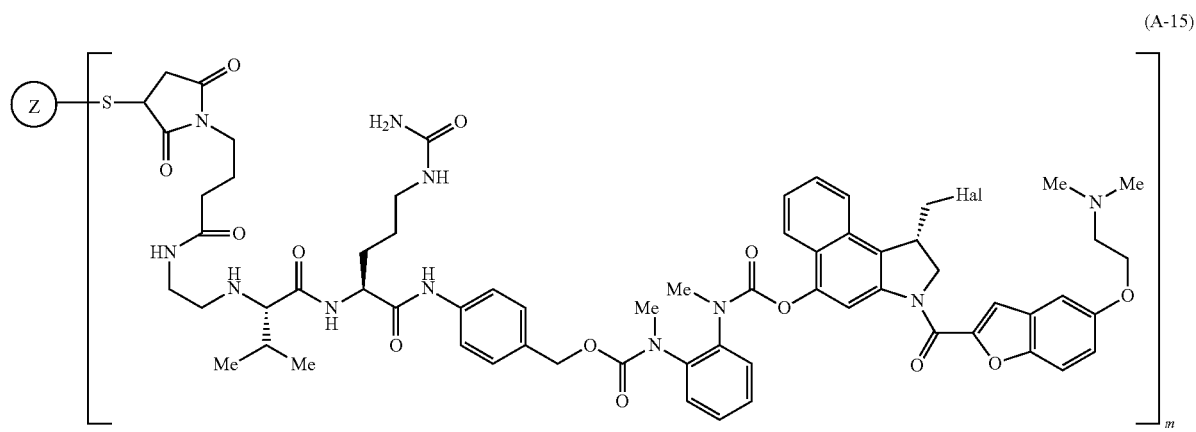
(A-15)
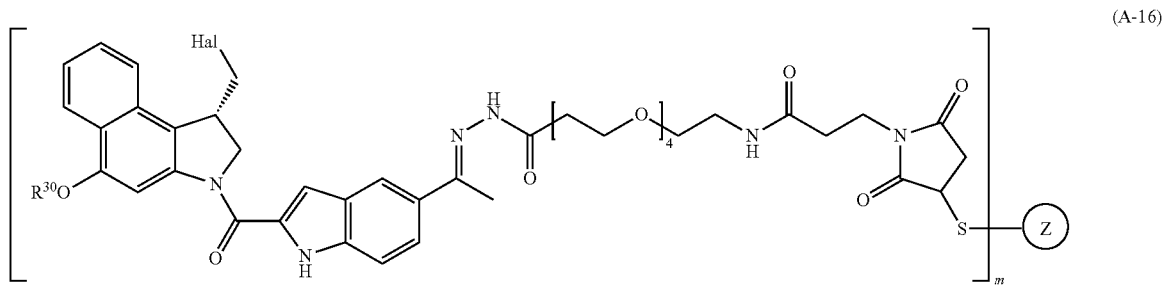
(A-16)
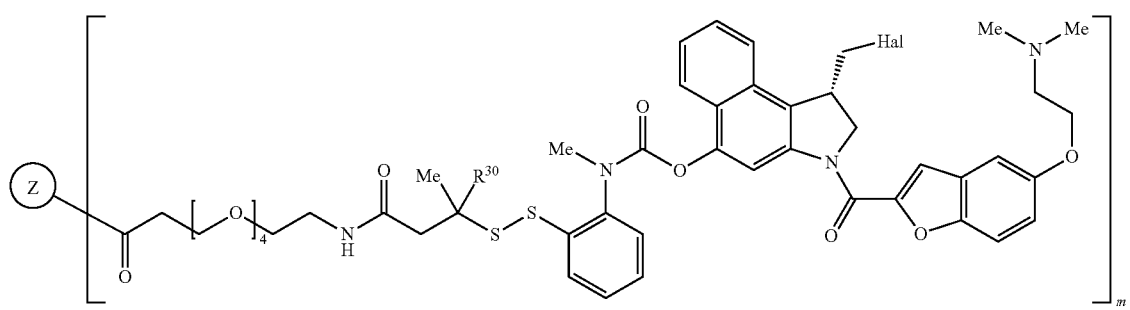
(A-17, $R^{30}$ = H)
(A-18, $R^{30}$ = Me)

Where present in the preceding formulae, Hal is Cl or Br and $R^{30}$ is the carboxyesterase-cleavable carbamate prodrug group shown below:

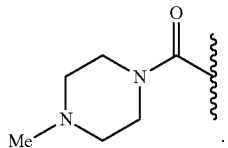 [SMILES: *C(=O)N1CCN(C)CC1]

Preparation of Conjugates

Conjugates of this invention preferably are prepared by first joining partner molecule D and linker $(X^Z)_aC(X^D)_b$ to form a moiety $D\text{-}(X^Z)_aC(X^D)_b\text{—}R^{31}$, where $R^{31}$ is a functional group suitable for reacting with a functional group on antibody Z, to form the conjugate. Examples of suitable groups $R^{21}$ include:

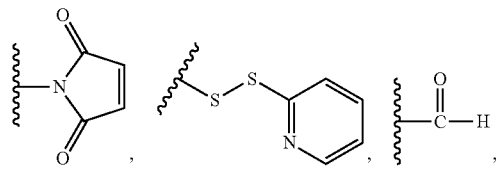

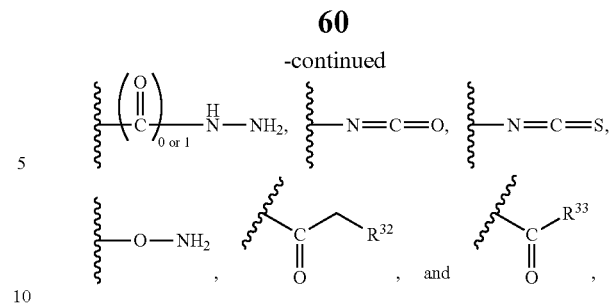

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. The preparation of suitable moieties $D\text{-}(X^Z)_aC(X^D)_b\text{—}R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1 (2002); Boyd et al., US 2006/0024317 A1 (2006); Chen et al., US 2006/0004081 A1 (2006); Gangwar et al., US 2006/0247295 A1 (2006); Boyd et al., WO 2007/038658 A2 (2007); Gangwar et al., WO 2007/051081 A1 (2007); Gangwar et al., WO 2007/059404 A2 (2007); Sufi et al., WO 2008/083312 A2 (2008); and Chen et al., PCT Application No. PCT/US2008/054362, filed Feb. 20, 2008; the disclosures of which are incorporated herein by reference.

In a preferred embodiment (formula M), $R^{31}$ is a maleimide group and the functional group on antibody Z is a thiol group as illustrated following, using conjugate A-2 where Hal is Cl and antibody $Z(SH)_m$:

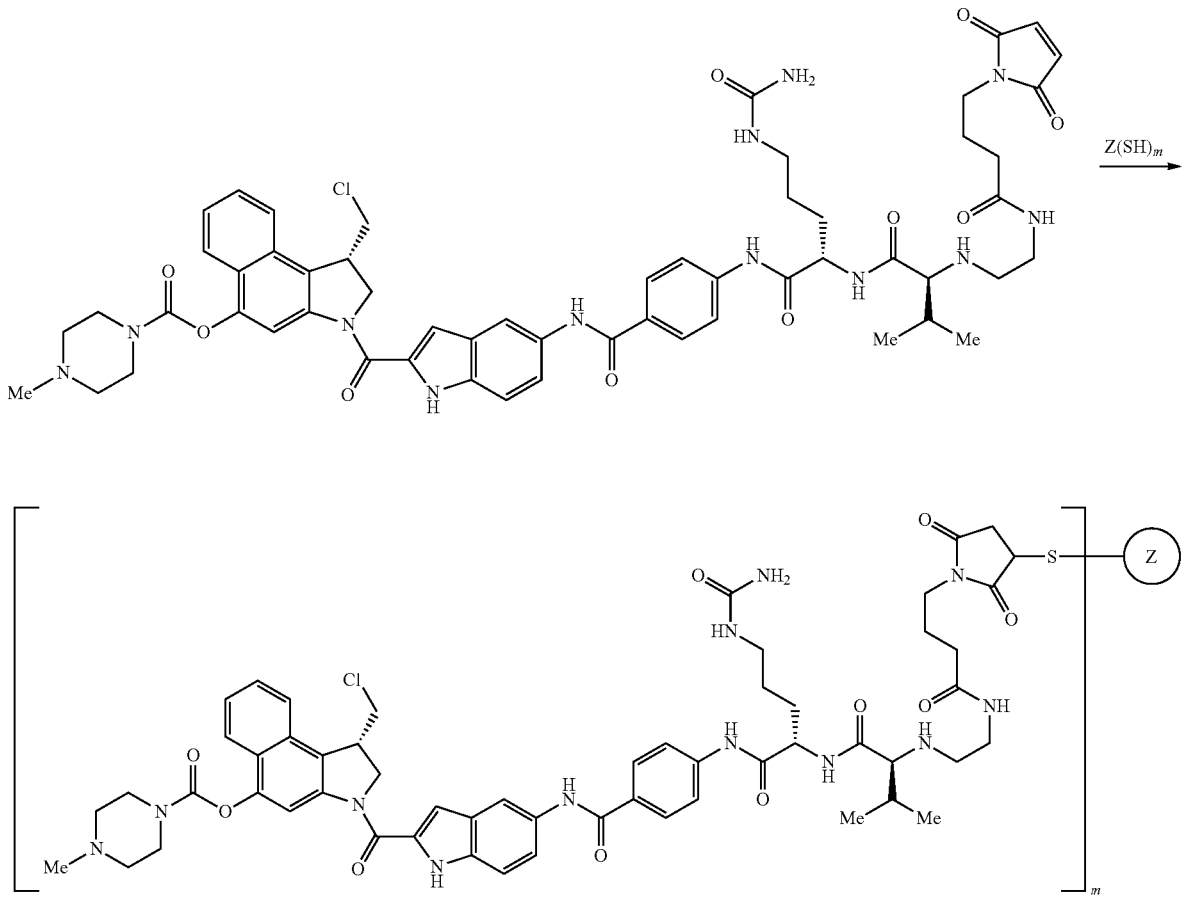

Formula M

The following is an illustrative procedure, based on introduction of free thiol groups into an antibody by reaction of its lysine ε-amino groups with 2-iminothiolane, followed by reaction with a drug-linker moiety D-$(X^Z)_a C(X^D)_b$—$R^{31}$, where $R^{31}$ is maleimide. Initially the antibody is buffer exchanged into 0.1 M phosphate buffer (pH 8.0) containing 50 mM NaCl and 2 mM DTPA and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at room temperature, the antibody is desalted into 50 mM pH 6.0 HEPES buffer using a Sephadex G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at room temperature. Blank samples of buffer alone plus DTDP are also incubated alongside. After 10 min, absorbance at 324 nm is measured and the number of thiol groups is quantitated using an extinction coefficient for thiopyridine of 19,800 M$^{-1}$.

Typically a thiolation level of three thiol groups per antibody is desired in this procedure. For example, with some antibodies this can be achieved by adding a 15-fold molar excess of 2-iminothiolane followed by incubation at room temperature for 1 h. The antibody is then incubated with 2-iminothiolane at the desired molar ratio and then desalted into conjugation buffer (50 mM pH 6.0 HEPES buffer containing 5 mM glycine and 2 mM DTPA). The thiolated material is maintained on ice while the number of thiols introduced is quantitated as described above.

After verification of the number of thiols introduced, the drug-linker moiety D-$(X^Z)_a C(X^D)_b$—$R^{31}$ is added at a 3-fold molar excess per thiol. The conjugation reaction is allowed to proceed in conjugation buffer also containing a final concentration of 5% dimethylsulfoxide (DMSO), or similar alternative solvent. Commonly, the drug-linker stock solution is dissolved in 100% DMSO. The stock solution is added directly to the thiolated antibody, which has enough DMSO added to bring the final concentration to 10%, or pre-diluted in conjugation buffer containing a final concentration of 10% DMSO, followed by addition to an equal volume of thiolated antibody.

The conjugation reaction mixture is incubated at room temperature for 2 h with stirring. Following incubation, the conjugation reaction mixture is centrifuged and filtered through a 0.2 μm filter. Purification of the conjugate can be achieved through chromatography using a number of methods. In one method, the conjugate is purified using size-exclusion chromatography on a Sephacryl S200 column pre-equilibrated with 50 mM pH 7.2 HEPES buffer containing 5 mM glycine and 50 mM NaCl. Chromatography is carried out at a linear flow rate of 28 cm/h. Fractions containing conjugate are collected, pooled and concentrated. In an alternative method, purification can be achieved through ion-exchange chromatography. Conditions vary from antibody to antibody and should be optimized in each case. For example, antibody-drug conjugate reaction mix is applied to an SP-Sepharose column pre-equilibrated in 50 mM pH 5.5 HEPES containing 5 mM glycine. The antibody conjugate is eluted using a gradient of 0-1 M NaCl in equilibration buffer at pH 5.5. Relevant fractions containing the conjugate are pooled and dialyzed against formulation buffer (50 mM pH 7.2 HEPES buffer containing 5 mM glycine and 100 mM NaCl).

Those skilled in the art will understand that the above-described conditions and methodology are exemplary and non-limiting and that other approaches for conjugating antibodies are known in the art and usable in the present invention.

ADEPT

In another embodiment, an antibody according to this invention is conjugated to an enzyme for use in antibody-directed enzyme prodrug therapy (ADEPT). In ADEPT, an enzyme is guided to a tumor site by the antibody to which it is conjugated. There, the enzyme acts on a subsequently administered prodrug to release locally the corresponding active drug. See, e.g., Melton et al., *J. Natl Cancer Inst.* 88(3/4), 153-165 (1996). Exemplary enzymes that can be conjugated for use in ADEPT include carboxypeptidase A and G2, alkaline phosphatase, β-glucuronidase, β-lactamase, β-glucosidase, penicillin amidase, aminopeptidase, cytosine deaminase, and nitroreductase.

Because ADEPT does not require the release of the enzyme from the antibody, the presence of a cleavable group between the antibody and the enzyme is not mandatory. Thus, an ADEPT conjugate can be represented by formula (f)

Z—X-D                                              (f)

where Z is an antibody of this invention; D is an enzyme, and X is a linker connecting Z and D.

Immunoconjugates

Immunoconjugates that include one or more cytotoxins are referred to as "immunotoxins".

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

Bispecific Molecules

In another aspect, the present invention features bispecific molecules comprising an anti-CADM1 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for CADM1 and a second binding specificity for a second target epitope. In a particular embodiment of the invention, the second target epitope is an Fc receptor, e.g., human FcγRI (CD64) or a human Fcα receptor (CD89). Therefore, the invention includes bispecific molecules capable of binding both to FcγR or FcαR expressing effector cells (e.g., monocytes, macrophages or polymorphonuclear cells (PMNs)), and to target cells expressing CADM1. These bispecific molecules target CADM1 expressing cells to effector cell and trigger Fc receptor-mediated effector cell activities, such as phagocytosis of CADM1 expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-CADM1 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII (CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ M$^{-1}$) for both IgA1 and IgA2, which is increased upon exposure to cytokines such as G-CSF or GM-CSF (Morton, H. C. et al. (1996) Critical Reviews in Immunology 16:423-440). Four FcαRI-specific monoclonal antibodies, identified as A3, A59, A62 and A77, which bind FcαRI outside the IgA ligand binding domain, have been described (Monteiro, R. C. et al. (1992) J. Immunol. 148: 1764).

FcαRI and FcγRI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-CADM1 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) J. Exp. Med. 160: 1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83, and Glennie et al. (1987) J. Immunol. 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoas says, Seventh Training Course on Radioligand Assay Techniques, The Endocrine Society, March, 1986, which is incorporated by reference herein). The radioactive isotope can be detected by such means as the use of a $\gamma$ counter or a scintillation counter or by autoradiography.

Antibody Fragments and Antibody Mimetics

The instant invention is not limited to traditional antibodies and may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Affibodies, DARPins, Anticalins, Avimers, and Versabodies that employ binding structures that, while they mimic traditional antibody binding, are generated from and function via distinct mechanisms.

Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology; however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labeled Affibodies may also be useful in imaging applications for determining abundance of Isoforms.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028, and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved B-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., Nature Biotechnology, 25(8) 921-929 (2007), which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-CADM1 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CADM1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CADM1 antibody of the invention preferably results in a decrease in severity of disease symptoms, an increase in frequency and duration of disease symptom-free periods, or a prevention of impairment or disability due to the disease affliction. For example, for the treatment of CADM1$^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods

The antibodies, particularly the human antibodies, antibody compositions and methods of the present invention have numerous in vitro and in vivo diagnostic and therapeutic utilities involving the diagnosis and treatment of CADM1 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by CADM1 activity. The methods are particularly suitable for treating human patients having a disorder associated with aberrant CADM1 expression. When antibodies to CADM1 are administered together with another agent, the two can be administered in either order or simultaneously.

Given the specific binding of the antibodies of the invention for CADM1, the antibodies of the invention can be used to specifically detect CADM1 expression on the surface of cells and, moreover, can be used to purify CADM1 via immunoaffinity purification.

Furthermore, given the expression of CADM1 on various tumor cells, the human antibodies, antibody compositions and methods of the present invention can be used to treat a subject with a tumorigenic disorder, e.g., a disorder characterized by the presence of tumor cells expressing CADM1 including, for example, small cell lung cancer, adult T-cell leukemia, neuroendocrine cancers including those of lung, adrenal, pituitary, GI-tract, kidney, liver (including hepatocellular carcinomas), pancreas (including insulinomas and glucagonomas), glioblastomas, and carcinoid tumors including those of pancreas, lung, GI tract, liver, or kidney.

In one embodiment, the antibodies (e.g., human monoclonal antibodies, multispecific and bispecific molecules and compositions) of the invention can be used to detect levels of CADM1, or levels of cells which contain CADM1 on their membrane surface, which levels can then be linked to certain disease symptoms. Alternatively, the antibodies can be used to inhibit or block CADM1 function which, in turn, can be linked to the prevention or amelioration of certain disease symptoms, thereby implicating CADM1 as a mediator of the disease. This can be achieved by contacting a sample and a control sample with the anti-CADM1 antibody under conditions that allow for the formation of a complex between the antibody and CADM1. Any complexes formed between the antibody and CADM1 are detected and compared in the sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using the flow cytometric assays described in the Examples below.

The antibodies (e.g., human antibodies, multispecific and bispecific molecules, immunoconjugates and compositions) of the invention have additional utility in therapy and diagnosis of CADM1 related diseases. For example, the human monoclonal antibodies, the multispecific or bispecific molecules and the immunoconjugates can be used to elicit in vivo or in vitro one or more of the following biological activities: to inhibit the growth of and/or kill a cell expressing CADM1; to mediate phagocytosis or ADCC of a cell expressing CADM1 in the presence of human effector cells, or to block CADM1 ligand binding to CADM1.

In a particular embodiment, the antibodies (e.g., human antibodies, multispecific and bispecific molecules and compositions) are used in vivo to treat, prevent or diagnose a variety of CADM1-related diseases. Examples of CADM1-related diseases include, among others, human cancer tissues representing small cell lung cancer, neuroendocrine pancreatic cancer, liver cancer, lung carcinoids, and gastro-intestinal carcinoids.

Suitable routes of administering the antibody compositions (e.g., human monoclonal antibodies, multispecific and bispecific molecules and immunoconjugates) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CADM1 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Co-administration of the human anti-CADM1 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CADM1, and to affect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CADM1 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g., human, humanized, or chimeric antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human, humanized, or chimeric antibodies, multispecific and bispecific molecules and immunoconjugates) of the invention can also be administered together with complement. In certain embodiments, the instant disclosure provides compositions comprising human antibodies, multispecific or bispecific molecules and serum or complement. These compositions can be advantageous when the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the antibody compositions of the invention (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the CADM1 antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of the invention can also be used to target cells expressing FcγR or CADM1, for example for labeling such cells. For such use, the binding agent can be linked to a molecule that can be detected. Thus, the invention provides methods for localizing ex vivo or in vitro cells expressing Fc receptors, such as FcγR, or CADM1. The detectable label can be, e.g., a radioisotope, a fluorescent compound, an enzyme, or an enzyme co-factor.

In a particular embodiment, the invention provides methods for detecting the presence of CADM1 antigen in a sample, or measuring the amount of CADM1 antigen, comprising contacting the sample, and a control sample, with a human monoclonal antibody, or an antigen binding portion thereof, which specifically binds to CADM1, under conditions that allow for formation of a complex between the antibody or portion thereof and CADM1. The formation of a complex is then detected, wherein a difference complex formation between the sample compared to the control sample is indicative the presence of CADM1 antigen in the sample.

In other embodiments, the invention provides methods for treating a CADM1 mediated disorder in a subject, e.g., human cancers, including small cell lung cancer, neuroendocrine cancers including those of lung, adrenal, pituitary, GI-tract, kidney, liver, pancreas (including insulinomas and glucagonomas), and carcinoid tumors including those of pancreas, lung, GI tract, liver or kidney.

In yet another embodiment, immunoconjugates of the invention can be used to target compounds (e.g., therapeutic agents, labels, cytotoxins, radiotoxins immunosuppressants, etc.) to cells which have CADM1 cell surface receptors by linking such compounds to the antibody. For example, an anti-CADM1 antibody can be conjugated to any of the toxin compounds described in U.S. Pat. Nos. 6,281,354 and 6,548,530, US patent publication Nos. 20030050331, 20030064984, 20030073852, and 20040087497, or published in WO 03/022806. Thus, the invention also provides methods for localizing ex vivo or in vivo cells expressing CADM1 (e.g., with a detectable label, such as a radioisotope, a fluorescent compound, an enzyme, or an enzyme co-factor). Alternatively, the immunoconjugates can be used to kill cells which have CADM1 cell surface receptors by targeting cytotoxins or radiotoxins to CADM1.

The present invention is further illustrated by the following examples which should not be construed as further limiting. The contents of all figures and all references, patents and published patent applications cited throughout this application are expressly incorporated herein by reference.

EXAMPLES

Example 1

Generation of Human Monoclonal Antibodies Against CADM1 Antigen

A recombinant fusion protein composed of the extracellular domain of the CADM1 (CADM1 ECD) linked to a non-CADM1 polypeptide (his protein) (SEQ ID NO:44) was generated by standard recombinant methods and used as antigen for immunization (see below).

Transgenic HuMAb Mouse® and KM Mouse® Strains

Fully human monoclonal antibodies to CADM1 were prepared using HCo7 and HCo27 strains of the transgenic HuMAb Mouse® and the KM strain of transgenic transchromosomic mice, each of which express human antibody genes. In each of these mouse strains, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Each of these mouse strains carries a human kappa light chain transgene, KCo5, as described in Fishwild et al. (1996) *Nature Biotechnology* 14:845-851. The HCo7 strain carries the HCo7 human heavy chain transgene as described in U.S. Pat. Nos. 5,545,806; 5,625,825; and 5,545,807. The HCo27 strain carries the HCo27 human heavy chain transgene as described in PCT Publication WO 01/09187. The KM Mouse® strain contains the SC20 transchromosome as described in PCT Publication WO 02/43478.

HuMab and KM Immunizations

To generate fully human monoclonal antibodies to CADM1, HuMab mice of the HCo7, HCo27 and KM Mouse strains were immunized with purified recombinant CADM1-ECD-his protein. General immunization schemes for these mice are described in Lonberg, N. et al (1994) *Nature* 368 (6474): 856-859; Fishwild, D. et al. (1996) *Nature Biotechnology* 14: 845-851 and PCT Publication WO 98/24884. The mice were 6-16 weeks of age upon the first infusion of antigen. A purified recombinant preparation (5-50 µg) of CADM1-ECD-his protein was used to immunize the HuMab and KM Mouse®.

Transgenic mice were immunized with the antigen in Ribi adjuvant either intraperitonealy (IP), subcutaneously (Sc) or via footpad (FP) in 3-21 days intervals (up to a total of 9 immunizations). The immune response was monitored by retroorbital bleeds. The plasma was screened by ELISA (as described below), and mice with sufficient titers of anti-CADM1 human immunogolobulin were used for fusions.

Mice were boosted intravenously with antigen 3 and 2 days before sacrifice and removal of the spleen. Typically, 10-20 fusions for each antigen were performed. Several dozen mice were immunized for each antigen.

Selection of a HuMab Mouse® or KM Mouse® Animal Producing Anti-CADM1 Antibodies

To select a HuMab Mouse® or KM Mouse® animal producing antibodies that bound CADM1, sera from immunized mice was tested by ELISA as described by Fishwild, D. et al. (1996)(supra). Briefly, microtiter plates were coated with purified recombinant CADM1 at 1-2 µg/ml in PBS, 50 µl/wells incubated 4° C. overnight then blocked with 200 µl/well of 5% chicken serum in PBS/Tween (0.05%). Dilutions of plasma from CADM1-immunized mice were added to each well and incubated for 1-2 hours at ambient temperature. The plates were washed with PBS/Tween and then incubated with a goat-anti-human IgG Fc polyclonal antibody conjugated with horseradish peroxidase (HRP) for 1 hour at room temperature. After washing, the plates were developed with ABTS substrate (Moss Inc, product: ABTS-1000) and analyzed by spectrophotometer at OD 415-495. Mice that developed the highest titers of anti-CADM1 antibodies were used for fusions. Fusions were performed as described below and hybridoma supernatants were tested for anti-CADM1 activity by ELISA and FACS.

Generation of Hybridomas Producing Human Monoclonal Antibodies to CADM1

The mouse splenocytes, isolated from a HuMab Mouse® and/or a KM Mouse®, were fused with a mouse myeloma cell line using electric field based electrofusion using a Cyto Pulse large chamber cull fusion electroporator (Cyto Pulse Sciences, Inc., Glen Burnie, Md.). Briefly, single cell suspensions of splenic lymphocytes from immunized mice were fused to equal number of Sp2/0 nonsecreting mouse myeloma cells (ATCC, CRL 1581). Cells were plated at a density of approximately $2\times10^4$/well in flat bottom microtiter plates, which were then incubated in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Approximately 10-14 days after cell plating, supernatants from individual wells were screened first for whether they contained human g,k antibodies. The supernatants which were scored positive for human g,k were then subsequently screened-by ELISA and FACS (described above) for human anti-CADM1 monoclonal IgG antibodies. The antibody secreting hybridomas were transferred to 24 well plates, screened again and, if still positive for human anti-CADM1 IgG monoclonal antibodies, were subcloned at least twice by limiting dilution. The stable subclones were then cultured in vitro to generate small amounts of antibody in tissue culture medium for further characterization.

Hybridoma clones PTA021_A1, PTA021_A2, and PTA021_A3 generated from a KM Mouse®, were selected for further analysis

Example 2

Structural Characterization of Human Monoclonal Antibodies PTA021_A1, PTA021_A2, or PTA021_A3

The cDNA sequences encoding the heavy and light chain variable regions of the PTA021_A1, PTA021_A2, and PTA021_A3 monoclonal antibodies were obtained from the PTA021_A1, PTA021_A2, and PTA021_A3 hybridomas, respectively, using standard PCR techniques and were sequenced using standard DNA sequencing techniques.

The antibody sequences may be mutagenized to revert back to germline residues at one or more residues. For example, the PTA021_A1 heavy chain variable region can be mutagenized to reflect the germline sequence at specific sites (e.g., residue 30) to remove glycosylation sites (e.g., a N30Q mutation).

The nucleotide and amino acid sequences of the heavy chain variable region of PTA021_A1 are shown in FIG. 1A and in SEQ ID NO:19 and 25, respectively.

The nucleotide and amino acid sequences of the light chain variable region of PTA021_A1 are shown in FIG. 1B and in SEQ ID NO:28 and 22, respectively.

Comparison of the PTA021_A1 heavy chain immunoglobulin sequence to the known human germline immunoglobulin heavy chain sequences demonstrated that the PTA021_A1 heavy chain utilizes a $V_H$ segment from human germline $V_H$ 2-05, a D segment from the human germline 6-6, and a JH segment from human germline JH 5b. The alignment of the PTA021_A1 $V_H$ sequence to the germline $V_H$ 2-05 sequence is shown in FIG. 4. Further analysis of the PTA021_A1 $V_H$ sequence using the Kabat system of CDR region determination led to the delineation of the heavy chain CDR1, CDR2 and CD3 regions as shown in FIGS. 1A and 4, and in SEQ ID NOs:1, 4 and 7, respectively.

Comparison of the PTA021_A1 light chain immunoglobulin sequence to the known human germline immunoglobulin light chain sequences demonstrated that the PTA021_A1 light chain utilizes a $V_K$ segment from human germline $V_K$ L15 and a JK segment from human germline JK 4. The alignment of the PTA021_A1 $V_K$ sequence to the germline $V_K$ L15 sequence is shown in FIG. 7. Further analysis of the PTA021_A1 $V_K$ sequence using the Kabat system of CDR region determination led to the delineation of the light chain CDR1, CDR2 and CD3 regions as shown in FIGS. 1B and 7, and in SEQ ID NOs:10, 13 and 16, respectively.

The nucleotide and amino acid sequences of the heavy chain variable region of PTA021_A2 are shown in FIG. 2A and in SEQ ID NO:26 and 20, respectively.

The nucleotide and amino acid sequences of the light chain variable region of PTA021_A2 are shown in FIG. 2B and in SEQ ID NO:29 and 23, respectively.

Comparison of the PTA021_A2 heavy chain immunoglobulin sequence to the known human germline immunoglobulin heavy chain sequences demonstrated that the PTA021_A2 heavy chain utilizes a $V_H$ segment from human germline $V_H$ 2-05, a D segment from the human germline 6-6, and a JH segment from human germline JH 5b. The alignment of the PTA021_A2 $V_H$ sequence to the germline $V_H$ 2-05 sequence is shown in FIG. 5. Further analysis of the PTA021_A2 $V_H$ sequence using the Kabat system of CDR region determination led to the delineation of the heavy chain CDR1, CDR2 and CD3 regions as shown in FIGS. 2A and 5, and in SEQ ID NOs:2, 5 and 8, respectively.

Comparison of the PTA021_A2 light chain immunoglobulin sequence to the known human germline immunoglobulin light chain sequences demonstrated that the PTA021_A2 light chain utilizes a $V_K$ segment from human germline $V_K$ L15 and a JK segment from human germline JK 4. The alignment of the PTA021_A2 $V_L$ sequence to the germline $V_K$ L15 sequence is shown in FIG. 8. Further analysis of the PTA021_A2 $V_K$ sequence using the Kabat system of CDR region determination led to the delineation of the light chain CDR1, CDR2 and CD3 regions as shown in FIGS. 2B and 8, and in SEQ ID NOs: 11, 14 and 17, respectively.

The nucleotide and amino acid sequences of the heavy chain variable region of PTA021_A3 are shown in FIG. 3A and in SEQ ID NO:27 and 21, respectively.

The nucleotide and amino acid sequences of the light chain variable region of PTA021_A3 are shown in FIG. 3B and in SEQ ID NO:30 and 24, respectively.

Comparison of the PTA021_A3 heavy chain immunoglobulin sequence to the known human germline immunoglobulin heavy chain sequences demonstrated that the PTA021_A3 heavy chain utilizes a $V_H$ segment from human germline $V_H$ 2-05, a D segment from the human germline 6-6, and a JH segment from human germline JH JH5b. The alignment of the PTA021_A3 $V_H$ sequence to the germline $V_H$ 2-05 sequence is shown in FIG. 6. Further analysis of the PTA021_A3 $V_H$ sequence using the Kabat system of CDR region determination led to the delineation of the heavy chain CDR1, CDR2 and CD3 regions as shown in FIGS. 3A and 6, and in SEQ ID NOs: 3, 6 and 9, respectively.

Comparison of the PTA021_A3 light chain immunoglobulin sequence to the known human germline immunoglobulin light chain sequences demonstrated that the PTA021_A3 light chain utilizes a $V_K$ segment from human germline $V_K$ L15 and a JK segment from human germline JK 4. The alignment of the PTA021_A3 $V_L$ sequence to the germline $V_K$ L15 sequence is shown in FIG. 9. Further analysis of the PTA021_A3 $V_L$ sequence using the Kabat system of CDR region determination led to the delineation of the light chain CDR1, CDR2 and CD3 regions as shown in FIGS. 3B and 9, and in SEQ ID NOs:12, 15, and 18, respectively.

Example 3

Characterization of Binding Properties of CADM1 Monoclonal Antibodies Flow Cytometry Studies In this example, the binding of mAbs PTA021_A1, PTA021_A2, PTA021_A3 and the non-fucosylated version of PTA021_A3 (NF) to cell surface CADM1 was examined by flow cytometry.

To test the ability of the antibodies to bind to cell surface CADM1 protein, the antibodies were incubated with different CADM1-expressing cells: NCI-H69 (ATCC Designation HTB-119™), a human small cell lung cancer cell line; DMS79 (ATCC Designation CRL-2049™), a human small cell lung cancer line; SKOV3 (ATCC Designation HTB-77™), a human ovarian cancer cell line; A549 (ATCC Designation CCL-185™), a human non-small cell lung cancer cell line; SkMel28 (ATCC Designation HTB-72™), a human melanoma cell line and 786-O (ATCC Designation CRL-1932™), a human renal cell carcinoma cell line. For the flow cytometry studies, the PTA021_A1, PTA021_A2, PTA021_A3 and PTA021_A3 (NF) monoclonal antibodies were diluted with cold 1×PBS+0.1% BSA to 40 µg/ml. For the binding reaction, 50 µl of diluted antibody solution was added to a 50 µl cell suspension containing 4×10$^5$ cells and the mixture was incubated on ice for 30-60 minutes. The cells were then washed three times with 1×PBS+0.1% BSA. A 1:50 dilution of R-phycoerythrin-labeled goat anti-human IgG Fγ F(ab)$_2$ fragment (Jackson ImmunoResearch Labs, Cat. #109-116-098) was added and the mixture was incubated on ice for 1 hour, followed by washing twice with cold 1×PBS+0.1% BSA. After the final wash, 200 µl of cold 1×PBS+0.1% BSA was added to each solution and analysis of antibody binding was carried out by FACS.

FIG. 10 and Table 1 below show the results of the flow cytometry analysis and the $EC_{50}$ for binding to the NCI-H69 cell line. The results demonstrate that all three monoclonal antibodies bind effectively to cell-surface human CADM1.

TABLE 1

| Binding of Anti-CADM1 Antibodies to Cells Expressing Human CADM1 | |
|---|---|
| Antibody | NCI-H69 Cells $EC_{50}$ (nM) |
| PTA021_A1 | 0.588 |
| PTA021_A2 | 0.667 |
| PTA021_A3 | 0.6742 |

FIGS. 11A and 11B show the results of the flow cytometry analysis in NCI-H69 and DMS79 small cell lung cancer cell lines.

FIG. 12 shows the results of flow cytometric analysis on antibody PTA021_A3 in the SKOV3 ovarian cancer cell line.

Figure 13:
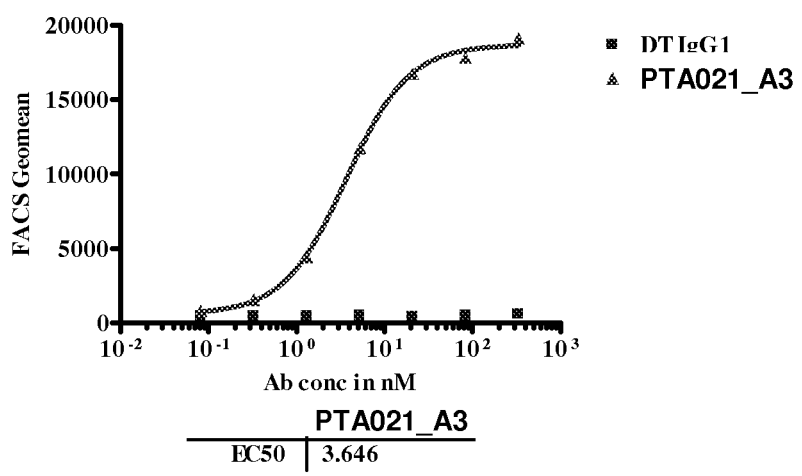
FIG. 13 shows the results of FACS analysis on PTA021_A3 in A549 non-small cell lung cancer cells.

FIG. 13 shows the results of flow cytometric analysis on antibody PTA021_A3 in the A549 non-small cell lung cancer cell line.

Figure 14:
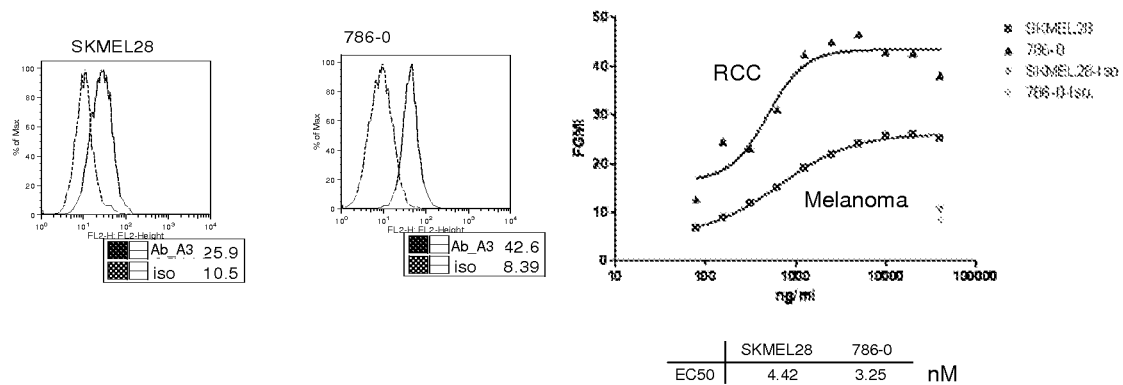
FIG. 14 shows the results of FACS analysis on PTA021_A3 in 786-O renal cell carcinoma cells and SkMel28 melanoma cells.

FIG. 14 shows the results of flow cytometric analysis on antibody PTA021_A3 in 786-O renal cell carcinoma and SkMel28 melanoma cell lines.

The results of FIGS. 11 to 14 demonstrate that PTA021_A3 binds effectively to cell surface human CADM1 in different CADM1-expressing cells.

Figure 15:
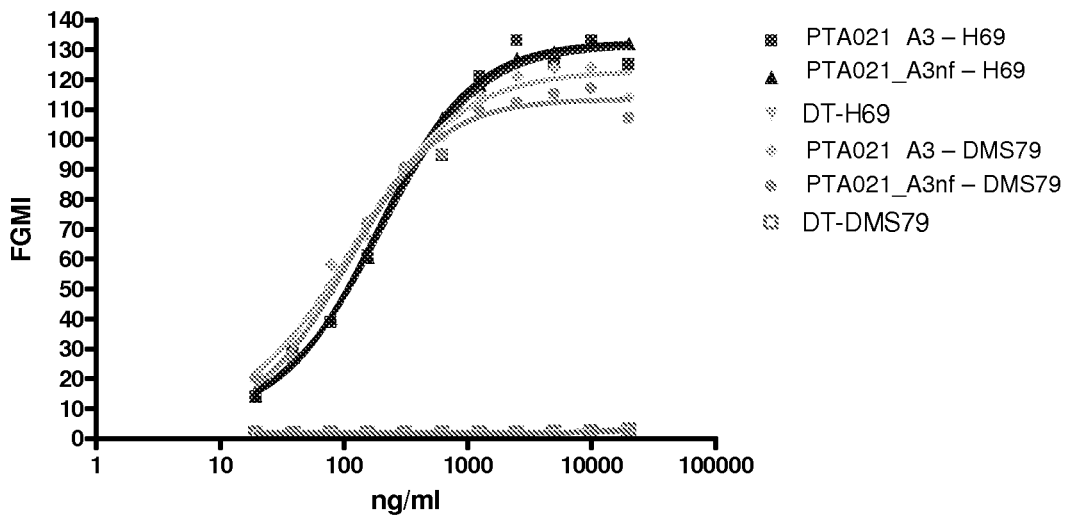
FIG. 15 shows the results of FACS analysis on PTA021_A3 and the non-fucosylated version of PTA021_A3 (nf) in NCI-H69 and DMS79 small cell lung cancer cells.

FIG. 15 shows the results of flow cytometric analysis on the non-fucosylated version of PTA021_A3 (NF) in NCI-H69 and DMS79 small cell lung cancer cell lines. These results demonstrate that non-fucosylation does not affect the binding of PTA021_A3 to cell surface human CADM1.

Example 4

Antibody-Dependent Cellular Cytotoxicity Mediated by Anti-CADM1 mAbs

To determine the ability of the anti-CADM1 mAbs to kill CADM1-expressing cells in the presence of effector cells via antibody dependent cellular cytotoxicity (ADCC), two cell lines, NCI-H69 and DMS79, were used as the target cells.

Human effector cells were prepared from whole blood as follows. Human peripheral blood mononuclear cells were purified from heparinized whole blood by standard Ficoll-paque separation. The cells were resuspended in RPMI1640 media containing 10% FBS (heat-inactivated) and 200 U/ml of human IL-2 and incubated overnight at 37° C. The following day, the cells were collected and washed four times in culture media and resuspended at 1×10$^7$ cells/ml. Target cells were prepared by incubating with BATDA reagent (Perkin Elmer, Wellesley, Mass.) at 2.5 µl BATDA per 1×10$^6$ target cells/mL for 20 minutes at 37° C. The target cells were washed four times, spun down and brought to a final volume of 1×10$^5$ cells/ml.

The target cells were tested for antibody specific ADCC to the human anti-CADM1 monoclonal antibodies using the Delfia fluorescence emission analysis as follows. NCI-H69 or DMS79 cells (100 µl of labeled target cells, 10$^4$ cells/well) were incubated with 50 µl of effector cells (10$^6$ cells/well) and 50 µl of antibody (10 ug/ml final concentration). A target to effector ratio of 1:25 was used throughout the experiments. In all studies, a human IgG1 isotype control was used as a negative control. Cells were spun down at 2000 rpm and incubated for one hour incubation at 37° C. The supernatants were then collected, submitted to centrifugation and 20 μl of supernatant was transferred to a flat bottom plate, to which 180 μl of Eu solution (Perkin Elmer, Wellesley, Mass.) was added and read in a RubyStar reader (BMG Labtech). The % lysis was calculated as follows: (sample release−spontaneous release*100)/(maximum release−spontaneous release), where the spontaneous release is the fluorescence from wells which contain target cells plus effector cells and maximum release is the fluorescence from wells containing target cells and have been treated with 2% Triton-X.

Figure 16A:
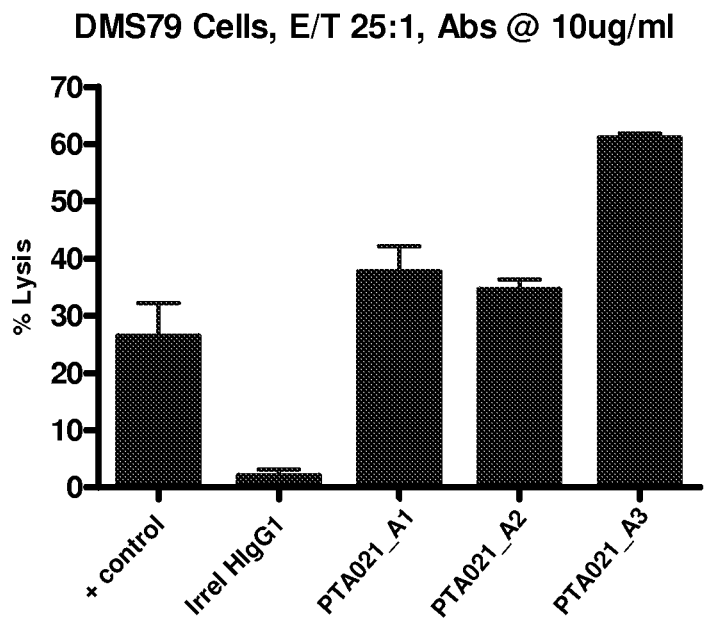
FIGS. 16A and 16B show antibody dependant cellular cytotoxicity (ADCC) mediated by PTA021_A1, PTA021_A2, and PTA021_A3 with the DMS79 and NCI-H69 cell lines, respectively.
Figure 16B:
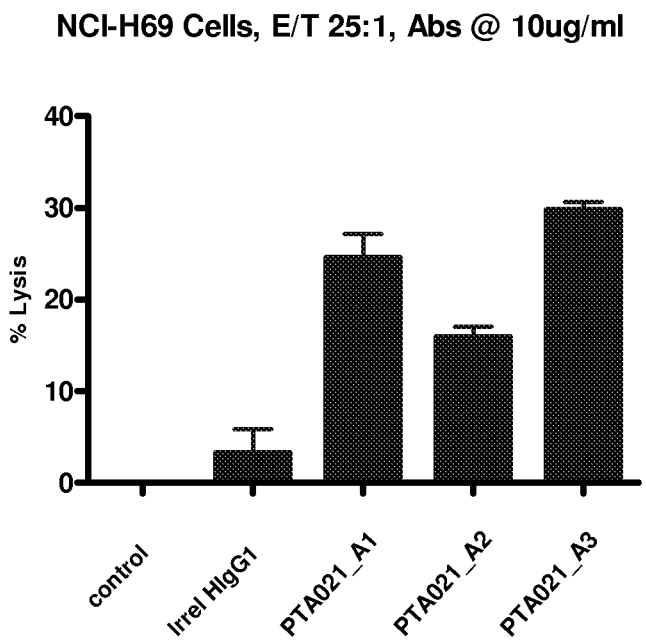

The results are summarized below in Table 2 and FIGS. 16A and 16B, which demonstrate that PTA021_A1, PTA021_A2, and PTA021_A3 are capable of specifically inducing ADCC on CADM1 expressing cancer cell lines

TABLE 2

Antibody Dependent Cellular Cytotoxicity Mediated by
PTA021_A1, PTA021_A2 and PTA021_A3 Antibodies

| Antibody | % Specific Lysis: NCI-H69 | % Specific Lysis: DMS79 |
|---|---|---|
| PTA021_A1 | 24.6 +/− 4.5 | 37.76 +/− 7.8 |
| PTA021_A2 | 15.9 +/− 1.9 | 34.66 +/− 3.1 |
| PTA021_A3 | 29.8 +/− 1.6 | 61.0 +/− 1.5 |
| Isotype Control | 3.3 +/− 4.6 | 2.96 +/− 1.9 |

Example 5

CADM1 Antibody Internalization

The monoclonal antibodies PTA021_A1, PTA021_A2, and PTA021_A3 were shown to be internalized by NCI-H69 and DMS79 cells upon binding to the cells using a Hum-Zap assay. The Hum-ZAP assay showed internalization of the anti-CADM1 monoclonal antibodies through binding of an anti-human IgG secondary antibody conjugated to the toxin saporin. (Advanced Targeting System, San Diego, Calif., IT-22-100). First, PTA021_A1, PTA021_A2, and PTA021_A3 were bound to the surface of the NCI-H69 or DMS79 cells. Then, the Hum-ZAP antibodies were bound to the primary antibodies. Next, the primary antibody/Hum-ZAP complex was internalized by the cells. The entrance of Saporin into the cells resulted in protein synthesis inhibition and eventual cell death.

Figure 17A:
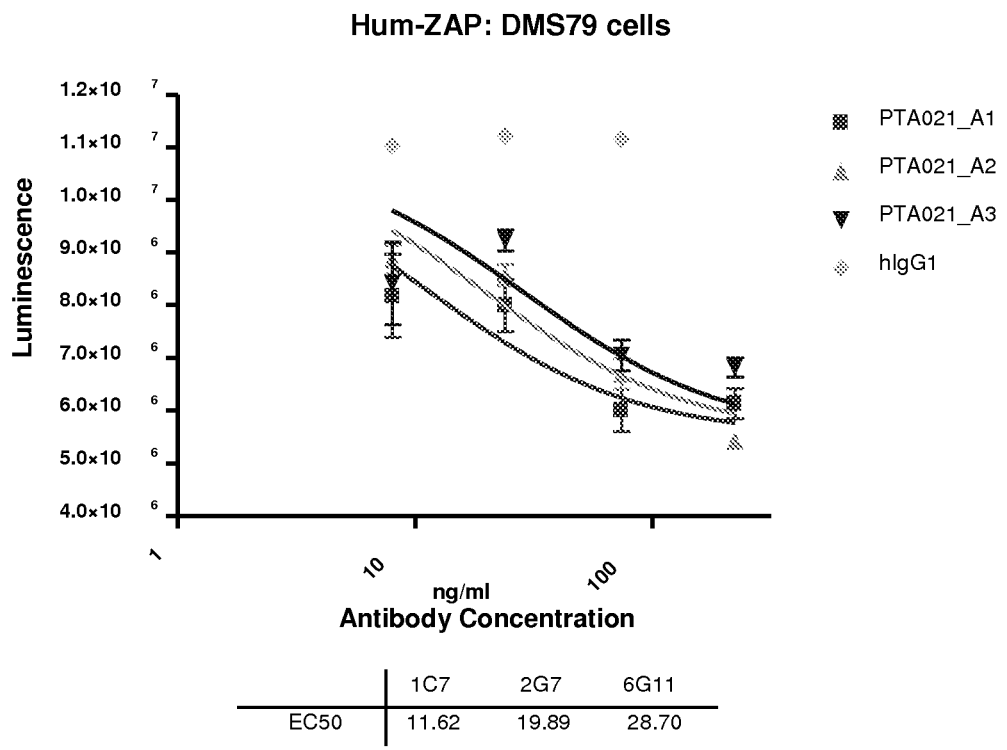
FIGS. 17A and 17B show the results of Hum-ZAP assays on PTA021_A1, PTA021_A2, and PTA021_A3 in DMS79 and NCI-H69 cells respectively.
Figure 17B:
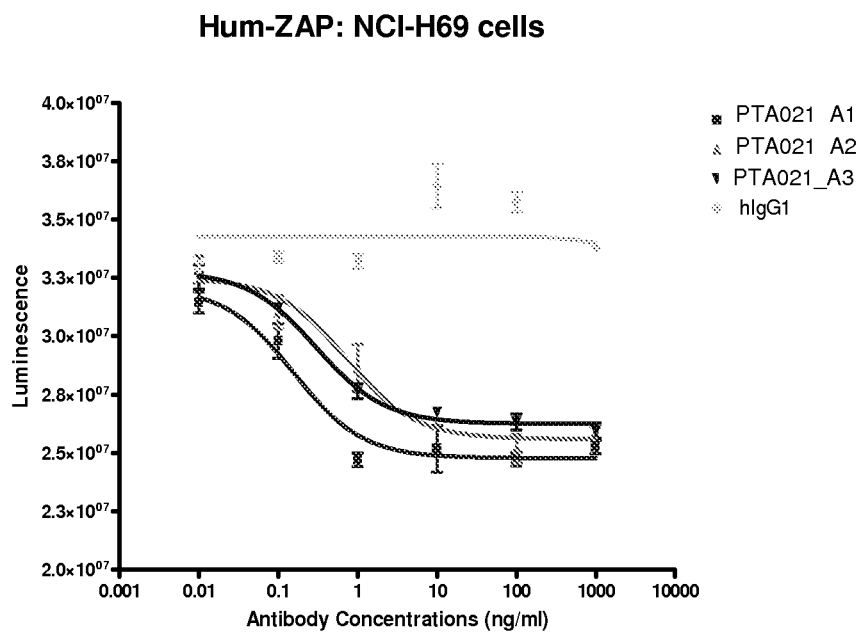

The Hum-ZAP assay was conducted as follows. Each of the cells was seeded at a density of $3 \times 10^3$ cells per well. The anti-CADM1 monoclonal antibodies or an isotype control human IgG were serially diluted then added to the cells. The Hum-ZAP was then added at a concentration of 2 μg/ml and the plates allowed to incubate for 96 hours. Cell viability in the plates was detected by CellTiter-Glo® Luminescent Cell Viability Assay kit (Promega, G7571) and the plates were read at 490 nM by a Luminomitor (Tuner BioSystems, Sunnyvale, Calif.). The data was analyzed by Prism (Graphpad). Cell death was proportional to the concentration of PTA021_A1, PTA021_A2, and PTA021_A3 monoclonal antibodies. FIGS. 17A and 17B show that the anti-CADM1 monoclonal antibodies were efficiently internalized by DMS79 and NCI-H69 cells respectively as compared to the hIgG1 isotype control antibody.

Example 6

CADM1 is Co-Localized with LAMP1

The monoclonal antibody PTA021_A3 was shown to co-localize with LAMP1 and thus to be internalized. PTA021_A3 was bound to NCI-H69 cells, washed and incubated at 37° C. for 45 minutes. The PTA021_A3 antibody was tracked via a FITC labeled anti-human antibody.

Some cells were permeabilized and stained with anti-human LAMP1, detected with TRITC labeled secondary.

The results showed that PTA021_A3 and LAMP1 are co-localized in the endosomes.

Example 7

Anti-CADM1 Antibodies Bind to Cancer Tissues

Anti-CADM1 monoclonal antibodies PTA021_A1, PTA021_A2, and PTA021_A3 were shown to bind human cancer tissues including tissues representing small cell lung cancer, neuroendocrine pancreatic cancer, liver cancer, lung carcinoids, and gastro-intestinal carcinoids. Biopsies from cancer patients were obtained and the antibodies used for immunohistochemistry staining (Cytomyx, Mass.). 5 μm tissues cores were used. After drying for 30 minutes on slides, the tissue sections were fixed with acetone at room temperature for 5 minutes. Slides were rinsed in PBS and then blocked with serum-free protein and peroxidase blocker (Dako S2001, CO) and subsequently incubated with primary antibody complex at 5 μg/ml for 45 minutes at room temperature. Next, the slides were washed and incubated for 30 minutes with FITC-conjugated secondary antibody (Jackson Immunoresearch Lab, 109-097-003) and washed again with PBS and incubated with polymer HRP conjugates (Dako, C0, K4063) for 20 minutes. Chromogen (Dako K3464) was used as a substrate, resulting in brown staining. Slides were mounted in Faramount Aqueous Mounting Media (Dako, S3025). PTA021_A1, PTA021_A2 and PTA021_A3 were shown to bind specifically to tumor cells of the types listed above. When stained with these monoclonal antibodies, other organs exhibit negative or non-specific staining, which include uterus, lung, liver, kidney, colon, cervix, breast, bone marrow, cerebellum, cerebrum, esophagus, heart, prostate, placenta, pituitary, ovary, mesothelia, tonsil, skin, small intestine, skeletal muscle, stomach, spleen, thymus, and thyroid. The data demonstrate that anti-CADM1 HuMabs PTA021_A1, PTA021_A2, and PTA021_A3 recognize CADM1 expressed on tumors, including those tumors of small cell lung cancer, non-small-cell lung cancer (including squamous carcinomas and adenocarcinomas), neuroendocrine cancers (including those of the pancreas, lung and gastro-intestinal tract), liver cancer, lung carcinoids, breast cancer, colon cancer, prostate cancer, ovarian cancer, kidney cancer, and gastro-intestinal carcinoids.

Immunohistochemistry on antibody PTA021_A3 in small cell lung cancer tissue samples showed 75% prevalence of high level (+++) membrane staining of all tumor cells. Immunohistochemistry on antibody PTA021_A3 in liver cancer tissue samples showed positive staining in 75%-95% of samples with 45% of tumors showing high level (+++) membrane staining of all tumor cells. Further studies on PTA021_A3 were carried out on smaller sample sets of non-small cell lung cancer, breast cancer, prostate cancer, colorectal cancer, ovarian cancer and renal cell carcinoma. Prevalence of positive staining in non-small cell lung carcinoma, breast carcinoma and renal clear cell carcinoma was ~66%; in prostate carcinoma and ovarian cancer prevalence was 100% and colorectal adenocarcinoma showed positive staining in 17% of samples. Neuroendocrine tumors of the lung, pancreas and gastro-intestinal tract were also tested with lung carcinoids and neuroendocrine pancreatic samples showing 75% prevalence and gastro-intestinal tract neuroendocrine tumors showing positive staining in 65% of samples.

Example 8

Effect of Fucosylated and Non-Fucosylated Anti-CADM1 Antibodies on Liver Cancer Tumor Growth in a Mouse Xenograft Model The effect of PTA021_A3 and the non-fucosylated version of PTA021_A3(NF) on the growth of liver cancer derived HepG2 cells in a mouse xenograft model was examined. In this xenograft model, SCID mice (CB17, from Charles River Laboratories, Hollister, Calif.) were implanted with $2.5 \times 10^6$ HepG2 cells/mouse and the HepG2 cells were allowed to grow for ca. 30 days. The mice were then randomized and treated intraperitoneally (i.p.) as follows in Table 3:

TABLE 3

Immunization Protocol for HEPG2 Tumor Xenograft Model

|  | Dose (Ab mg/kg) | Dose Day |
|---|---|---|
| Vehicle |  | Day 0 |
| Isotype IgG1 | 10 | Day 0, 4, 7, 11 |
| Isotype nf IgG1 | 10 | Day 0, 4, 7, 11 |
| CADM1 PTA021_A3 parental IgG1 | 10, 3 | Day 0, 4, 7, 11 |
| CADM1 PTA021_A3 nf IgG1 | 10, 3 | Day 0, 4, 7, 11 |
| Nexavar Sorafenib | 20 (Q1Dx3), 10 p.o. | Q1Dx8, Day 0-7 |

Nexavar Sorafenib, a chemical-based multiple kinase inhibitor used to treat renal cell carcinoma and liver cancer, was used as a control for targeted therapy.

Figure 18:
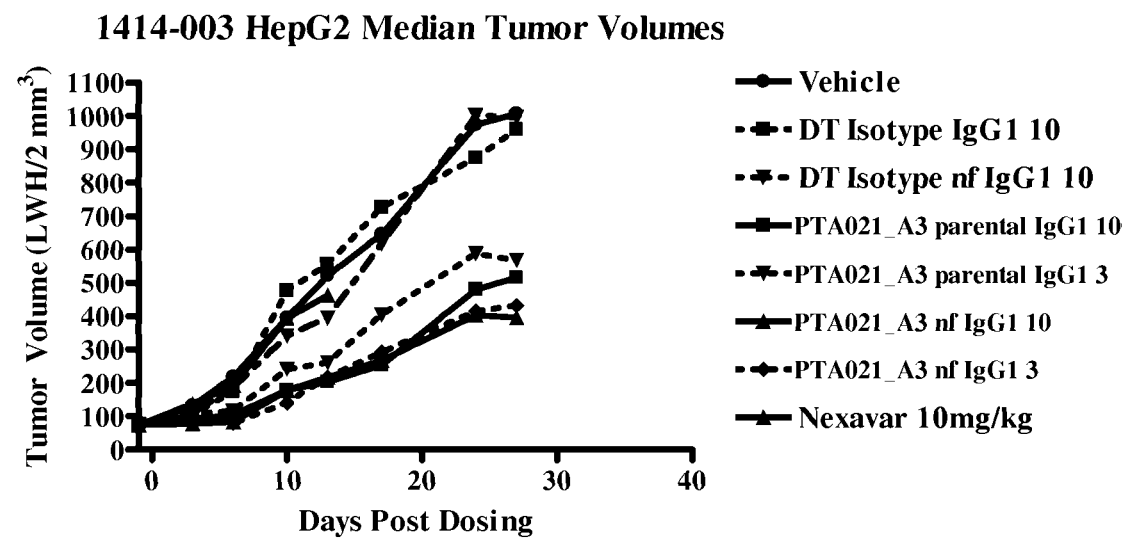
FIG. 18 presents a graph showing the effect of treatment using fucosylated or non-fucosylated PTA021_A3 antibodies on HepG2 tumor size in a mouse xenograft model.

As seen in FIG. 18, treatment with the PTA021_A3 and PTA021_A3 NF antibodies significantly reduced tumor growth rate, with the non-fucosylated PTA021_A3 NF antibody being the more potent.

Example 9

Anti-CADM1 Antibody-Drug Conjugate Inhibits HepG2 Cell Growth in a Mouse Xenograft Model The effect of a PTA021_A3 conjugate according to formula M (hereinafter referred to as "PTA021_A3-Formula A conjugate" or "PTA021_A3-Formula M") on the growth of hepatocellular carcinoma derived HepG2 cells in a mouse xenograft model was examined. In this xenograft model, SCID mice (CB17, from Charles River Laboratories, Hollister, Calif.) were implanted with $2.5 \times 10^6$ HepG2 cells/mouse and the HepG2 cells were allowed to grow for ca. 30 days. The mice were then randomized and treated intraperitoneally (i.p.) with PTA021_A3-Formula M conjugate (0.1 umole/kg, or 0.03 umol/kg). DT, and anti diptheria toxin antibody, was used as a non binding isotype control. Nexavar Sorafenib, a chemical-based multiple kinase inhibitor used to treat renal cell carcinoma and liver cancer, was used as a control for targeted therapy.

Figure 19:
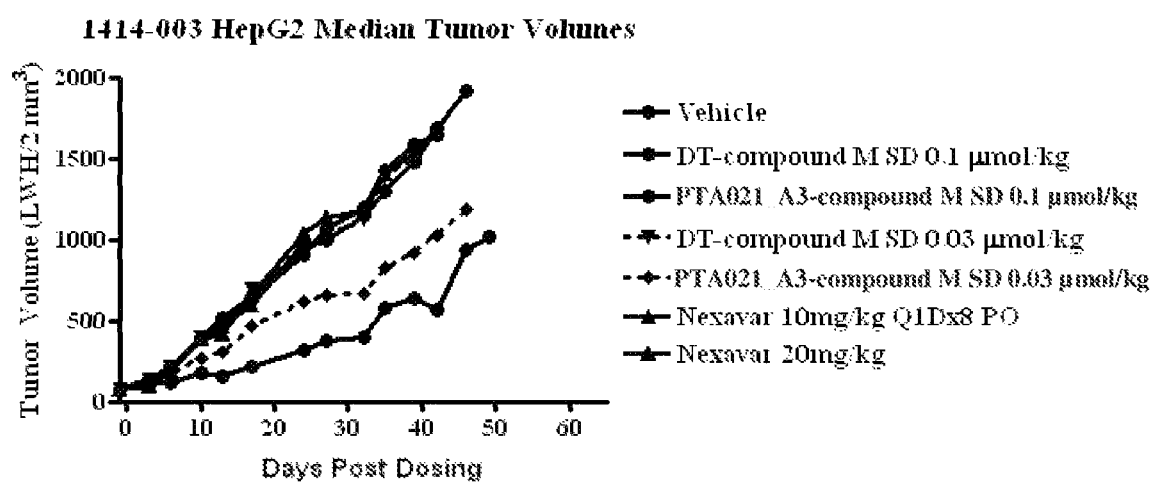
FIG. 19 presents a graph showing the effect of treatment with a PTA021_A3-Formula M conjugate on HepG2 tumor size in a mouse xenograft model.

As seen in FIG. 19, treatment with the PTA021_A3-Formula M conjugate significantly inhibited tumor growth rate in a dose dependent fashion.

Example 10

Anti-CADM1 Antibody-Drug Conjugate Inhibits DMS79 Cell Growth in a Mouse Xenograft Model The effect of PTA021_A3-Formula M on the growth of small cell lung cancer derived DMS79 cells in a mouse xenograft model was examined. In this xenograft model, SCID mice (CB17, from Charles River Laboratories, Hollister, Calif.) were implanted with $5 \times 10^6$ DMS79 cells/mouse and the DMS79 cells were allowed to grow until the mean tumor volume was ca. 200 mm$^3$. The mice were then randomized and treated intraperitoneally (i.p.) with PTA021_A3-Formula M conjugate in two studies.

Figure 20A:
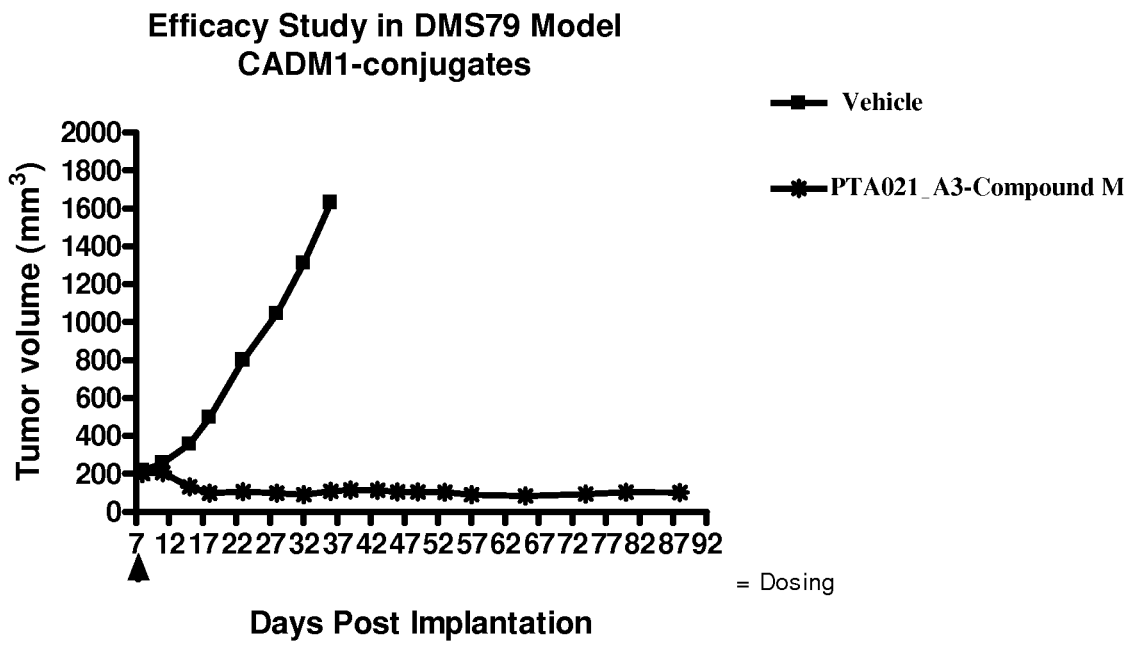
FIG. 20A presents a graph showing the effect of treatment with dosages of 0.3 umol/kg of a PTA021_A3-Formula M conjugate on DMS79 tumor size in a mouse xenograft model.
Figure 20B:
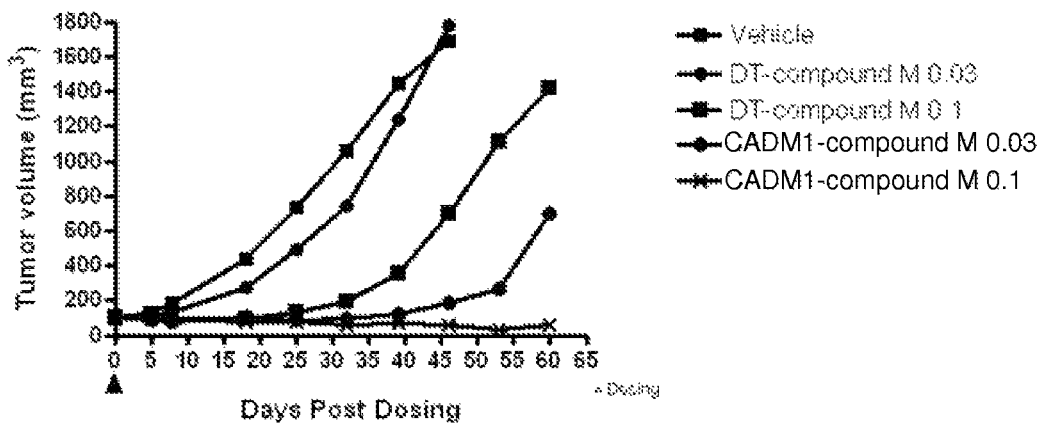
FIG. 20B presents a graph showing the effect of treatment with dosages of 0.1 and 0.03 umol/kg of a PTA021_A3-Formula M conjugate on DMS79 tumor size in a mouse xenograft model. The study completed on day 60.

As seen in FIG. 20A, treatment with the PTA021_A3-Formula M conjugate at 0.3 μmole/kg caused complete tumor regression in all mice throughout the study (day 88). As seen in FIG. 20B, treatment with the PTA021_A3-Formula M conjugate caused tumor regression at the 0.1 umol/kg dose through the study which completed on day 60. The low dose of 0.03 umol/kg caused significant delay in tumor growth.

Example 11

Antibody-Dependent Cellular Cytotoxicity Mediated by PTA021_A3 and Non-Fucosylated PTA021_A3

A fluorescence cytotoxicity assay was used to determine the ability of the non fucosylated PTA021_A3 anti-CADM1 mAb to kill CADM1-expressing cells in the presence of effector cells via antibody dependent cellular cytotoxicity (ADCC with HepG2, 786-O and DMS79 cells).

Human effector cells were prepared from whole blood as follows. Human peripheral blood mononuclear cells were purified from heparinized whole blood by standard Ficoll-paque separation. The cells were resuspended in RPMI1640 media containing 10% FBS (heat-inactivated) and 200 U/ml of human IL-2 and incubated overnight at 37° C. The following day, the cells were collected and washed four times in culture media and resuspended at $2 \times 10^7$ cells/ml. Target CHO-mesothelin cells were prepared by incubating with BATDA reagent (Perkin Elmer, Wellesley, Mass.) at 2.5 BATDA per $1 \times 10^6$ target cells/mL for 20 minutes at 37° C. The target cells were washed four times, spun down and brought to a final volume of $1 \times 10^5$ cells/ml.

The HepG2, 786-O and DMS79 cells were tested for antibody specific ADCC to the human anti-CADM1 PTA021_A3 monoclonal antibody and the non-fucosylated preparation of PTA021_A3 using the Delfia fluorescence emission analysis as follows. HepG2, 786-O or DMS79 (100 μl of labeled target cells, $10^4$ cells/well) were incubated with 50 μl of effector cells ($10^6$ cells/well) and 50 μl of antibody (10 ug/ml final concentration). A target to effector ratio of 1:100 was used throughout the experiments. In all studies, a human IgG1 isotype control was used as a negative control. Cells were spun down at 2000 rpm and incubated for one hour at 37° C. The supernatants were then collected, submitted to centrifugation and 20 μl of supernatant was transferred to a flat bottom plate, to which 180 μl of Eu solution (Perkin Elmer, Wellesley, Mass.) was added and read in a RubyStar reader (BMG Labtech). The % lysis was calculated as follows: (sample release−spontaneous release*100)/(maximum release−spontaneous release), where the spontaneous release is the fluorescence from wells which contain target cells plus effector cells and maximum release is the fluorescence from wells containing target cells and have been treated with 2% Triton-X.

Figure 21:
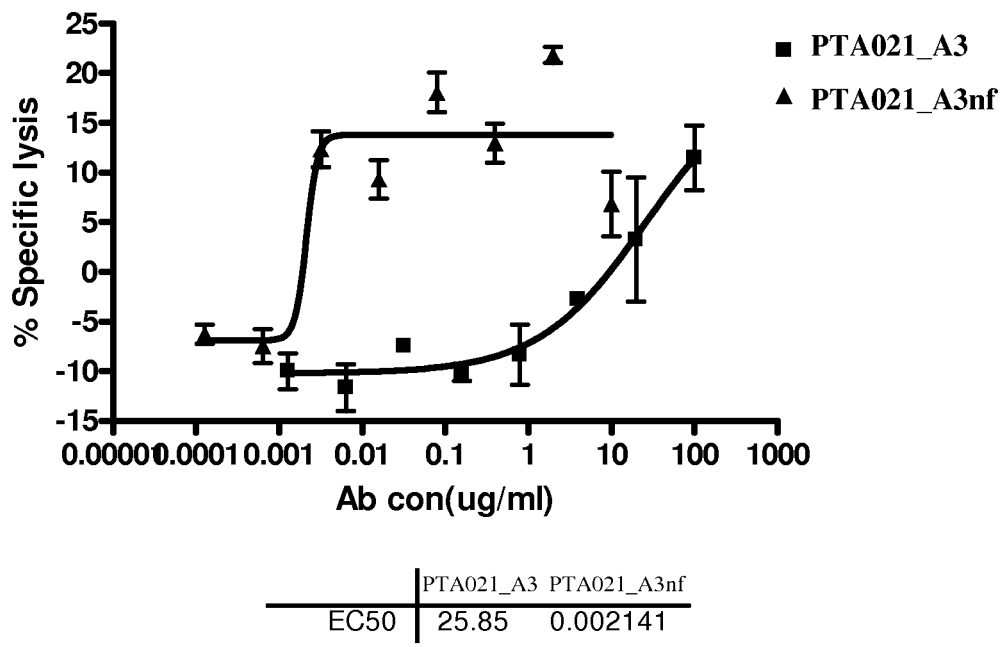
FIGS. 21, 22 and 23 present graphs showing ADCC activity of PTA021_A3 and non-fucosylated PTA021_A3 upon HepG2, 786-O and DMS79 cells, respectively.
Figure 22:
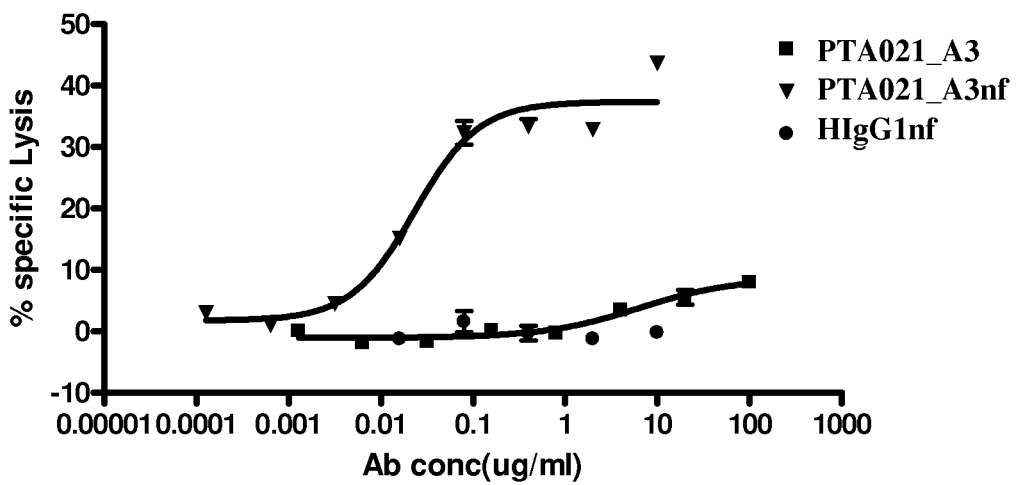
Figure 23:
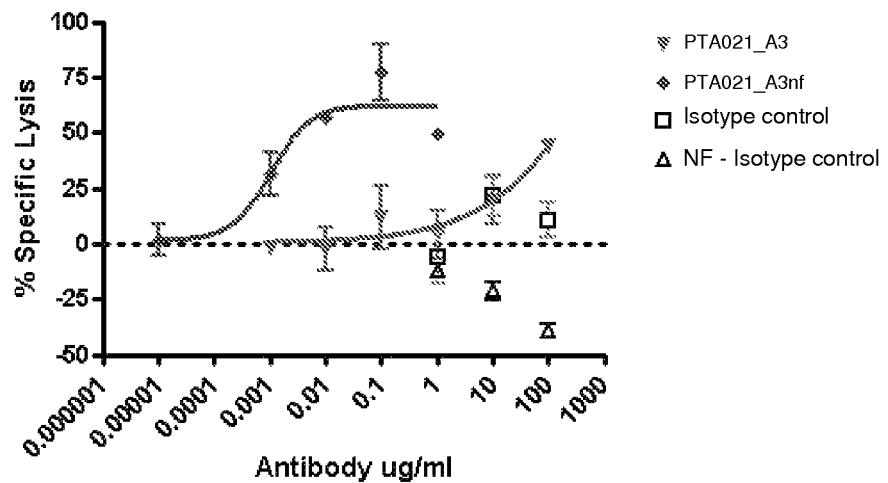

FIGS. 21, 22 and 23 show both PTA021_A3 and non-fucosylated PTA021_A3 are capable of eliciting ADCC on HepG2, 786-O and DMS79 cells and that the non-fucosylated PTA021_A3 is the more potent antibody. The same effect can be observed on other cell lines that express CADM1 such as the SCLC line NCI-H69.

Example 12

Anti-CADM1 Antibody/Cisplatin Inhibits DMS79 Cell Growth in a Mouse Xenograft Model The effect of PTA021_A3 alone and in combination with cisplatin on the growth of SCLC derived DMS79 cells in a mouse xenograft model was examined. In this xenograft model, SCID mice (CB17, from Charles River Laboratories, Hollister, Calif.) were implanted with $5 \times 10^6$ DMS79 cells/mouse and the DMS79 cells were allowed to grow until the tumors reached an average of 200 mm3. The mice were then randomized and treated intraperitoneally (i.p.) as shown in the tumor volume plot.

Figure 24:
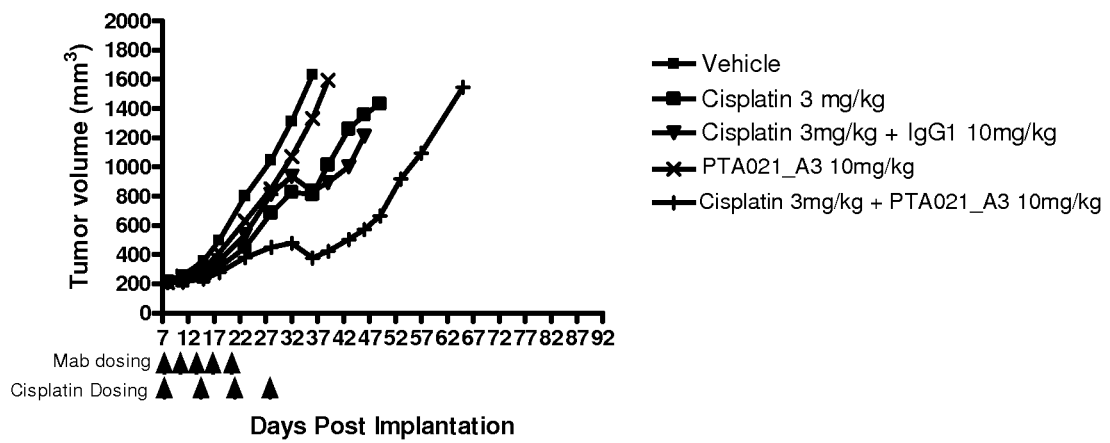
FIG. 24 presents a graph showing the effect of treatment with PTA021_A3 antibody alone or in combination with cisplatin on DMS79 tumor size in a mouse xenograft model.

As seen in FIG. 24, treatment with PTA021_A3 alone delays tumor growth, and in combination with cisplatin shows significant and synergistic anti-tumor activity

Example 13

Assessment of Toxicity of PTA021_A3NF, PTA021_A3, and PTA021_A3-Formula M

The toxicity profile of anti CADM1 antibodies, including nonfucosylated antibodies and antibody-drug conjugates, are assessed in cynomolgus macaques using e.g., PTA021_A3 and its derivatives. IHC assay results have shown that cynomolgus monkeys and humans show similar patterns of expression of CADM1 when subjected to IHC using PTA021_A3. Additionally, the CADM1 protein shows high identity in cynos and humans. Multiple IV doses between e.g. 0.1 mg/kg and 100 mg/kg are used to determine a maximum tolerated dose for use to identify doses appropriate for clinical trials in humans.

An exploratory toxicology study was conducted on PTA021_A3 and the non-fucosylated version of PTA021_A3 (NF) in cynomolgus macaques. 8 four-year old non-naïve (naïve to biologics but had been previously treated in a small-molecule pharmacokinetic study) cynomolgus monkeys were used in the study assessed in two groups with two males and two females in each group. The animals in Group 1 were treated with the non-fucosylated PTA021_A3(NF) antibody in a single intravenous (IV) dose at 1 mg/kg. The animals in Group 2 were treated with the PTA021_A3 antibody in a single IV dose at 1 mg/kg.

Clinical observations and mortality/morbidity were assessed twice daily am and pm. Body weight, hematology and blood chemistry were analysed on days −11, 0, 1, 3, 8, 15 and 22. Hematology assessments included RBC, HGB, HCT, PLT, MCH, MCV, Reticulocytes, WBC and Differential Count. Blood chemistry assessments included AST, ALT, ALP, CRE, BUN, GLU, CHO, TP, ALB, TBIL, LDH, TG, Ca, P, A/G, K, Na and Cl.

There were no significant overt observations (e.g. feeding behaviour) during the study. There were no observable effects on neuroendocrine tissues (e.g. hormonal changes which would lead to behavioural changes and signs of distress). There was also no evidence of pain or tremor noted. FIGS. 25 to 32 show that all of the analyses conducted were within normal expected values.

Figure 25A:
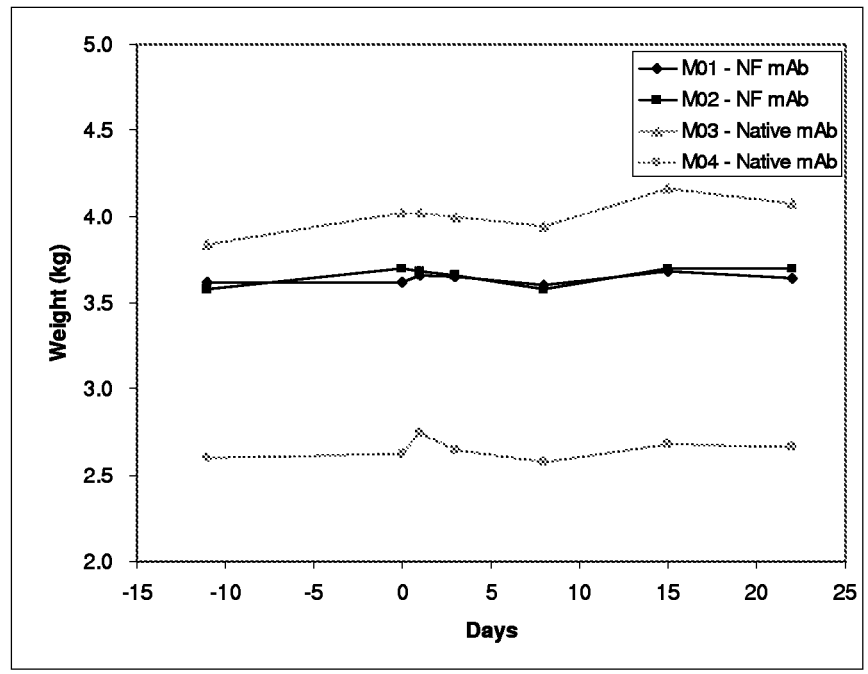
FIGS. 25A and 25B show the Body Weight data for male monkeys and female monkeys respectively in an exploratory toxicology study on PTA021_A3 and the non-fucosylated version of PTA021_A3(NF) in cynomolgus macaques.
Figure 25B:
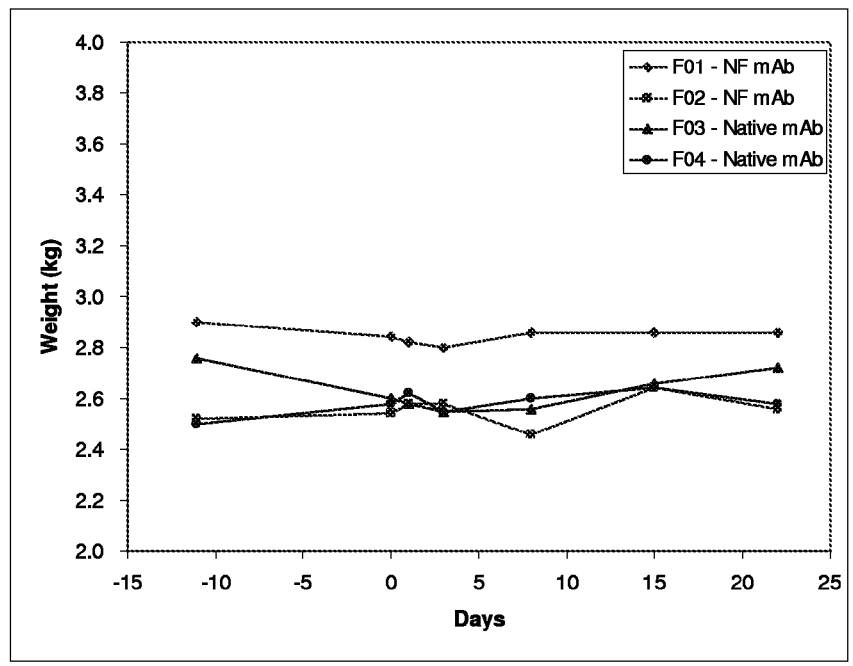

FIGS. 25A and 25B show the Body Weight data for male monkeys and female monkeys respectively.

Figure 26A:
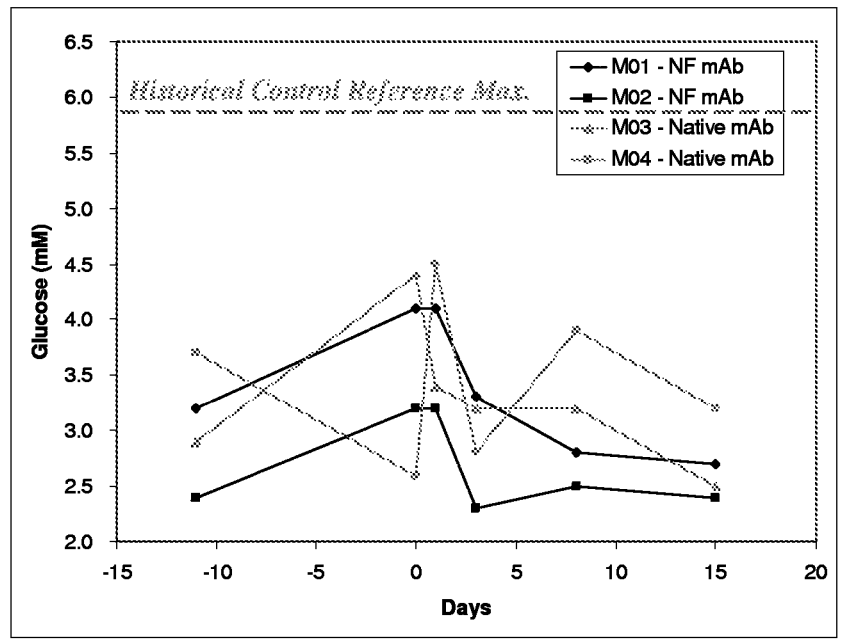
FIGS. 26A and 26B show the Glucose data for male monkeys and female monkeys respectively in an exploratory toxicology study on PTA021_A3 and the non-fucosylated version of PTA021_A3(NF) in cynomolgus macaques.
Figure 26B:
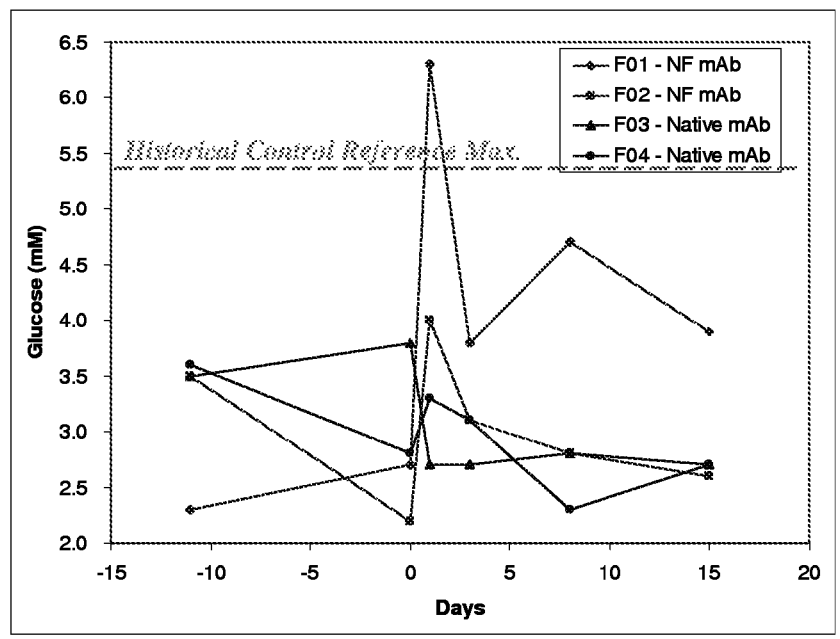

FIGS. 26A and 26B show the Glucose data for male monkeys and female monkeys respectively.

Figure 27A:
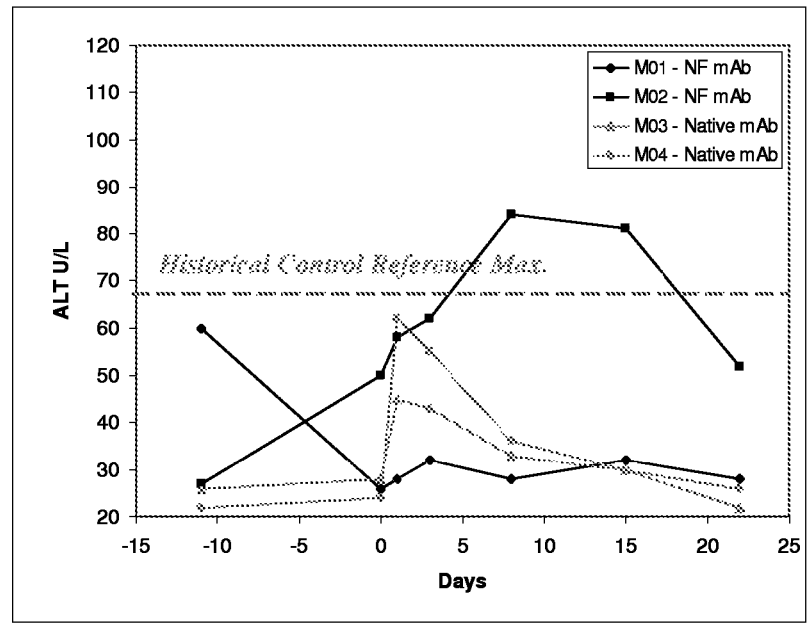
FIGS. 27A and 27B show the Alanine Transaminase data for male monkeys and female monkeys respectively in an exploratory toxicology study on PTA021_A3 and the non-fucosylated version of PTA021_A3(NF) in cynomolgus macaques.
Figure 27B:
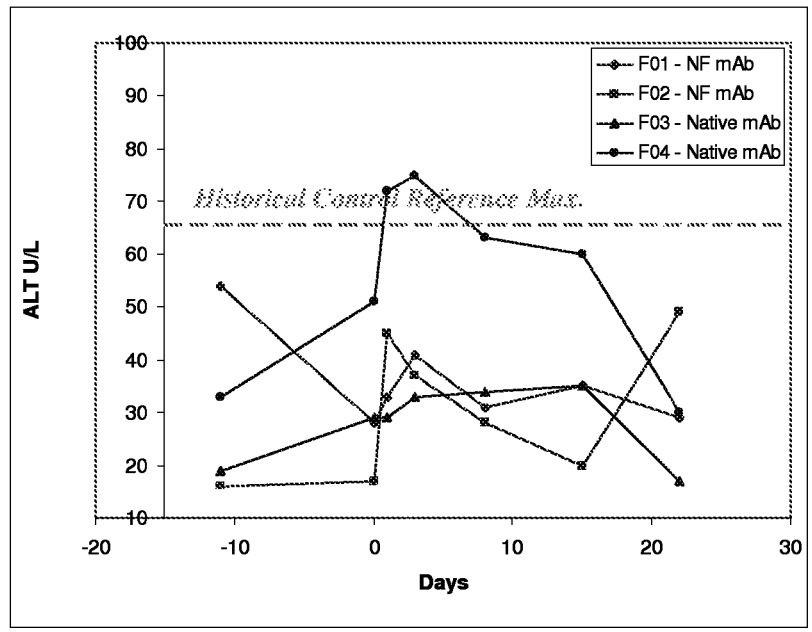

FIGS. 27A and 27B show the Alanine Transaminase data for male monkeys and female monkeys respectively.

Figure 28A:
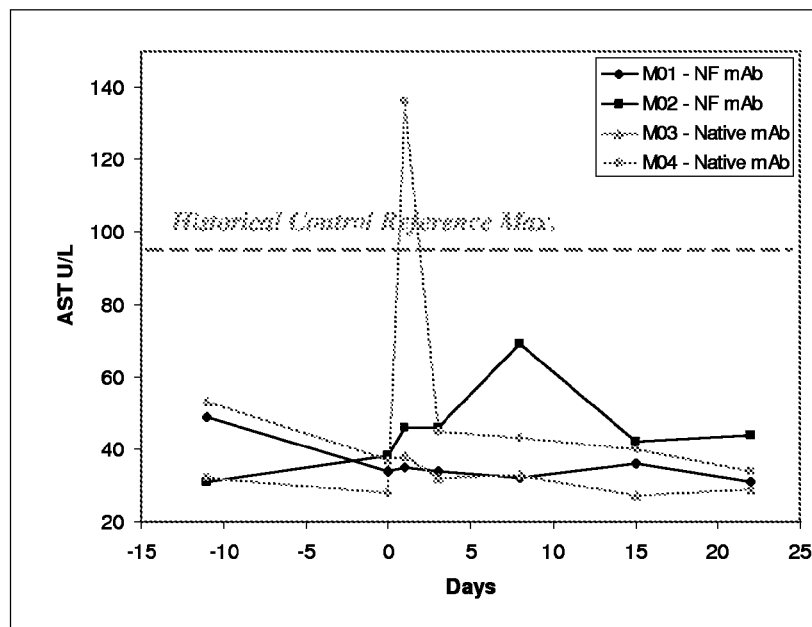
FIGS. 28A and 28B show the Aspartate Transaminase data for male monkeys and female monkeys respectively in an exploratory toxicology study on PTA021_A3 and the non-fucosylated version of PTA021_A3(NF) in cynomolgus macaques.
Figure 28B:
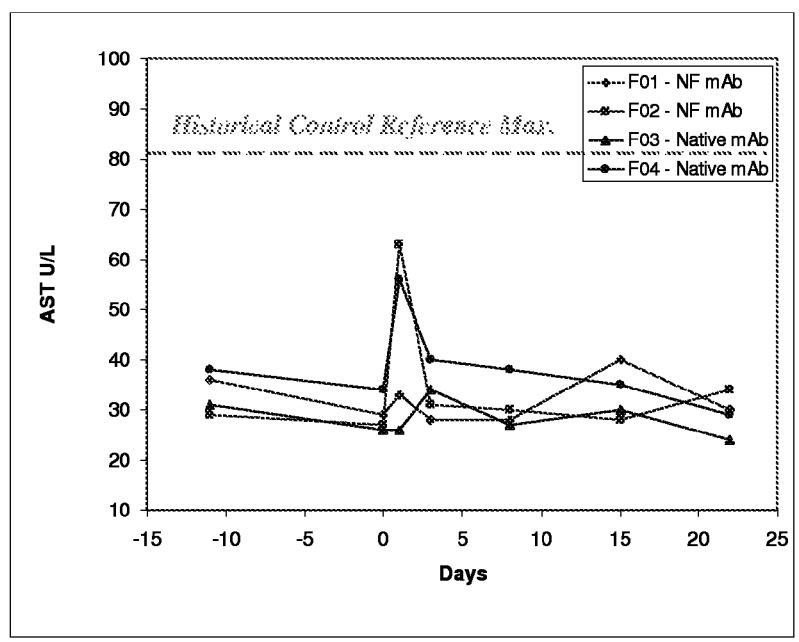

FIGS. 28A and 28B show the Aspartate Transaminase data for male monkeys and female monkeys respectively.

Figure 29A:
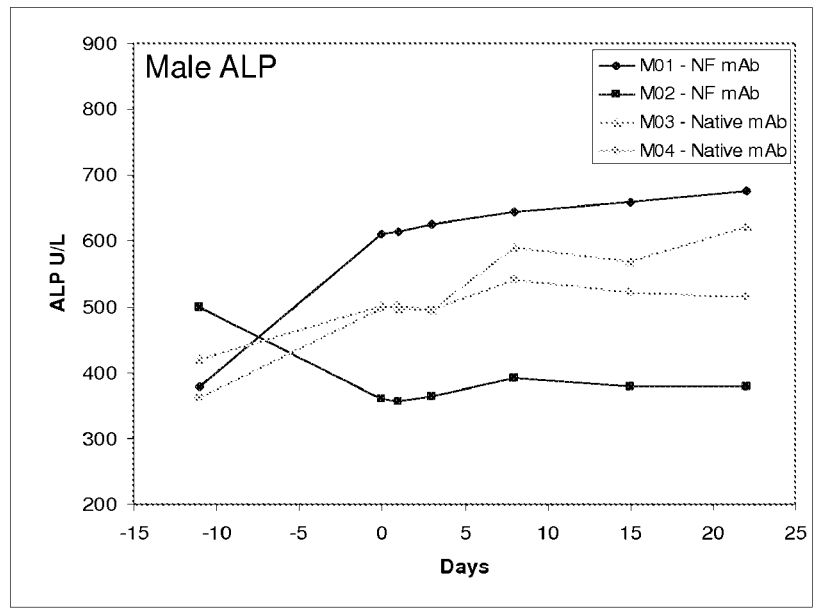
FIGS. 29A and 29B show the Alkaline Phosphatase data for male monkeys and female monkeys respectively in an exploratory toxicology study on PTA021_A3 and the non-fucosylated version of PTA021_A3(NF) in cynomolgus macaques.
Figure 29B:
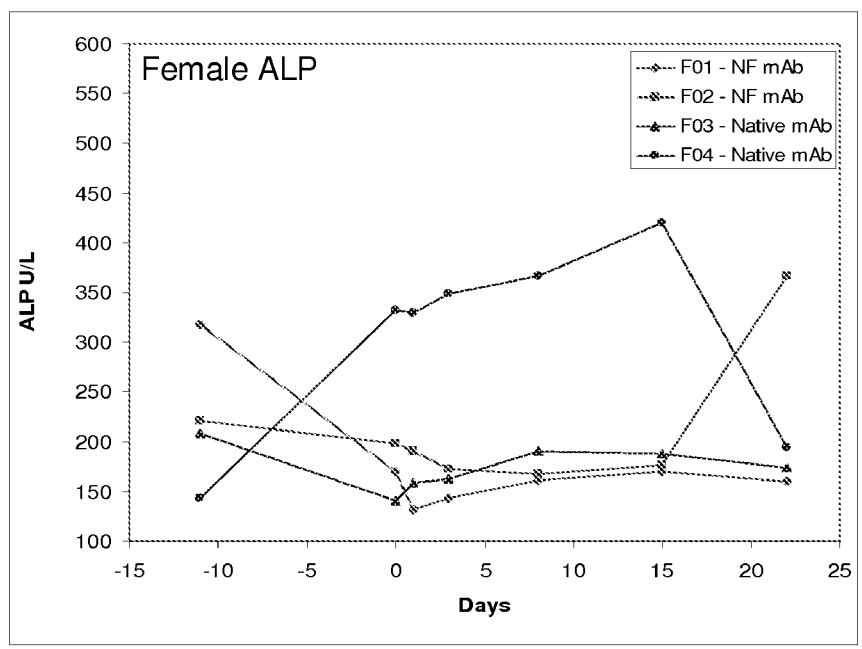

FIGS. 29A and 29B show the Alkaline Phosphatase data for male monkeys and female monkeys respectively.

Figure 30A:
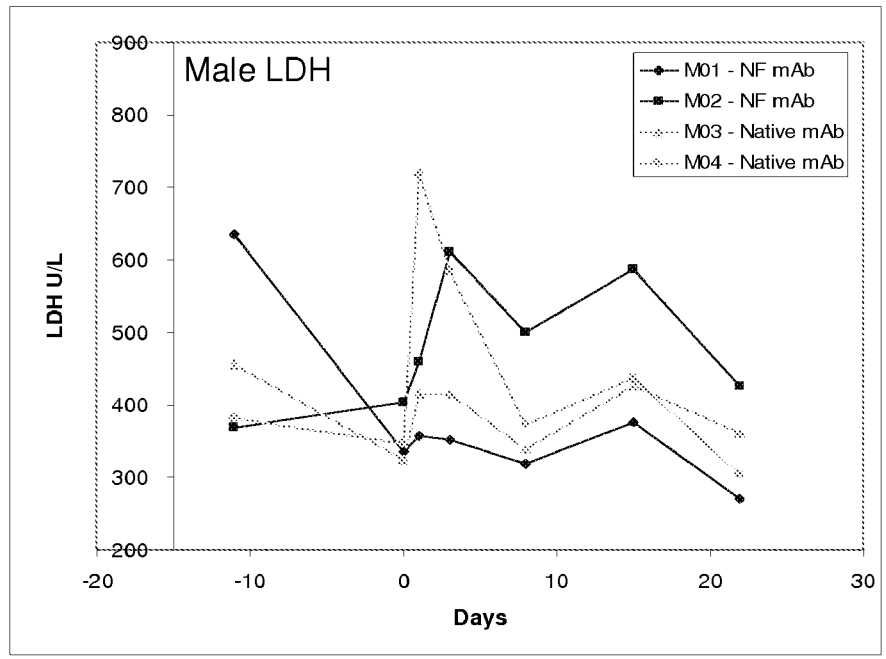
FIGS. 30A and 30B show the Lactate Dehydrogenase data for male monkeys and female monkeys respectively in an exploratory toxicology study on PTA021_A3 and the non-fucosylated version of PTA021_A3(NF) in cynomolgus macaques.
Figure 30B:
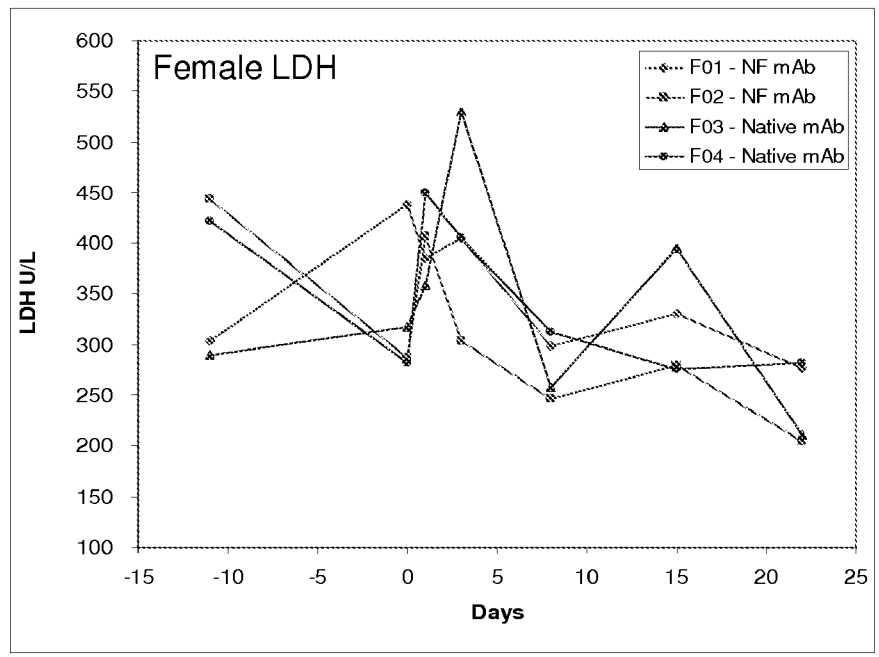

FIGS. 30A and 30B show the Lactate Dehydrogenase data for male monkeys and female monkeys respectively.

Figure 31A:
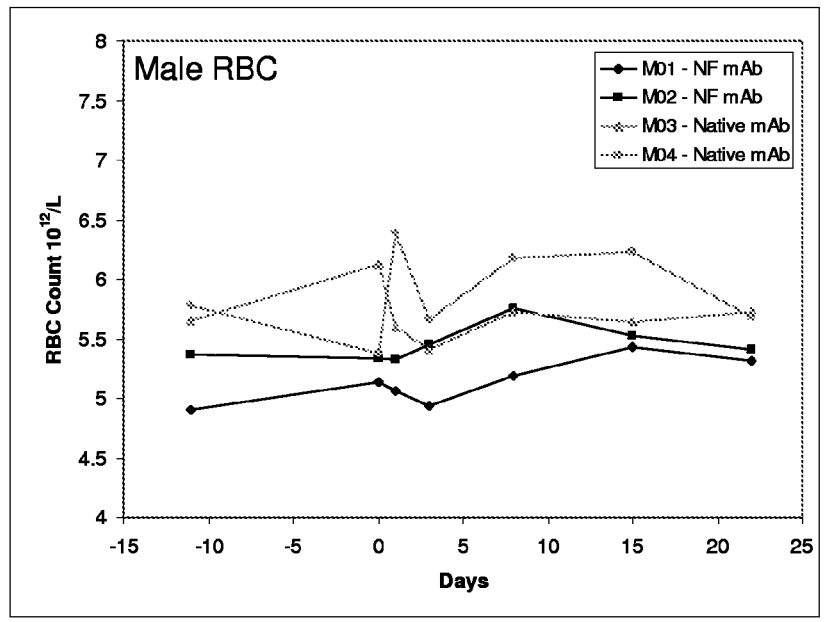
FIGS. 31A and 31B show the RBC data for male monkeys and female monkeys respectively in an exploratory toxicology study on PTA021_A3 and the non-fucosylated version of PTA021_A3(NF) in cynomolgus macaques.
Figure 31B:
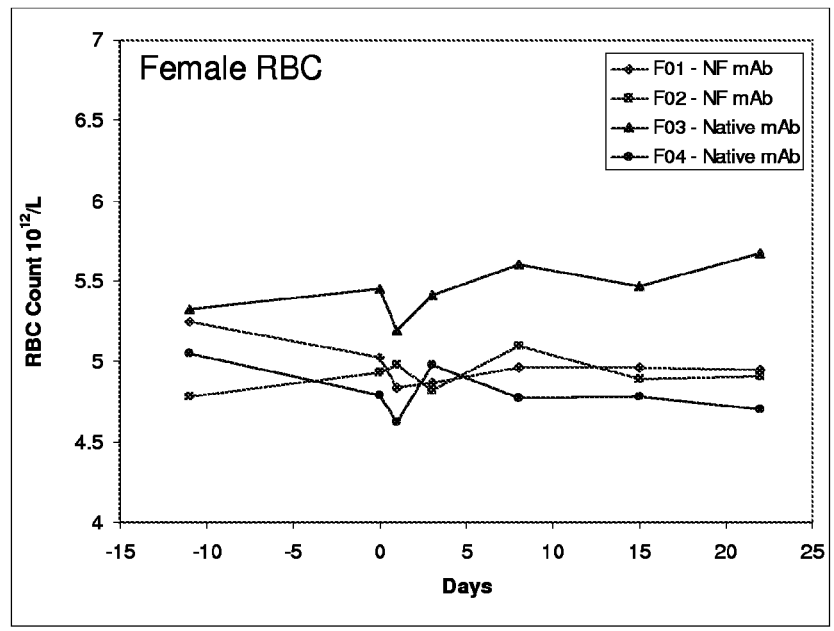

FIGS. 31A and 31B show the RBC data for male monkeys and female monkeys respectively.

Figure 32A:
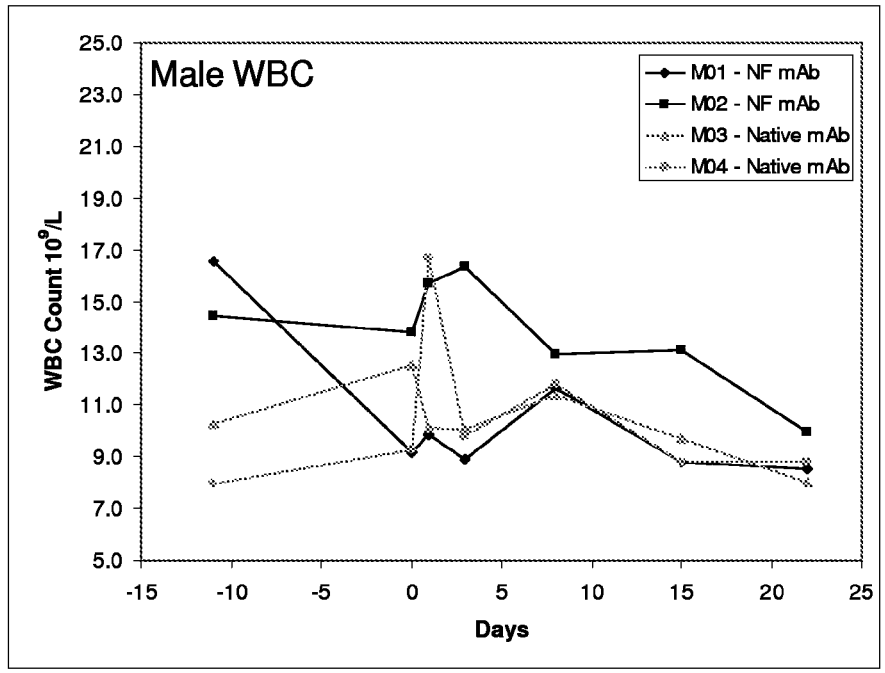
FIGS. 32A and 32B show the WBC data for male monkeys and female monkeys respectively in an exploratory toxicology study on PTA021_A3 and the non-fucosylated version of PTA021_A3(NF) in cynomolgus macaques.
Figure 32B:
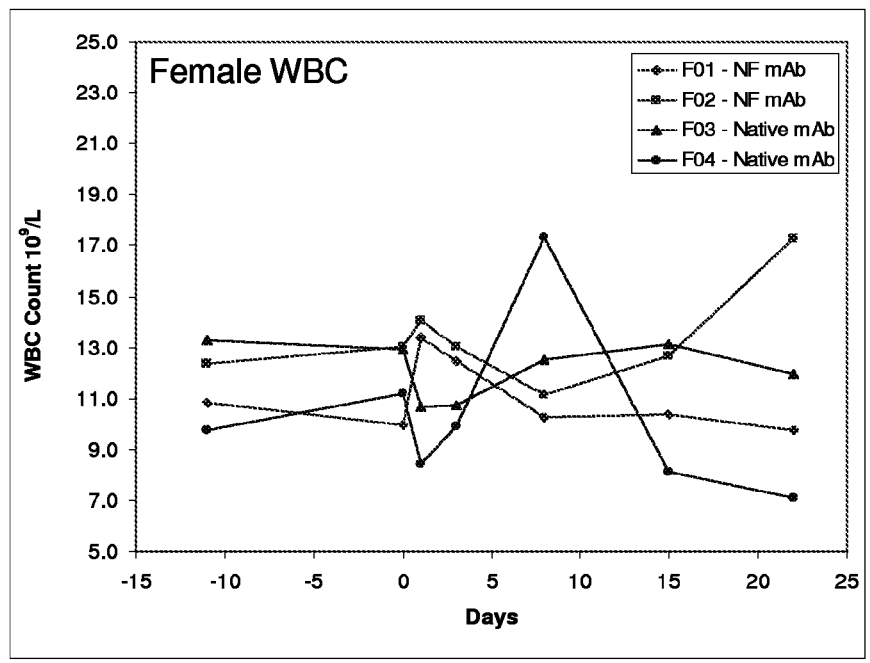

FIGS. 32A and 32B show the WBC data for male monkeys and female monkeys respectively.

Example 14

Assessment of Efficacy of PTA021_A3NF, PTA021_A3, and PTA021_A3-Formula M

CADM1 has been shown to be expressed in many cancer types by IHC using the PTA021_A3 HuMAb. Cell lines representing cancer tumor models are used to demonstrate efficacy of naked and toxin conjugated anti CADM1 antibodies to treat various cancers. For example, PTA021_A3 and derivatives thereof are used by themselves or in combination with standards of care in efficacy models of renal cancer (786-O cells), melanoma (SkMel28 cells) and small cell lung cancer (DMS79 cells) where CADM1 is expressed. PTA021_A3 and other anti-CADM1 antibodies may be used with xenograft animal models using CADM1-expressing cell lines representing cancers such as neuroendocrine cancers, colon cancer, breast cancer, ovarian cancer, and prostate cancer.

All references cited in this specification, including without limitation all papers, publications, patents, patent applications, presentations, texts, reports, manuscripts, brochures, books, internet postings, journal articles, periodicals, product fact sheets, and the like, one hereby incorporated by reference into this specification in their entireties. The discussion of the references herein is intended to merely summarize the assertions made by their authors and no admission is made that any reference constitutes prior art and Applicants' reserve the right to challenge the accuracy and pertinence of the cited references.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the dependant claims.

| SUMMARY OF SEQUENCE LISTING | |
|---|---|
| SEQ ID NO: | SEQUENCE |
| 1 | $V_H$ CDR1 amino acid PTA021_A1 |
| 2 | $V_H$ CDR1 amino acid PTA021_A2 |
| 3 | $V_H$ CDR1 amino acid PTA021_A3 |

-continued

SUMMARY OF SEQUENCE LISTING

| SEQ ID NO: | SEQUENCE |
|---|---|
| 4 | $V_H$ CDR2 amino acid PTA021_A1 |
| 5 | $V_H$ CDR2 amino acid PTA021_A2 |
| 6 | $V_H$ CDR2 amino acid PTA021_A3 |
| 7 | $V_H$ CDR3 amino acid PTA021_A1 |
| 8 | $V_H$ CDR3 amino acid PTA021_A2 |
| 9 | $V_H$ CDR3 amino acid PTA021_A3 |
| 10 | $V_K$ CDR1 amino acid PTA021_A1 |
| 11 | $V_K$ CDR1 amino acid PTA021_A2 |
| 12 | $V_K$ CDR1 amino acid PTA021_A3 |
| 13 | $V_K$ CDR2 amino acid PTA021_A1 |
| 14 | $V_K$ CDR2 amino acid PTA021_A2 |
| 15 | $V_K$ CDR2 amino acid PTA021_A3 |
| 16 | $V_K$ CDR3 amino acid PTA021_A1 |
| 17 | $V_K$ CDR3 amino acid PTA021_A2 |
| 18 | $V_K$ CDR3 amino acid PTA021_A3 |
| 19 | $V_H$ amino acid PTA021_A1 |
| 20 | $V_H$ amino acid PTA021_A2 |
| 21 | $V_H$ amino acid PTA021_A3 |
| 22 | VK amino acid PTA021_A1 |

-continued

SUMMARY OF SEQUENCE LISTING

| SEQ ID NO: | SEQUENCE |
|---|---|
| 23 | VK amino acid PTA021_A2 |
| 24 | VK amino acid PTA021_A3 |
| 25 | $V_H$ n.t. PTA021_A1 |
| 26 | $V_H$ n.t. PTA021_A2 |
| 27 | $V_H$ n.t. PTA021_A3 |
| 28 | $V_K$ n.t. PTA021_A1 |
| 29 | $V_K$ n.t. PTA021_A2 |
| 30 | $V_K$ n.t. PTA021_A3 |
| 31 | $V_H$ 2-05 germline amino acid |
| 32 | $V_H$ 2-05 germline amino acid |
| 33 | $V_H$ 2-05 germline amino acid |
| 34 | $V_K$ L15 germline amino acid |
| 35 | $V_K$ L15 germline amino acid |
| 36 | $V_K$ L15 germline amino acid |
| 37 | $V_H$ JH5b germline amino acid |
| 38 | $V_H$ JH5b germline amino acid |
| 39 | $V_H$ JH5b germline amino acid |
| 40 | JK4 germline amino acid |
| 41 | JK4 germline amino acid |
| 42 | JK4 germline amino acid |

-continued

SUMMARY OF SEQUENCE LISTING

| SEQ ID NO: | SEQUENCE |
|---|---|
| 43 | CADM1 construct |
| 44 | CADM1 ECD-6HIS |
| 45 | Conjugate peptide |

What is claimed:

1. An isolated monoclonal antibody, or an antigen-binding portion thereof, which binds human CADM1 and which comprises heavy and light chain variable regions, wherein the regions are selected from the group consisting of:
   (a) a heavy chain variable region comprising the amino acid sequence set forth in SEQ ID NO:19, 20, or 21;
   (b) a light chain variable region comprising the amino acid sequence set forth in SEQ ID NO:22, 23, or 24;
   (c) a heavy chain variable region CDR1 comprising SEQ ID NO:1, a heavy chain variable region CDR2 comprising SEQ ID NO:4, a heavy chain variable region CDR3 comprising SEQ ID NO:7, a light chain variable region CDR1 comprising SEQ ID NO:10, a light chain variable region CDR2 comprising SEQ ID NO:13 and a light chain variable region CDR3 comprising SEQ ID NO:16;
   (d) a heavy chain variable region CDR1 comprising SEQ ID NO:2, a heavy chain variable region CDR2 comprising SEQ ID NO:5, a heavy chain variable region CDR3 comprising SEQ ID NO:8, a light chain variable region CDR1 comprising SEQ ID NO:11, a light chain variable region CDR2 comprising SEQ ID NO:14 and a light chain variable region CDR3 comprising SEQ ID NO:17;
   (e) a heavy chain variable region CDR1 comprising SEQ ID NO:3, a heavy chain variable region CDR2 comprising SEQ ID NO:6, a heavy chain variable region CDR3 comprising SEQ ID NO:9, a light chain variable region CDR1 comprising SEQ ID NO:12, a light chain variable region CDR2 comprising SEQ ID NO:15 and a light chain variable region CDR3 comprising SEQ ID NO:18;
   (f) heavy and light chain variable regions comprising the amino acid sequences set forth in SEQ ID NOs:19 and 22, respectively;
   (g) heavy and light chain variable regions comprising the amino acid sequences set forth in SEQ ID NOs:20 and 23, respectively; and
   (h) heavy and light chain variable regions comprising the amino acid sequences set forth in SEQ ID NOs:21 and 24, respectively.

2. The antibody of claim 1, wherein said antibody is a full-length antibody of an IgG1, IgG2, IgG3, or IgG4 isotype.

3. The antibody of claim 1, wherein said antibody is selected from the group consisting of: a whole antibody, an antibody fragment, a humanized antibody, a human antibody, a single chain antibody, an engineered antibody resulting in increased binding to Fc receptors and/or increased potency for ADCC, and a bispecific antibody.

4. The antibody of claim 1 which is conjugated to a therapeutic agent.

5. The antibody of claim 4 wherein the therapeutic agent is a cytotoxin or a radioactive isotope.

6. The isolated antibody of claim 1, wherein said antibody binds to human CADM1 with an $EC_{50}$ in the range of <50 nM, <10 nM, or <1 nM.

7. A composition comprising the isolated antibody or antigen-binding portion thereof of claim 1 and a pharmaceutically acceptable carrier.

8. A hybridoma expressing the antibody or antigen binding portion thereof of claim 1.

9. The isolated monoclonal antibody, or an antigen-binding portion thereof, of claim 1, comprising a heavy chain variable region comprising the amino acid sequence set forth in SEQ ID NO:19.

10. The isolated monoclonal antibody, or an antigen-binding portion thereof, of claim 1, comprising a heavy chain variable region comprising the amino acid sequence set forth in SEQ ID NO:20.

11. The isolated monoclonal antibody, or an antigen-binding portion thereof, of claim 1, comprising a heavy chain variable region comprising the amino acid sequence set forth in SEQ ID NO:21.

12. The isolated monoclonal antibody, or an antigen-binding portion thereof, of claim 1, comprising a light chain variable region comprising the amino acid sequence set forth in SEQ ID NO:22.

13. The isolated monoclonal antibody, or an antigen-binding portion thereof, of claim 1, comprising a light chain variable region comprising the amino acid sequence set forth in SEQ ID NO:23.

14. The isolated monoclonal antibody, or an antigen-binding portion thereof, of claim 1, comprising a light chain variable region comprising the amino acid sequence set forth in SEQ ID NO:24.

15. The isolated monoclonal antibody, or an antigen-binding portion thereof, of claim 1, comprising a heavy chain variable region CDR1 comprising SEQ ID NO:1, a heavy chain variable region CDR2 comprising SEQ ID NO:4, a heavy chain variable region CDR3 comprising SEQ ID NO:7, a light chain variable region CDR1 comprising SEQ ID NO:10, a light chain variable region CDR2 comprising SEQ ID NO:13 and a light chain variable region CDR3 comprising SEQ ID NO:16.

16. The isolated monoclonal antibody, or an antigen-binding portion thereof, of claim 1, comprising a heavy chain variable region CDR1 comprising SEQ ID NO:2, a heavy chain variable region CDR2 comprising SEQ ID NO:5, a heavy chain variable region CDR3 comprising SEQ ID NO:8, a light chain variable region CDR1 comprising SEQ ID NO:11, a light chain variable region CDR2 comprising SEQ ID NO:14 and a light chain variable region CDR3 comprising SEQ ID NO:17.

17. The isolated monoclonal antibody, or an antigen-binding portion thereof, of claim 1, comprising a heavy chain variable region CDR1 comprising SEQ ID NO:3, a heavy chain variable region CDR2 comprising SEQ ID NO:6, a heavy chain variable region CDR3 comprising SEQ ID NO:9, a light chain variable region CDR1 comprising SEQ ID NO:12, a light chain variable region CDR2 comprising SEQ ID NO:15 and a light chain variable region CDR3 comprising SEQ ID NO:18.

18. The isolated monoclonal antibody, or an antigen-binding portion thereof, of claim 1, comprising heavy and light chain variable regions comprising the amino acid sequences set forth in SEQ ID NOs:19 and 22, respectively.

19. The isolated monoclonal antibody, or an antigen-binding portion thereof, of claim 1, comprising heavy and light chain variable regions comprising the amino acid sequences set forth in SEQ ID NOs:20 and 23, respectively.

20. The isolated monoclonal antibody, or an antigen-binding portion thereof, of claim 1, comprising heavy and light chain variable regions comprising the amino acid sequences set forth in SEQ ID NOs:21 and 24, respectively.

21. A method for treating a disease associated with target cells expressing CADM1, wherein the disease associated with target cells expressing CADM1 is a cancer, said method comprising the step of administering to a subject the anti-CADM1 antibody, or antigen-binding portion thereof, of claim 1, wherein said antibody or antigen-binding portion thereof is conjugated to a therapeutic agent, in an amount effective to treat the disease.

22. The method of claim 21, wherein said cancer is selected from the group consisting of: small cell lung cancer, adult T-cell leukemia, non-small cell lung cancer (including squamous carcinomas and adenocarcinomas), melanoma, breast cancer, colorectal cancer, ovarian cancer, prostate cancer, neuroendocrine cancers including those of lung, adrenal, pituitary, GI-tract, kidney, liver (including hepatocellular carcinomas), pancreas (including insulinomas and glucagonomas), glioblastomas, and carcinoid tumors including those of the pancreas, lung, GI tract, liver, and kidney.

* * * * *

SEQUENCE LISTING

<160> NUMBER OF SEQ ID NOS: 46

<210> SEQ ID NO 1
<211> LENGTH: 7
<212> TYPE: PRT
<213> ORGANISM: Homo sapiens

<400> SEQUENCE: 1

Thr Ser Gly Val Gly Val Gly
1               5

<210> SEQ ID NO 2
<211> LENGTH: 7
<212> TYPE: PRT
<213> ORGANISM: Homo sapiens

<400> SEQUENCE: 2

Thr Ser Gly Val Gly Val Gly
1               5

<210> SEQ ID NO 3
<211> LENGTH: 7
<212> TYPE: PRT
<213> ORGANISM: Homo sapiens

<400> SEQUENCE: 3

Thr Ser Gly Val Gly Val Gly
1               5

<210> SEQ ID NO 4
<211> LENGTH: 16
<212> TYPE: PRT
<213> ORGANISM: Homo sapiens

<400> SEQUENCE: 4

Leu Ile Tyr Trp Asp Asp Asp Lys Arg Tyr Ser Pro Ser Leu Lys Ser
1               5                   10                  15

<210> SEQ ID NO 5
<211> LENGTH: 16
<212> TYPE: PRT
<213> ORGANISM: Homo sapiens

<400> SEQUENCE: 5

Leu Ile Tyr Trp Asp Asp Asp Lys Arg Tyr Ser Pro Ser Leu Lys Ser
1               5                   10                  15

<210> SEQ ID NO 6
<211> LENGTH: 16
<212> TYPE: PRT
<213> ORGANISM: Homo sapiens

-continued

```
<400> SEQUENCE: 6

Leu Ile Tyr Trp Asp Asp Lys Arg Tyr Ser Pro Ser Leu Lys Ser
1               5                   10                  15

<210> SEQ ID NO 7
<211> LENGTH: 15
<212> TYPE: PRT
<213> ORGANISM: Homo sapiens

<400> SEQUENCE: 7

Arg Arg Val Glu Trp Val Ala Leu Ala Gly Asn Trp Phe Asp Pro
1               5                   10                  15

<210> SEQ ID NO 8
<211> LENGTH: 15
<212> TYPE: PRT
<213> ORGANISM: Homo sapiens

<400> SEQUENCE: 8

Arg Arg Val Glu Trp Phe Ala Leu Ala Gly Asn Trp Phe Asp Pro
1               5                   10                  15

<210> SEQ ID NO 9
<211> LENGTH: 15
<212> TYPE: PRT
<213> ORGANISM: Homo sapiens

<400> SEQUENCE: 9

Arg Arg Val Glu Trp Val Thr Leu Ala Gly Asn Trp Phe Asp Pro
1               5                   10                  15

<210> SEQ ID NO 10
<211> LENGTH: 11
<212> TYPE: PRT
<213> ORGANISM: Homo sapiens

<400> SEQUENCE: 10

Arg Ala Ser Gln Gly Ile Ser Ser Trp Leu Ala
1               5                   10

<210> SEQ ID NO 11
<211> LENGTH: 11
<212> TYPE: PRT
<213> ORGANISM: Homo sapiens

<400> SEQUENCE: 11

Arg Ala Ser Gln Gly Ile Ser Ser Trp Leu Ala
1               5                   10

<210> SEQ ID NO 12
<211> LENGTH: 11
<212> TYPE: PRT
<213> ORGANISM: Homo sapiens

<400> SEQUENCE: 12

Arg Ala Ser Gln Gly Ile Ser Ser Trp Leu Ala
1               5                   10

<210> SEQ ID NO 13
<211> LENGTH: 7
<212> TYPE: PRT
<213> ORGANISM: Homo sapiens

<400> SEQUENCE: 13

Gly Ala Ser Ser Leu Gln Ser
```

-continued

```
<210> SEQ ID NO 14
<211> LENGTH: 7
<212> TYPE: PRT
<213> ORGANISM: Homo sapiens

<400> SEQUENCE: 14

Ala Ala Ser Ser Leu Gln Ser
1               5

<210> SEQ ID NO 15
<211> LENGTH: 7
<212> TYPE: PRT
<213> ORGANISM: Homo sapiens

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Homo sapiens

<400> SEQUENCE: 16

Gln Gln Tyr Asn Ser Tyr Pro Leu Thr
1               5

<210> SEQ ID NO 17
<211> LENGTH: 9
<212> TYPE: PRT
<213> ORGANISM: Homo sapiens

<400> SEQUENCE: 17

Gln Gln Tyr Asn Ser Tyr Pro Leu Thr
1               5

<210> SEQ ID NO 18
<211> LENGTH: 9
<212> TYPE: PRT
<213> ORGANISM: Homo sapiens

<400> SEQUENCE: 18

Gln Gln Tyr Asn Ser Tyr Pro Leu Thr
1               5

<210> SEQ ID NO 19
<211> LENGTH: 125
<212> TYPE: PRT
<213> ORGANISM: Homo sapiens

<400> SEQUENCE: 19

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Ser
                20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
        50                  55                  60

Leu Lys Ser Arg Leu Thr Ile Thr Lys Asp Thr Ser Lys Asn Gln Val
65                  70                  75                  80
```

```
Val Leu Thr Met Thr Asn Met Asp Pro Val Asp Thr Ala Thr Tyr Tyr
                85                  90                  95

Cys Ala His Arg Arg Val Glu Trp Val Ala Leu Ala Gly Asn Trp Phe
            100                 105                 110

Asp Pro Trp Gly Gln Gly Thr Leu Val Thr Val Ser Ser
            115                 120             125
```

<210> SEQ ID NO 20
<211> LENGTH: 125
<212> TYPE: PRT
<213> ORGANISM: Homo sapiens

<400> SEQUENCE: 20

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Ile Tyr Tyr
                85                  90                  95

Cys Ala His Arg Arg Val Glu Trp Phe Ala Leu Ala Gly Asn Trp Phe
            100                 105                 110

Asp Pro Trp Gly Gln Gly Ser Leu Val Thr Val Ser Ser
            115                 120             125
```

<210> SEQ ID NO 21
<211> LENGTH: 125
<212> TYPE: PRT
<213> ORGANISM: Homo sapiens

<400> SEQUENCE: 21

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Val Glu Trp Val Thr Leu Ala Gly Asn Trp Phe
            100                 105                 110

Asp Pro Trp Gly Gln Gly Thr Leu Val Thr Val Ser Ser
            115                 120             125
```

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 23
<211> LENGTH: 107
<212> TYPE: PRT
<213> ORGANISM: Homo sapiens

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 25
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 25

| | | | | | | | | | | | | | | | | |
|---|---|---|---|---|---|---|---|---|---|---|---|---|---|---|---|---|
| cag | atc | acc | ttg | aag | gag | tct | ggt | cct | acg | ctg | gtg | aaa | ccc | aca | cag | 48 |
| Gln | Ile | Thr | Leu | Lys | Glu | Ser | Gly | Pro | Thr | Leu | Val | Lys | Pro | Thr | Gln | |
| 1 | | | | 5 | | | | | 10 | | | | | 15 | | |
| acc | ctc | acg | ctg | acc | tgc | acc | ttc | tct | ggg | ttc | tca | ctc | aat | act | agt | 96 |
| Thr | Leu | Thr | Leu | Thr | Cys | Thr | Phe | Ser | Gly | Phe | Ser | Leu | Asn | Thr | Ser | |
| | | | 20 | | | | | 25 | | | | | 30 | | | |
| gga | gtg | ggt | gtg | ggc | tgg | atc | cgt | cag | ccc | cca | gga | aag | gcc | ctg | gag | 144 |
| Gly | Val | Gly | Val | Gly | Trp | Ile | Arg | Gln | Pro | Pro | Gly | Lys | Ala | Leu | Glu | |
| | | 35 | | | | | 40 | | | | | 45 | | | | |
| tgg | ctt | gca | ctc | att | tat | tgg | gac | gat | gat | aag | cgc | tac | agc | cca | tct | 192 |
| Trp | Leu | Ala | Leu | Ile | Tyr | Trp | Asp | Asp | Asp | Lys | Arg | Tyr | Ser | Pro | Ser | |
| 50 | | | | | 55 | | | | | 60 | | | | | | |
| ctg | aag | agc | agg | ctc | acc | atc | acc | aag | gac | acc | tcc | aaa | aac | cag | gtg | 240 |
| Leu | Lys | Ser | Arg | Leu | Thr | Ile | Thr | Lys | Asp | Thr | Ser | Lys | Asn | Gln | Val | |
| 65 | | | | | 70 | | | | | 75 | | | | | 80 | |
| gtc | ctt | aca | atg | acc | aac | atg | gac | cct | gtg | gac | aca | gcc | aca | tat | tac | 288 |
| Val | Leu | Thr | Met | Thr | Asn | Met | Asp | Pro | Val | Asp | Thr | Ala | Thr | Tyr | Tyr | |
| | | | | 85 | | | | | 90 | | | | | 95 | | |
| tgt | gca | cac | agg | aga | gtt | gaa | tgg | gtc | gcc | ctg | gca | ggg | aac | tgg | ttc | 336 |
| Cys | Ala | His | Arg | Arg | Val | Glu | Trp | Val | Ala | Leu | Ala | Gly | Asn | Trp | Phe | |
| | | | 100 | | | | | 105 | | | | | 110 | | | |
| gac | ccc | tgg | ggc | cag | gga | acc | ctg | gtc | acc | gtc | tcc | tca | | | | 375 |
| Asp | Pro | Trp | Gly | Gln | Gly | Thr | Leu | Val | Thr | Val | Ser | Ser | | | | |
| | | 115 | | | | | 120 | | | | | 125 | | | | |

<210> SEQ ID NO 26
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 26

| | | | | | | | | | | | | | | | | |
|---|---|---|---|---|---|---|---|---|---|---|---|---|---|---|---|---|
| cag | atc | acc | ttg | aag | gag | tct | ggt | cct | acg | ctg | gtg | aaa | ccc | aca | cag | 48 |
| Gln | Ile | Thr | Leu | Lys | Glu | Ser | Gly | Pro | Thr | Leu | Val | Lys | Pro | Thr | Gln | |
| 1 | | | | 5 | | | | | 10 | | | | | 15 | | |
| acc | ctc | acg | ctg | acc | tgc | acc | ttc | tct | ggg | ttc | tca | ctc | agc | act | agt | 96 |
| Thr | Leu | Thr | Leu | Thr | Cys | Thr | Phe | Ser | Gly | Phe | Ser | Leu | Ser | Thr | Ser | |
| | | | 20 | | | | | 25 | | | | | 30 | | | |
| gga | gtg | ggt | gtg | ggc | tgg | atc | cgt | cag | ccc | cca | gga | aag | gcc | ctg | gag | 144 |
| Gly | Val | Gly | Val | Gly | Trp | Ile | Arg | Gln | Pro | Pro | Gly | Lys | Ala | Leu | Glu | |
| | | 35 | | | | | 40 | | | | | 45 | | | | |
| tgg | ctt | gca | ctc | att | tat | tgg | gat | gat | gat | aag | cgc | tac | agc | cca | tct | 192 |
| Trp | Leu | Ala | Leu | Ile | Tyr | Trp | Asp | Asp | Asp | Lys | Arg | Tyr | Ser | Pro | Ser | |
| 50 | | | | | 55 | | | | | 60 | | | | | | |
| ctg | aag | agc | agg | ctc | acc | atc | acc | aag | gac | acc | tcc | aaa | aac | cag | gtg | 240 |
| Leu | Lys | Ser | Arg | Leu | Thr | Ile | Thr | Lys | Asp | Thr | Ser | Lys | Asn | Gln | Val | |
| 65 | | | | | 70 | | | | | 75 | | | | | 80 | |
| gtc | ctt | aca | atg | acc | aac | atg | gac | cct | gtg | gac | aca | gcc | ata | tat | tac | 288 |
| Val | Leu | Thr | Met | Thr | Asn | Met | Asp | Pro | Val | Asp | Thr | Ala | Ile | Tyr | Tyr | |
| | | | | 85 | | | | | 90 | | | | | 95 | | |
| tgt | gcg | cac | agg | aga | gtt | gag | tgg | ttc | gcc | ctg | gca | ggg | aac | tgg | ttc | 336 |
| Cys | Ala | His | Arg | Arg | Val | Glu | Trp | Phe | Ala | Leu | Ala | Gly | Asn | Trp | Phe | |

```
                100                 105                 110
gac ccc tgg ggc cag gga tcc ctg gtc acc gtc tca                      375
Asp Pro Trp Gly Gln Gly Ser Leu Val Thr Val Ser
        115                 120                 125

<210> SEQ ID NO 27
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 27 cag atc acc ttg aag gag tct ggt cct acg ctg gtg aaa ccc aca cag     48
Gln Ile Thr Leu Lys Glu Ser Gly Pro Thr Leu Val Lys Pro Thr Gln
1               5                   10                  15 acc ctc acg ctg acc tgc acc ttc tct ggg ttc tca ctc agt act agt     96
Thr Leu Thr Leu Thr Cys Thr Phe Ser Gly Phe Ser Leu Ser Thr Ser
            20                  25                  30 gga gtg ggt gtg ggc tgg atc cgt cag ccc cca gga aag gcc ctg gag    144
Gly Val Gly Val Gly Trp Ile Arg Gln Pro Pro Gly Lys Ala Leu Glu
        35                  40                  45 tgg ctt gca ctc att tat tgg gac gat gat aag cgc tac agc cca tct    192
Trp Leu Ala Leu Ile Tyr Trp Asp Asp Asp Lys Arg Tyr Ser Pro Ser
    50                  55                  60 ctg aag agc agg ctc acc atc acc aag gac acc tcc aaa aac cag gtg    240
Leu Lys Ser Arg Leu Thr Ile Thr Lys Asp Thr Ser Lys Asn Gln Val
65                  70                  75                  80 gtc ctt aca atg acc aac atg gac cct gtg gac aca gcc aca tat tac    288
Val Leu Thr Met Thr Asn Met Asp Pro Val Asp Thr Ala Thr Tyr Tyr
                85                  90                  95 tgt gca cac agg aga gtt gag tgg gtc acc ctg gca ggg aac tgg ttc    336
Cys Ala His Arg Arg Val Glu Trp Val Thr Leu Ala Gly Asn Trp Phe
            100                 105                 110 gac ccc tgg ggc cag gga acc ctg gtc acc gtc tca                    375
Asp Pro Trp Gly Gln Gly Thr Leu Val Thr Val Ser
        115                 120                 125

<210> SEQ ID NO 28
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 28 gac atc cag atg acc cag tct cca tcc tca ctg tct gca tct gta gga     48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg     96
Asp Arg Val Thr Ile Thr Cys Arg Ala Ser Gln Gly Ile Ser Ser Trp
            20                  25                  30 tta gcc tgg tat cag cag aaa cca gag aaa gcc cct aag tcc ctg atc    144
Leu Ala Trp Tyr Gln Gln Lys Pro Glu Lys Ala Pro Lys Ser Leu Ile
        35                  40                  45 tat ggt gca tcc agt ttg caa agt ggg gtc cca tca agg ttc agc ggc    192
Tyr Gly Ala Ser Ser Leu Gln Ser Gly Val Pro Ser Arg Phe Ser Gly
    50                  55                  60 agt gga tct ggg aca gat ttc act ctc acc atc agc aac ctg cag cct    240
Ser Gly Ser Gly Thr Asp Phe Thr Leu Thr Ile Ser Asn Leu Gln Pro
65                  70                  75                  80
```

```
gaa gat ttt gca act tat tac tgc caa cag tat aat agt tac cct ctc      288
Glu Asp Phe Ala Thr Tyr Tyr Cys Gln Gln Tyr Asn Ser Tyr Pro Leu
                85                  90                  95 act ttc ggc gga ggg acc aag gtg gag atc aaa                          321
Thr Phe Gly Gly Gly Thr Lys Val Glu Ile Lys
            100                 105

<210> SEQ ID NO 29
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 29 gac atc cag atg acc cag tct cca tcc tca ctg tct gca tct gta gga      48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg      96
Asp Arg Val Thr Ile Thr Cys Arg Ala Ser Gln Gly Ile Ser Ser Trp
            20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
    50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
65                  70                  75                  80 gaa gat ttt gca act tat tac tgc caa cag tat aat agt tac cct ctc      288
Glu Asp Phe Ala Thr Tyr Tyr Cys Gln Gln Tyr Asn Ser Tyr Pro Leu
                85                  90                  95 act ttc ggc gga ggg acc aag gtg gag atc aaa                          321
Thr Phe Gly Gly Gly Thr Lys Val Glu Ile Lys
            100                 105

<210> SEQ ID NO 30
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 30 gac atc cag atg acc cag tct cca tcc tca ctg tct gca tct gta gga      48
Asp Ile Gln Met Thr Gln Ser Pro Ser Ser Leu Ser Ala Ser Val Gly
1               5                   10                  15 gac aga gtc acc atc act tgt cgg gcg agt cag ggt att agc agc tgg      96
Asp Arg Val Thr Ile Thr Cys Arg Ala Ser Gln Gly Ile Ser Ser Trp
            20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
        35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
    50                  55                  60 agt gga tct ggg aca gat ttc act ctc acc atc agc aac ctg cag cct      240
Ser Gly Ser Gly Thr Asp Phe Thr Leu Thr Ile Ser Asn Leu Gln Pro
65                  70                  75                  80 gaa gat ttt gca act tat tac tgc caa cag tat aat agt tac cct ctc      288
Glu Asp Phe Ala Thr Tyr Tyr Cys Gln Gln Tyr Asn Ser Tyr Pro Leu
```

```
                    85                  90                  95
act ttc ggc gga ggg acc aag gtg gag atc aaa                          321
Thr Phe Gly Gly Gly Thr Lys Val Glu Ile Lys
            100                 105

<210> SEQ ID NO 31
<211> LENGTH: 100
<212> TYPE: PRT
<213> ORGANISM: Homo sapiens

<400> SEQUENCE: 31

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 32
<211> LENGTH: 100
<212> TYPE: PRT
<213> ORGANISM: Homo sapiens

<400> SEQUENCE: 32

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 33
<211> LENGTH: 100
<212> TYPE: PRT
<213> ORGANISM: Homo sapiens

<400> SEQUENCE: 33

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45
```

```
Trp Leu Ala Leu Ile Tyr Trp Asn Asp Lys Arg Tyr Ser Pro Ser
         50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 34
<211> LENGTH: 95
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 35
<211> LENGTH: 95
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 36
<211> LENGTH: 95
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
```

```
                    35                  40                  45
Tyr Ala Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95
```

<210> SEQ ID NO 37
<211> LENGTH: 16
<212> TYPE: PRT
<213> ORGANISM: Homo sapiens

<400> SEQUENCE: 37

```
Asn Trp Phe Asp Pro Trp Gly Gln Gly Thr Leu Val Thr Val Ser Ser
1               5                   10                  15
```

<210> SEQ ID NO 38
<211> LENGTH: 16
<212> TYPE: PRT
<213> ORGANISM: Homo sapiens

<400> SEQUENCE: 38

```
Asn Trp Phe Asp Pro Trp Gly Gln Gly Thr Leu Val Thr Val Ser Ser
1               5                   10                  15
```

<210> SEQ ID NO 39
<211> LENGTH: 16
<212> TYPE: PRT
<213> ORGANISM: Homo sapiens

<400> SEQUENCE: 39

```
Asn Trp Phe Asp Pro Trp Gly Gln Gly Thr Leu Val Thr Val Ser Ser
1               5                   10                  15
```

<210> SEQ ID NO 40
<211> LENGTH: 12
<212> TYPE: PRT
<213> ORGANISM: Homo sapiens

<400> SEQUENCE: 40

```
Leu Thr Phe Gly Gly Gly Thr Lys Val Glu Ile Lys
1               5                   10
```

<210> SEQ ID NO 41
<211> LENGTH: 12
<212> TYPE: PRT
<213> ORGANISM: Homo sapiens

<400> SEQUENCE: 41

```
Leu Thr Phe Gly Gly Gly Thr Lys Val Glu Ile Lys
1               5                   10
```

<210> SEQ ID NO 42
<211> LENGTH: 12
<212> TYPE: PRT
<213> ORGANISM: Homo sapiens

<400> SEQUENCE: 42

```
Leu Thr Phe Gly Gly Gly Thr Lys Val Glu Ile Lys
1               5                   10
```

<210> SEQ ID NO 43
<211> LENGTH: 387

```
<212> TYPE: PRT
<213> ORGANISM: Homo sapiens

<400> SEQUENCE: 43

Met Arg Ala Trp Ile Phe Phe Leu Leu Cys Leu Ala Gly Arg Ala Leu
1               5                   10                  15

Ala Gln Asn Leu Phe Thr Lys Asp Val Thr Val Ile Glu Gly Glu Val
            20                  25                  30

Ala Thr Ile Ser Cys Gln Val Asn Lys Ser Asp Ser Val Ile Gln
        35                  40                  45

Leu Leu Asn Pro Asn Arg Gln Thr Ile Tyr Phe Arg Asp Phe Arg Pro
    50                  55                  60

Leu Lys Asp Ser Arg Phe Gln Leu Leu Asn Phe Ser Ser Ser Glu Leu
65                  70                  75                  80

Lys Val Ser Leu Thr Asn Val Ser Ile Ser Asp Glu Gly Arg Tyr Phe
                85                  90                  95

Cys Gln Leu Tyr Thr Asp Pro Pro Gln Glu Ser Tyr Thr Thr Ile Thr
            100                 105                 110

Val Leu Val Pro Pro Arg Asn Leu Met Ile Asp Ile Gln Lys Asp Thr
        115                 120                 125

Ala Val Glu Gly Glu Glu Ile Glu Val Asn Cys Thr Ala Met Ala Ser
130                 135                 140

Lys Pro Ala Thr Thr Ile Arg Trp Phe Lys Gly Asn Thr Glu Leu Lys
145                 150                 155                 160

Gly Lys Ser Glu Val Glu Glu Trp Ser Asp Met Tyr Thr Val Thr Ser
                165                 170                 175

Gln Leu Met Leu Lys Val His Lys Glu Asp Asp Gly Val Pro Val Ile
            180                 185                 190

Cys Gln Val Glu His Pro Ala Val Thr Gly Asn Leu Gln Thr Gln Arg
        195                 200                 205

Tyr Leu Glu Val Gln Tyr Lys Pro Gln Val His Ile Gln Met Thr Tyr
210                 215                 220

Pro Leu Gln Gly Leu Thr Arg Glu Gly Asp Ala Leu Glu Leu Thr Cys
225                 230                 235                 240

Glu Ala Ile Gly Lys Pro Gln Pro Val Met Val Thr Trp Val Arg Val
                245                 250                 255

Asp Asp Glu Met Pro Gln His Ala Val Leu Ser Gly Pro Asn Leu Phe
            260                 265                 270

Ile Asn Asn Leu Asn Lys Thr Asp Asn Gly Thr Tyr Arg Cys Glu Ala
        275                 280                 285

Ser Asn Ile Val Gly Lys Ala His Ser Asp Tyr Met Leu Tyr Val Tyr
290                 295                 300

Asp Ser Arg Ala Gly Glu Glu Gly Ser Ile Arg Ala Val Asp His Ala
305                 310                 315                 320

Val Ile Gly Gly Val Val Ala Val Val Val Phe Ala Met Leu Cys Leu
                325                 330                 335

Leu Ile Ile Leu Gly Arg Tyr Phe Ala Arg His Lys Gly Thr Tyr Phe
            340                 345                 350

Thr His Glu Ala Lys Gly Ala Asp Asp Ala Ala Asp Ala Asp Thr Ala
        355                 360                 365

Ile Ile Asn Ala Glu Gly Gly Gln Asn Asn Ser Glu Glu Lys Lys Glu
370                 375                 380

Tyr Phe Ile
385
```

<210> SEQ ID NO 44
<211> LENGTH: 326
<212> TYPE: PRT
<213> ORGANISM: Homo sapiens

<400> SEQUENCE: 44

```
Met Arg Ala Trp Ile Phe Phe Leu Leu Cys Leu Ala Gly Arg Ala Leu
1               5                   10                  15

Thr Gln Asn Leu Phe Thr Lys Asp Val Thr Val Ile Glu Gly Glu Val
            20                  25                  30

Ala Thr Ile Ser Cys Gln Val Asn Lys Ser Asp Asp Ser Val Ile Gln
        35                  40                  45

Leu Leu Asn Pro Asn Arg Gln Thr Ile Tyr Phe Arg Asp Phe Arg Pro
    50                  55                  60

Leu Lys Asp Ser Arg Phe Gln Leu Leu Asn Phe Ser Ser Ser Glu Leu
65                  70                  75                  80

Lys Val Ser Leu Thr Asn Val Ser Ile Ser Asp Glu Gly Arg Tyr Phe
                85                  90                  95

Cys Gln Leu Tyr Thr Asp Pro Pro Gln Glu Ser Tyr Thr Thr Ile Thr
            100                 105                 110

Val Leu Val Pro Pro Arg Asn Leu Met Ile Asp Ile Gln Lys Asp Thr
        115                 120                 125

Ala Val Glu Gly Glu Ile Glu Val Asn Cys Thr Ala Met Ala Ser
    130                 135                 140

Lys Pro Ala Thr Thr Ile Arg Trp Phe Lys Gly Asn Thr Glu Leu Lys
145                 150                 155                 160

Gly Lys Ser Glu Val Glu Glu Trp Ser Asp Met Tyr Thr Val Thr Ser
                165                 170                 175

Gln Leu Met Leu Lys Val His Lys Glu Asp Asp Gly Val Pro Val Ile
            180                 185                 190

Cys Gln Val Glu His Pro Ala Val Thr Gly Asn Leu Gln Thr Gln Arg
        195                 200                 205

Tyr Leu Glu Val Gln Tyr Lys Pro Gln Val His Ile Gln Met Thr Tyr
    210                 215                 220

Pro Leu Gln Gly Leu Thr Arg Glu Gly Asp Ala Leu Glu Leu Thr Cys
225                 230                 235                 240

Glu Ala Ile Gly Lys Pro Gln Pro Val Met Val Thr Trp Val Arg Val
                245                 250                 255

Asp Asp Glu Met Pro Gln His Ala Val Leu Ser Gly Pro Asn Leu Phe
            260                 265                 270

Ile Asn Asn Leu Asn Lys Thr Asp Asn Gly Thr Tyr Arg Cys Glu Ala
        275                 280                 285

Ser Asn Ile Val Gly Lys Ala His Ser Asp Tyr Met Leu Tyr Val Tyr
    290                 295                 300

Asp Ser Arg Ala Gly Glu Glu Gly Ser Ile Arg Ala Val Asp Ala Ser
305                 310                 315                 320

His His His His His His
                325
```

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide conjugate

```
<400> SEQUENCE: 45

Pro Val Gly Val Val
1               5

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Gly Gly Ser Gly Gly Gly Gly Ser Gly Gly Gly Gly Ser
1               5                   10                  15
```